(12) United States Patent
Chiou et al.

(10) Patent No.: US 9,777,321 B2
(45) Date of Patent: Oct. 3, 2017

(54) SINGLE MOLECULE DETECTION SYSTEM AND METHODS

(71) Applicant: Industrial Technology Research Institute, Hsinchu (TW)

(72) Inventors: Chung-Fan Chiou, Hsinchu (TW); Ying-Chih Pu, Tainan (TW); Chao-Chi Pan, Hsinchu (TW); Chih-Tsung Shih, Hsinchu (TW); Ming-Chia Li, Dajia Township (TW); Chein-Shiu Kuo, Yonghe (TW); Hung-Chi Chien, Hsinchu (TW); Chang-Sheng Chu, Hsinchu (TW)

(73) Assignee: Industrial Technology Research Institute, Chutung, Hsinchu (TW)

( * ) Notice: Subject to any disclaimer, the term of this patent is extended or adjusted under 35 U.S.C. 154(b) by 0 days.

(21) Appl. No.: 15/260,773

(22) Filed: Sep. 9, 2016

(65) Prior Publication Data

US 2017/0009286 A1     Jan. 12, 2017

Related U.S. Application Data

(62) Division of application No. 13/046,457, filed on Mar. 11, 2011, now Pat. No. 9,482,615.

(Continued)

(51) Int. Cl.
*G01N 21/00* (2006.01)
*C12Q 1/68* (2006.01)
(Continued)

(52) U.S. Cl.
CPC ......... *C12Q 1/6869* (2013.01); *G01N 21/648* (2013.01); *G01N 21/6428* (2013.01);
(Continued)

(58) Field of Classification Search
None
See application file for complete search history.

(56) References Cited

U.S. PATENT DOCUMENTS 4,748,111 A   5/1988  Dattagupta et al.
4,790,614 A  12/1988  Imoto et al.
(Continued)

FOREIGN PATENT DOCUMENTS

CN   1545619 A   11/2004
CN   1576844 A    2/2005
(Continued)

OTHER PUBLICATIONS

Notice of Reasons for Rejection issued by Japanese Patent Office dated Oct. 25, 2016, in Japanese Patent Application No. 2015-236536.

(Continued)

*Primary Examiner* — Jill Warden
*Assistant Examiner* — Brittany Fisher
(74) *Attorney, Agent, or Firm* — Finnegan, Henderson, Farabow, Garrett & Dunner, LLP

(57) ABSTRACT

Embodiments encompass a single-molecule detection system and methods of using the detection system to detect an object. Further, embodiments encompass a detection system comprising a movable light coupler, a waveguide, and a light detector. Embodiments further encompass methods of single-molecule detection, including methods of single-molecule nucleic acid sequencing.

2 Claims, 24 Drawing Sheets
(4 of 24 Drawing Sheet(s) Filed in Color)

Related U.S. Application Data

(60) Provisional application No. 61/314,037, filed on Mar. 15, 2010.

(51) Int. Cl.
    *G01N 21/64* (2006.01)
    *G01N 21/77* (2006.01)

(52) U.S. Cl.
    CPC ..... *G01N 21/6452* (2013.01); *G01N 21/6454* (2013.01); *G01N 21/7703* (2013.01); *G01N 2021/6439* (2013.01); *G01N 2201/08* (2013.01); *G01N 2201/12* (2013.01)

(56) References Cited

U.S. PATENT DOCUMENTS

| | | | |
|---|---|---|---|
| 5,034,613 A | 7/1991 | Denk et al. | |
| 5,162,887 A | 11/1992 | Dierschke | |
| 5,185,832 A | 2/1993 | Coutandin et al. | |
| 5,302,509 A | 4/1994 | Cheeseman | |
| 5,355,022 A | 10/1994 | Sugahara et al. | |
| 5,391,480 A | 2/1995 | Davis et al. | |
| 5,405,747 A | 4/1995 | Jett et al. | |
| 5,460,975 A | 10/1995 | Freitag et al. | |
| 5,674,743 A | 10/1997 | Ulmer | |
| 5,717,602 A | 2/1998 | Kenning | |
| 5,750,341 A | 5/1998 | Macevicz | |
| 5,795,782 A | 8/1998 | Church et al. | |
| 5,965,875 A | 10/1999 | Merrill | |
| 6,013,434 A | 1/2000 | Tregear et al. | |
| 6,091,874 A | 7/2000 | Higashi et al. | |
| 6,123,819 A | 9/2000 | Peeters | |
| 6,153,737 A | 11/2000 | Manoharan et al. | |
| 6,197,513 B1 | 3/2001 | Coull et al. | |
| 6,210,973 B1 | 4/2001 | Pettit | |
| 6,232,075 B1 | 5/2001 | Williams | |
| 6,255,083 B1 | 7/2001 | Williams | |
| 6,306,607 B2 | 10/2001 | Williams | |
| 6,344,653 B1 | 2/2002 | Webb et al. | |
| 6,362,002 B1 | 3/2002 | Denison et al. | |
| 6,374,019 B1 | 4/2002 | Gustavsson | |
| 6,413,792 B1 | 7/2002 | Sauer et al. | |
| 6,618,536 B1 * | 9/2003 | Heideman | G01N 21/7703 |
| | | | 356/481 |
| 6,762,048 B2 | 7/2004 | Williams | |
| 6,834,149 B1 * | 12/2004 | Dietz | G01N 21/7703 |
| | | | 385/122 |
| 6,917,726 B2 | 7/2005 | Levene et al. | |
| 6,946,249 B2 | 9/2005 | Head et al. | |
| 7,013,054 B2 | 3/2006 | Levene et al. | |
| 7,015,485 B2 | 3/2006 | Kitagawa | |
| 7,033,764 B2 | 4/2006 | Korlach et al. | |
| 7,052,847 B2 | 5/2006 | Korlach et al. | |
| 7,056,661 B2 | 6/2006 | Korlach et al. | |
| 7,056,676 B2 | 6/2006 | Korlach et al. | |
| 7,060,440 B1 | 6/2006 | Kless | |
| 7,081,526 B2 | 7/2006 | Marciacq et al. | |
| 7,167,735 B2 | 1/2007 | Uchida et al. | |
| 7,170,050 B2 | 1/2007 | Turner et al. | |
| 7,175,811 B2 | 2/2007 | Bach et al. | |
| 7,181,122 B1 | 2/2007 | Levene et al. | |
| 7,226,777 B2 | 6/2007 | Kawamura et al. | |
| 7,229,799 B2 | 6/2007 | Williams | |
| 7,282,337 B1 | 10/2007 | Harris | |
| 7,292,742 B2 | 11/2007 | Levene et al. | |
| 7,302,146 B2 | 11/2007 | Turner et al. | |
| 7,313,308 B2 | 12/2007 | Turner et al. | |
| 7,315,019 B2 | 1/2008 | Turner et al. | |
| 7,316,930 B1 | 1/2008 | Montalbo | |
| 7,329,492 B2 | 2/2008 | Hardin et al. | |
| 7,361,466 B2 | 4/2008 | Korlach et al. | |
| 7,384,797 B1 | 6/2008 | Blair | |
| 7,416,844 B2 | 8/2008 | Korlach et al. | |
| 7,485,424 B2 | 2/2009 | Korlach et al. | |
| 7,486,865 B2 | 2/2009 | Foquet et al. | |
| 7,666,645 B2 | 2/2010 | Wang | |
| 7,767,441 B2 | 8/2010 | Chiou et al. | |
| 7,805,081 B2 | 9/2010 | Lundquist et al. | |
| 7,943,305 B2 | 5/2011 | Korlach et al. | |
| 7,943,307 B2 | 5/2011 | Korlach et al. | |
| 8,252,581 B2 | 8/2012 | Joseph et al. | |
| 8,603,741 B2 | 12/2013 | Emig et al. | |
| 2002/0090630 A1 | 7/2002 | Hazama | |
| 2002/0110839 A1 * | 8/2002 | Bach | B82Y 5/00 |
| | | | 435/7.9 |
| 2002/0141062 A1 | 10/2002 | Christoffersen et al. | |
| 2002/0154315 A1 | 10/2002 | Myrick | |
| 2003/0064366 A1 | 4/2003 | Hardin et al. | |
| 2003/0087242 A1 | 5/2003 | Mirkin et al. | |
| 2003/0092005 A1 | 5/2003 | Levene et al. | |
| 2003/0143724 A1 | 7/2003 | Cerrina et al. | |
| 2004/0038331 A1 | 2/2004 | Reddy et al. | |
| 2004/0152119 A1 | 8/2004 | Sood et al. | |
| 2005/0001239 A1 | 1/2005 | Ishibashi et al. | |
| 2005/0089298 A1 | 4/2005 | Maxwell et al. | |
| 2005/0100919 A1 | 5/2005 | Stanton | |
| 2005/0201899 A1 | 9/2005 | Weisbuch | |
| 2005/0208557 A1 | 9/2005 | Korlach et al. | |
| 2005/0266424 A1 | 12/2005 | Hardin et al. | |
| 2005/0275839 A1 | 12/2005 | Robinson et al. | |
| 2006/0057606 A1 | 3/2006 | Korlach et al. | |
| 2006/0062693 A1 | 3/2006 | Muraishi | |
| 2006/0068506 A1 | 3/2006 | Uyeda et al. | |
| 2006/0134666 A1 | 6/2006 | Korlach et al. | |
| 2006/0160113 A1 | 7/2006 | Korlach et al. | |
| 2006/0228722 A1 | 10/2006 | Kim et al. | |
| 2007/0026447 A1 | 2/2007 | Korlach et al. | |
| 2007/0036511 A1 | 2/2007 | Lundquist et al. | |
| 2007/0083122 A1 | 4/2007 | Alfano et al. | |
| 2007/0109545 A1 | 5/2007 | Chau et al. | |
| 2007/0141598 A1 | 6/2007 | Turner et al. | |
| 2007/0172858 A1 | 7/2007 | Hardin et al. | |
| 2007/0172861 A1 | 7/2007 | Hardin et al. | |
| 2007/0172862 A1 | 7/2007 | Hardin et al. | |
| 2007/0172863 A1 | 7/2007 | Hardin et al. | |
| 2007/0172864 A1 | 7/2007 | Gao et al. | |
| 2007/0172865 A1 | 7/2007 | Hardin et al. | |
| 2007/0172866 A1 | 7/2007 | Hardin et al. | |
| 2007/0172867 A1 | 7/2007 | Hardin et al. | |
| 2007/0172868 A1 | 7/2007 | Hardin et al. | |
| 2007/0184475 A1 | 8/2007 | Hardin et al. | |
| 2007/0238679 A1 | 10/2007 | Rank et al. | |
| 2007/0269345 A1 | 11/2007 | Schilffarth et al. | |
| 2007/0273290 A1 | 11/2007 | Ashdown | |
| 2007/0275395 A1 | 11/2007 | Hardin et al. | |
| 2007/0292867 A1 | 12/2007 | Hardin et al. | |
| 2008/0037008 A1 | 2/2008 | Shepard et al. | |
| 2008/0050747 A1 | 2/2008 | Korlach et al. | |
| 2008/0061683 A1 | 3/2008 | Bertram | |
| 2008/0081769 A1 | 4/2008 | Hassibi | |
| 2008/0087843 A1 | 4/2008 | Medintz et al. | |
| 2008/0094632 A1 | 4/2008 | Harsh | |
| 2008/0105831 A1 | 5/2008 | Reel et al. | |
| 2008/0108082 A1 | 5/2008 | Rank et al. | |
| 2008/0176769 A1 | 7/2008 | Rank et al. | |
| 2008/0177139 A1 | 7/2008 | Courtney et al. | |
| 2008/0199932 A1 | 8/2008 | Hanzel et al. | |
| 2008/0227654 A1 | 9/2008 | Korlach et al. | |
| 2008/0241833 A1 | 10/2008 | Williams | |
| 2009/0015831 A1 | 1/2009 | Yguerabide et al. | |
| 2009/0026978 A1 | 1/2009 | Robinson | |
| 2009/0082212 A1 | 3/2009 | Williams | |
| 2009/0087850 A1 | 4/2009 | Eid et al. | |
| 2009/0137007 A1 | 5/2009 | Korlach et al. | |
| 2009/0146076 A1 | 6/2009 | Chiou et al. | |
| 2009/0170074 A1 | 7/2009 | Williams | |
| 2009/0263797 A1 | 10/2009 | Zon | |
| 2009/0275036 A1 | 11/2009 | Hardin et al. | |
| 2009/0286245 A1 | 11/2009 | Bjornson et al. | |
| 2009/0294813 A1 | 12/2009 | Gambino et al. | |
| 2009/0305278 A1 | 12/2009 | Hardin et al. | |
| 2009/0312188 A1 * | 12/2009 | Duer | B01L 3/502715 |
| | | | 506/6 |

(56) References Cited

U.S. PATENT DOCUMENTS

| | | |
|---|---|---|
| 2010/0009872 A1 | 1/2010 | Eid et al. |
| 2010/0035268 A1 | 2/2010 | Beecham et al. |
| 2010/0055666 A1 | 3/2010 | Wimberger-Friedl et al. |
| 2010/0065726 A1 | 3/2010 | Zhong et al. |
| 2010/0075328 A1 | 3/2010 | Bjornson et al. |
| 2010/0093068 A1 | 4/2010 | Williams |
| 2010/0121582 A1 | 5/2010 | Pan et al. |
| 2010/0255463 A1 | 10/2010 | Harsin et al. |
| 2010/0255487 A1 | 10/2010 | Beechem et al. |
| 2010/0256016 A1 | 10/2010 | Blair et al. |
| 2010/0256918 A1 | 10/2010 | Chen et al. |
| 2010/0282617 A1 | 11/2010 | Rothberg et al. |
| 2010/0304358 A1 | 12/2010 | Nie et al. |
| 2010/0304367 A1 | 12/2010 | Hardin et al. |
| 2010/0317005 A1 | 12/2010 | Hardin et al. |
| 2011/0014604 A1 | 1/2011 | Hardin et al. |
| 2011/0014612 A1 | 1/2011 | Hendricks et al. |
| 2011/0021383 A1 | 1/2011 | Hardin et al. |
| 2011/0059436 A1 | 3/2011 | Hardin et al. |
| 2011/0111401 A1 | 5/2011 | Korlach et al. |
| 2011/0130297 A1 | 6/2011 | Badorrek et al. |
| 2011/0210094 A1 | 9/2011 | Gray et al. |
| 2011/0223590 A1 | 9/2011 | Chiou et al. |
| 2011/0300534 A1 | 12/2011 | Chiou et al. |
| 2011/0306039 A1 | 12/2011 | Chiou et al. |
| 2011/0306143 A1 | 12/2011 | Chiou et al. |
| 2013/0004967 A1* | 1/2013 | Halverson ............ B01L 3/50853 435/7.8 |

FOREIGN PATENT DOCUMENTS

| | | |
|---|---|---|
| CN | 10708680 A | 12/2005 |
| CN | 101168773 A | 4/2008 |
| CN | 101384729 A | 3/2009 |
| CN | 101654712 A | 2/2010 |
| CN | 101711257 A | 5/2010 |
| CN | 101726462 A | 6/2010 |
| EP | 1309719 | 2/2002 |
| EP | 1 089 067 B1 | 12/2004 |
| EP | 1102782 B1 | 3/2006 |
| JP | 62-165129 | 7/1987 |
| JP | H4-303972 A | 10/1992 |
| JP | 2005-118991 | 5/1993 |
| JP | 2000-173093 | 6/2000 |
| JP | 2001-161696 A | 6/2001 |
| JP | 2003-502847 A | 1/2003 |
| JP | 2003-521684 A | 7/2003 |
| JP | 2003-295064 A | 10/2003 |
| JP | 2003-532123 A | 10/2003 |
| JP | 2004-163257 A | 6/2004 |
| JP | 2004-219330 | 8/2004 |
| JP | 2004-523243 A | 8/2004 |
| JP | 2004-525342 | 8/2004 |
| JP | 2005-127795 | 5/2005 |
| JP | 2005-156538 A | 6/2005 |
| JP | 2005-165256 | 6/2005 |
| JP | 2005-172840 A | 6/2005 |
| JP | 2006-220645 | 8/2006 |
| JP | 2007-531527 A | 11/2007 |
| JP | 2008-520975 A | 6/2008 |
| JP | 2009-511896 A | 3/2009 |
| JP | 2009-537148 A | 10/2009 |
| JP | 2013-522605 | 6/2013 |
| KR | 10-2010-0019409 | 2/2010 |
| WO | WO 89/03432 A1 | 4/1989 |
| WO | WO 00/36152 A1 | 6/2000 |
| WO | WO 01/42768 A1 | 6/2001 |
| WO | WO 00/36151 A9 | 8/2001 |
| WO | WO 01/84197 A1 | 11/2001 |
| WO | WO 01/92501 A1 | 12/2001 |
| WO | WO 02/04680 A2 | 1/2002 |
| WO | WO 00/70073 A9 | 4/2002 |
| WO | WO 02/066683 A2 | 8/2002 |
| WO | WO 02/072892 A1 | 9/2002 |
| WO | WO 02/073158 A2 | 9/2002 |
| WO | WO 03/003015 A2 | 1/2003 |
| WO | WO 03/064997 A2 | 8/2003 |
| WO | WO 2004/011605 A2 | 2/2004 |
| WO | WO 2005/019419 A2 | 3/2005 |
| WO | WO 2005/080605 A2 | 9/2005 |
| WO | WO 2005/098042 A2 | 10/2005 |
| WO | WO 2006/055521 A2 | 5/2006 |
| WO | WO 2006/073504 A2 | 7/2006 |
| WO | WO 2007/084702 A2 | 7/2007 |
| WO | WO 2007/091280 A1 | 8/2007 |
| WO | WO 2007/119067 A1 | 10/2007 |
| WO | WO 2008/002101 A1 | 1/2008 |
| WO | WO 2008/016906 A2 | 2/2008 |
| WO | WO 2008/032096 A2 | 3/2008 |
| WO | WO 2009/017678 A2 | 2/2009 |
| WO | WO 2009/056065 A1 | 5/2009 |
| WO | WO 2009/060360 A2 | 5/2009 |
| WO | WO 2009/145818 | 12/2009 |

OTHER PUBLICATIONS

Abramova et al., "Design and synthesis of dinucleotide 5'-triphosphates with expanded functionality," *Bioorganic & Medicinal Chemistry*, 16, pp. 9127-9132 (2008).

Adessi et al., "Solid phase DNA amplification: characterisation of primer attachment and amplification mechanisms," *Nucleic Acids Research* 28(20):e87 (8 pages) (2000).

Anker et al., "Magnetically-modulated Optical Nanoprobes (MagMOONs) and Systems," *Journal of Magnetism and Magnetic Materials* 293:655-662 (2005).

Blackard et al., "Intrahepatic Cytokine Expression is Downregulated During HCV/HIV Co-Infection," *J. Med. Virol.* 78:202-207 (2006).

Cao et al., DNA-modified core-shell Ag/Au nanoparticles, 2001, *J. Am. Chem. Soc.* 123:7961-7962.

Cheng, "High-Speed DNA-Sequence Analysis" *Prog. Biochem. Biophys.* 22:223-227 (1995) (English abstract on p. 277).

Clarke et al., "Continuous base identification for single-molecule nanopore DNA sequencing" *Nature Nanotechnol.* 4:265-270 (2009).

Dapprich et al., "DNA Attachment to Optically Trapped Beads in Microstructures Monitored by Bead Displacement" *Bioimaging* 6:25-32 (1998).

Dorre et al., "Techniques for Single Molecule Sequencing" *Bioimaging* 5:139-152 (1997).

Eid et al., "Real-Time DNA Sequencing from Single Polymerase Molecules," *Science* 323: 133-138 (2009).

Examiner's Report dated Apr. 5, 2013, issued in Canadian Patent Application No. 2,763,100.

Extended European Search Report issued by the European Patent Office, dated Aug. 12, 2011, in European Patent Application No. 10750363.3 (17 pages).

Extended European Search Report issued by the European Patent Office, dated Aug. 16, 2011, in European Patent Application No. 10196884.0 (10 pages).

Fidalgo Da Silva and Reha-Krantz, "DNA polymerase proofreading: active site switching catalyzed by the bacteriophage T4 DNA polymerase" *Nucl. Acids Res.* 35(16):5452-5463 (2007).

Fife et al., "A Multi-Aperture Image Sensor With 0.7 µm Pixels in 0.11 µm CMOS Technology," *IEEE Journal of Solid-State Circuits* 43(12):2990-3005 (Dec. 2008).

Goodwin et al., "Application of Single Molecule Detection to DNA Sequencing" *Nucleos. Nucleot.* 16:543-550 (1997).

Guo et al., "An Integrated System for DNA Sequencing by Synthesis Using Novel Nucleotide Analogues" *Accounts of Chemical Research*, 43(4):551-63 (2010).

Han et al., "High performance electrophoresis system for site-specific entrapment of nanoparticles in a nanoarray," *Proc. of SPIE* 7574:75740L (2010).

Harris et al., "Single-Molecule DNA Sequencing of a Viral Genome," *Science* 320:106-109 (2008).

(56) References Cited

OTHER PUBLICATIONS

Howorka et al., "Sequence-specific detection of individual DNA strands using engineered nanopores" Nat. Biotechnol. 19:636-639 (2001).
Hyman, "A New Method of Sequencing DNA" Anal. Biochem. 174:423-436 (1988).
Japanese Patent Application No. 2011-553266: Notification of Reasons for Refusal, dated Mar. 12, 2014, with English translation (8 pages).
Kamtekar et al., "Insights into Strand Displacement and Processivity from the Crystal Structure of the Protein-Primed DNA Polymerase of Bacteriophage Ø29," Molecular Cell 16:609-618 (Nov. 19, 2004).
Kang et al., "Synthesis and Characterization of Nanometer-Size $Fe_3O_4$ and $\gamma$-$Fe_2O_3$ Particles," Chem. Mater. 8(9):2209-2211 (1996).
Kim et al., "Crystal structure of Thermus aquaticus DNA polymerase," Nature 376:612-616 (Aug. 17, 1995).
Korlach et al., "Selective aluminum passivation for targeted immobilization of single DNA polymerase molecules in zero-mode waveguide nanostructures," Proc. Natl. Acad. Sci. USA 105(4):1176-1181 (Jan. 29, 2008).
Lehmuskero et al., Refractive index and extinction coefficient dependence of thin Al and Ir films on deposition technique and thickness, 2007, Optics Express 15(17): p. 10744-10752.
Levene et al., "Zero-Mode Waveguides for Single-Molecule Analysis at High Concentrations," Science 299:682-686 (Jan. 31, 2003).
Levin et al., "Position-dependent effects of locked nucleic acid (LNA) on DNA sequencing and PCR primers," Nucl. Acids Res. 34(20):e142 (2006).
McGuire et al. "The Future of Personal Genomics" Science 317:1687 (2007).
McNaughton et al., "Fabrication of uniform half-shell magnetic nanoparticles and microspheres with applications as magnetically modulated optical nanoprobes," Submitted to Applied Physics Letters, Jun. 16, 2005; 6 pp. [online]; retrieved from the Internet: http://arxiv.org/abs/cond-mat/0506418.
Medintz et al., "Quantum dot bioconjugates for imaging, labelling and sensing," Nature Materials 4:435-446 (2005).
Metwalli et al., "Surface characterizations of mono-, di-, and tri-aminosilane treated glass substrates" Journal of Colloid and Interface Science 298:825-831 (2006).
Metzker, "Sequencing technologies—the next generation," Nature Reviews Genetics 11:31-46 (2010).
Moerner et al., "Methods of single-molecule fluorescence spectroscopy and microscopy," Review of Scientific Instruments 74(8):3597-3619 (2003).
Nandwana et al., "Size and Shape Control of Monodisperse FePt Nanoparticles," J. Phys. Chem. C 111(11):4185-4189 (2007).
Neamen, Semiconductor Physics and Devices, pp. 17-19, McGraw Hill (1997).
Niclass et al., "A Single Photon Avalanche Diode Array Fabricated in Deep-Submicron CMOS Technology," IEEE Design, Automation and Test in Europe, 2006. Proceedings. pp. 81-86 (Mar. 2006).
Office Action (Notice to Submit a Response) dated Apr. 2, 2013, issued in Korean Patent Application No. 10-2011-7031724.
Office Action (Patent Examination Report No. 1) dated Oct. 15, 2012, issued in Australian Patent Application No. 2011229691.
Ozsolak et al., "Direct RNA sequencing," Nature 461:814-818 (2009).
Park et al., "Multifunctional Nanoparticles for Photothermally Controlled Drug Delivery and Magnetic Resonance Imaging Enhancement," Small 4(2):192-196 (2008).
Perro et al., "Design and synthesis of Janus micro- and nanoparticles," J. Mater. Chem. 15:3745-3760 (2005).
Qiu et al., "Fluorescence single-molecule counting assays for high-sensitivity detection of cytokines and chemikines," Clin. Chem. 53(11):2010-2012 (2007).
Ramadan et al., "Customized trapping of magnetic particles," Microfluidics and Nanofluidics 6(1):53-62 (2009).
Reddy et al., "Processive Proofreading Is Intrinsic to T4 DNA Polymerase" J. Biol. Chem. 267(20): 14157-14166 (1992).
Reha-Krantz, "Regulation of DNA Polymerase Exonucleolytic Proofreading Activity: Studies of Bacteriophage T4 'Antimutator' DNA Polymerases" Genetics 148:1551-1557 (1998).
Ronaghi et al. "A Sequencing Method Based on Real-Time Pyrophosphate" Science 281:363-365 (1998).
Sauer et al., "Detection and identification of single dye labeled mononucleotide molecules released from and optical fiber in a microcapillary: First steps towards a new single molecule DNA sequencing technique" Phys. Chem. Chem. Phys. 1(10):247-1-2477 (1999).
Schena (ed.), Microarray Biochip Technology. Eaton Publishing Co; pp. 28, 76-78 (Apr. 15, 2000).
Schmitt et al., "High Refractive-Index Waveguide Platforms for chemical and biosensing," in Optical Guided-Wave Chemical and Biosensors I. M. Zourob and A. Lakhtakia (Eds.), 2010; pp. 7 and 21.
Shendure et al., "Accurate Multiplex Polony Sequencing of an Evolved Bacterial Genome," Science 309:1728-1732 (2005).
Shendure et al., "Advanced Sequencing Technologies: Methods and Goals," Nat. Rev. Genet. 5:335-344 (2004).
Spring et al., "Introduction to fluorescence microscopy," Nikon microscopy, 10 pages.
Stevens et al., "Low-Crosstalk and Low-Dark-Current CMOS Image-Sensor Technology Using a Hole-Based Detector," IEEE International Solid-State Circuits Conference, Feb. 3-7, 2008. Digest of Technical Papers; p. 60-595 (2008).
Sze, Physics of Semiconductor Devices, pp. 674-675, John Wiley & Sons, Inc. (3d ed. 2007).
Tessier et al., "Ligation of single-stranded oligodeoxyribonucleotides by T4 RNA ligase," Anal. Biochem., vol. 158, pp. 171-178 (1986).
Turcatti et al., "A new class of cleavable fluorescent nucleotides: synthesis and optimization as reversible terminators for DNA sequencing by synthesis" Nucleic Acids Res., 36(4 ):e25, doi: 10.1093/nar/gkn021, published online Feb. 7, 2008.
Velev et al., "Particle-localized AC and DC manipulation and electrokinetics," Ann. Rep. Prog. Chem., Sect. C 105:213-246 (2009).
Walter et al., "Do-it-yourself guide: how to use the modern single-molecule toolkit," Nature Methods 5:475-489 (2008).
Wang et al., "One-Pot Synthesis and Bioapplication of Amine-Functionalized Magnetite Nanoparticles and Hollow Nanospheres," Chem. Eur. J. 12:6341-6347 (2006).
Wang et al., "Single-Molecule Tracing on a Fluidic Microchip for Quantitative Detection of Low-Abundance Nucleic Acids," J. Am. Chem. Soc. 127:5354-5359 (2005).
Wu et al., "Bioinspired Nanocorals with Decoupled Cellular Targeting and sensing Functionality," Small 6(4):503-507 (Feb. 22, 2010).
Zhang et al., "Single-quantum-dot-based DNA nanosensor," Nature Materials 4:826-831 (2005).
Zheng et al., "Quasicubic $\alpha$-Fe2O3 Nanoparticles with Excellent Catalytic Performance," J. Phys. Chem. B 110(7) (2006).
Notice of Reason for Rejection issued by the Japanese Patent Office dated Feb. 2, 2017 in counterpart Japanese Application No. 2015-236536.

* cited by examiner

SINGLE MOLECULE DETECTION SYSTEM AND METHODS

PRIORITY INFORMATION

This application is a division of application Ser. No. 13/046,457 filed Mar. 11, 2011, which claims priority to U.S. Application Ser. No. 61/314,037, filed Mar. 15, 2010, both of which are incorporated herein by reference in their entirety.

TECHNICAL FIELD

The application relates to a single-molecule detection system and methods of using the detection system to detect an object. Further, the application relates to a detection system comprising a movable light coupler, a waveguide, and a light detector. The application also relates to methods of loading samples to a single-molecule detection system. The application further relates to methods of single-molecule detection, including methods of single-molecule nucleic acid sequencing.

BACKGROUND

Most conventional chemical or biochemical assays are based on "bulk" measurements. In such measurements, a collective behavior of a plurality of molecules within a certain volume of a sample solution is measured to determine the properties of the molecules. However, in many situations, bulk measurement approaches cannot be utilized, such as when sample volume is too small or the concentration of a target molecule is too low for a given technique's limit of sensitivity in detecting target molecules. In recent years, the detection of single molecules has become possible. Single-molecule detection offers much higher sensitivity and provides more detailed information than conventional bulk measurements. The development of single-molecule instrument sensitivity also promises new opportunities for high-sensitivity biological molecule detection and diagnosis, as described in Qiu, H., et al., "Fluorescence single-molecule counting assays for high-sensitivity detection of cytokines and chemokines", CLINICAL CHEMISTRY 53(11):2010-2012 (2007).

A description of approaches for achieving single-molecule detection is provided in Moerner, W. E. and Fromm, D. P., "REVIEW ARTICLE: Methods of single-molecule fluorescence spectroscopy and microscopy", REVIEW OF SCIENTIFIC INSTRUMENTS 74(8): 3597-3619 (2003) and in Walter, N. G., et al., "Do-it-yourself guide: how to use the modern single-molecule toolkit", NATURE METHODS 5:475-489 (2008). These reviews also discuss methods and apparatuses known in the art that have been used or proposed for single-molecule detection. Applications of single-molecule detection include single-molecule DNA sequencing, single-molecule biomarker detection and miniaturized flow-cytometry-like detection.

Optimized systems and methods for single molecule detection have great potential for accelerating DNA sequencing technology. The Human Genome Project (HGP) spurred a great increase in DNA sequencing throughput. This increase, along with technical improvements, resulted in a corresponding drop in sequencing costs. While the first genome required 13 years and nearly three billion US dollars to completely sequence, it has been predicted that DNA sequencing technologies may ultimately become sufficiently affordable for personal genomics to be an integral component of routine clinical care (McGuire et al., SCIENCE 317: 1687 (2007)). Personal genomes represent a paradigm shift in medical treatment for both patients and health care providers. By managing genetic risk factors for disease, health care providers can more readily practice preventative medicine and provide customized treatment. With large banks of completed genomes, drug design and administration can be more efficient, thereby accelerating the nascent field of pharmacogenomics. However, this acceleration will depend on the realization of robust, high-throughput, and low-cost DNA sequencing technologies.

To achieve single-molecule detection, an optical system must be able to selectively excite the molecule of interest in a complicated environment, and be able to avoid the interference from the background noise and detect the weak light emitted from that single molecule. One of the approaches for achieving single-molecule detection is locating the molecule of interest inside a confined space facilitating detection of light emitted from one molecule. U.S. Pat. No. 6,917,726 discloses a microscopy system incorporating a zero-mode waveguide (ZMW), which can facilitate the detection of single molecules by using nano-scale wells in which defined excitation light fields are created. Placement of molecules within these nanowells, and thus within these defined excitation light fields, greatly minimizes noise, thereby enhancing the detectability of light emitted from a single molecule. See also, for example, U.S. Pat. No. 6,917,726; U.S. Pat. No. 7,170,050; and U.S. Pat. No. 7,486,865. However, loading of the single-molecule sample into the excitation field requires attachment of the molecules to the bottom of the ZMW in the nanowells, which is difficult and inefficient (Eid et al., SCIENCE, 323:133-138 (2009)). Only wells containing one single-molecule sample are useful, while empty wells or wells containing multiple single-molecule samples are not.

Improved methods of sample loading with higher success rates are disclosed in U.S. patent publication no. 2010/0009872. These methods utilize a nano-scale particle to carry a single-molecule sample to the top opening of the nanowell and deliver the sample to the bottom of the well, where the sample may be exposed to the excitation field. However, the process involves many steps and chemical reactions to transfer the single-molecule sample from the nanoparticle carrier to the bottom of the well. Furthermore, the loaded wells are either impossible or difficult to reuse.

International Patent Publication Number WO 2009/017678 disclosed methods of single-molecule nucleic acid sequencing in which a single polymerase is immobilized on a surface to repeatedly sequence a circular nucleic acid template, thereby improving the accuracy of single-molecule sequencing. In this method for optical detection of single-molecule sequencing, immobilization of reactants directly on the surface confined reactions to within a zeptoliter volume. However, the difficulty of binding a single molecule of an enzyme or a nucleic acid onto the surface limits high-throughput use. Furthermore, a sequencing reaction in which a polymerase is immobilized directly on the surface will be terminated whenever the polymerase loses its activity, preventing completion of sequencing analysis at that site. In order to immobilize a molecule or enzyme in place, as set forth in WO 2009/017678, the region of surface must be well-defined and the chemical property of that region must be precisely controlled. This presents difficulties and added costs for device manufacturing.

Therefore, there is a need for improved systems and methods for detection of single-molecule objects.

SUMMARY OF CERTAIN EMBODIMENTS

There is provided a system for detecting an object, such as a single-molecule object, wherein the detection system comprises a movable light coupler, a light detector, and a waveguide which comprises a core layer, a first cladding layer, and at least one adapter site for the movable light coupler formed in at least the first cladding layer. In some embodiments, the detection system comprises a light source.

In some embodiments, the movable light coupler is able to localize an object to the at least one adapter site formed in at least the first cladding layer of the waveguide. In some embodiments, the adapter site for the movable light coupler is a nanowell. In some embodiments, the movable light coupler is a nano-scale particle. In some embodiments, the movable light coupler is a nano-scale sphere.

Furthermore, there is provided a method of detecting a single-molecule object, comprising the steps of a) introducing an incident light from a light source into a waveguide, thereby forming an excitation light in the waveguide, b) localizing a single-molecule object on a movable light coupler, c) localizing the movable light coupler of (b) at an adapter site for a movable light coupler formed in at least a first cladding layer of the waveguide, and d) exciting, by the excitation light, a single-molecule object localized on the movable light coupler, causing the single-molecule object to emit a light to be detected by a light detector.

There is provided a method of detecting a single-molecule object comprising the steps of a) providing a detection apparatus comprising (i) a movable light coupler, (ii) a waveguide comprising a core layer and a first cladding layer, wherein at least one adapter site for the movable light coupler is formed in at least the first cladding layer, and (iii) a light detector; b) providing at least one binding moiety capable of binding a single-molecule object; c) localizing the at least one binding moiety individually on the surface of the movable light coupler; d) providing a single-molecule object sample to one binding moiety localized on the movable coupler; e) localizing at the adapter site the movable light coupler on which the at least one binding moiety and single-molecule object are localized; f) introducing an incident light from a light source into the waveguide, thereby forming an excitation light in the waveguide; and g) exciting, by the excitation light, a single-molecule object bound to the at least one binding moiety localized on the movable light coupler, causing the single-molecule object to emit a light to be detected by a light detector.

There is provided a method of sequencing a nucleic acid, comprising the steps of a) providing a detection apparatus comprising (i) a movable light coupler, (ii) a waveguide comprising a core layer and a first cladding layer, wherein at least one adapter site for the movable light coupler is formed in at least the first cladding layer, and (iii) a light detector; b) providing at least one nucleic acid molecule; c) localizing the at least one nucleic acid molecule individually on the movable light coupler; d) localizing at the adapter site the movable light coupler on which at least one nucleic acid is localized; e) performing single molecule sequencing-by-synthesis of the at least one nucleic acid molecule, wherein the single molecule nucleic acid sequencing-by-synthesis produces an emitted light correlated to the identity of at least one base in the nucleic acid; f) detecting the emitted light with the detector, resulting in an output signal; and g) processing the output signal to determine an identity of at least one base comprised by the nucleic acid.

Additional objects and advantages will be set forth in part in the description which follows, and in part will be obvious from the description, or may be learned by practice of the embodiments. The objects and advantages of the invention will be realized and attained by means of the elements and combinations particularly pointed out in the appended claims.

It is to be understood that both the foregoing general description and the following detailed description are exemplary and explanatory only and are not restrictive of the embodiments, as claimed.

The accompanying drawings, which are incorporated in and constitute a part of this specification, illustrate several embodiments of the invention and together with the description, serve to explain the principles thereto.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

DETAILED DESCRIPTION OF THE EMBODIMENTS

Figure 1:
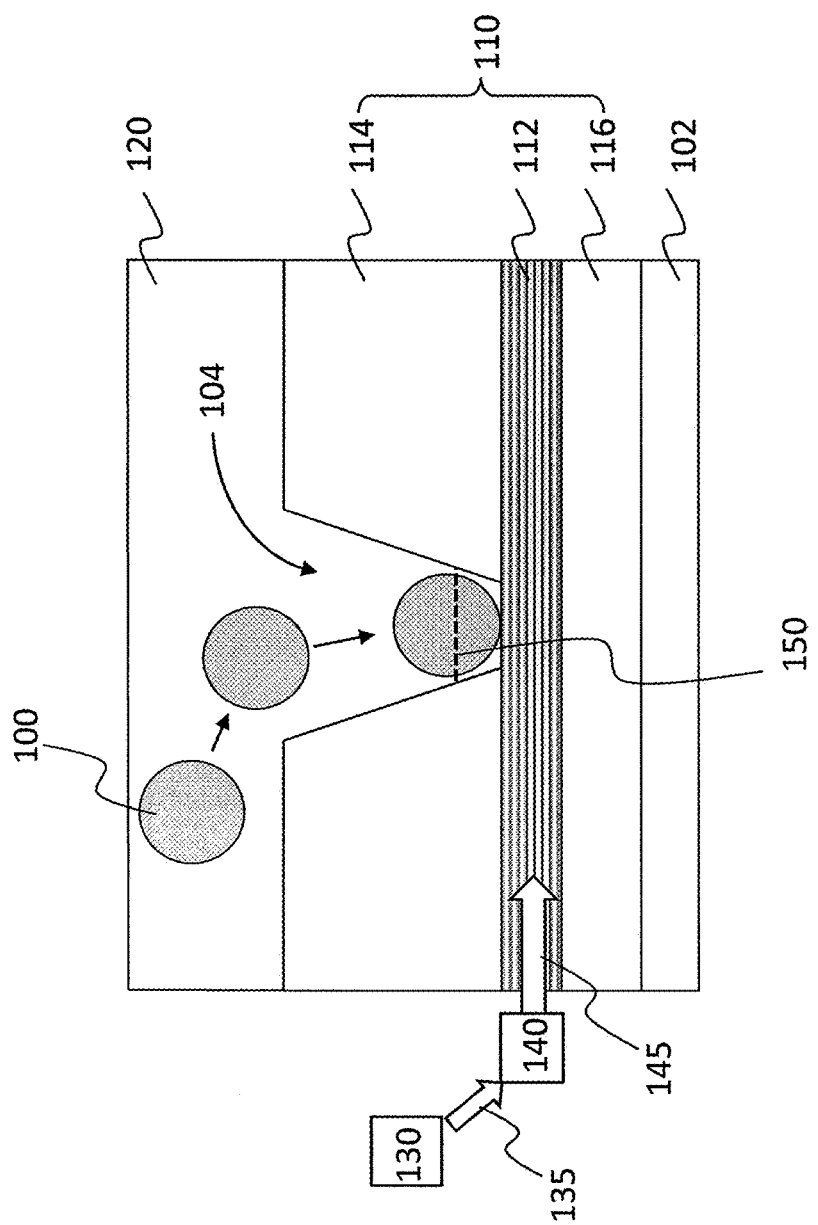
FIG. 1 is a schematic view of a detection system consistent with certain embodiments.

Embodiments include a detection system and method of using the detection system for detecting an object, such as a single-molecule object. The detection system is capable of detecting weak light emitted from the object.

To achieve single-molecule detection, an optical system must be able to selectively excite the molecule of interest in a complicated environment, and able to avoid the interference from the background noise and detect the weak light emitted from that single molecule. To achieve single-molecule detection, and in one embodiment, a system may need to possess at least the following two criteria: 1) it has both a confined excitation space and a confined observation space, and 2) the confined excitation space and confined observation space should fully or partially overlap, and the overlapping region should be small enough to ensure that the light emitted from the target single molecule is higher than the background to provide a detectable signal-to-noise ratio (SNR). For example, the volume of the overlapping region often must be on the order of or smaller than a femtoliter. More particularly, the volume of the overlapping region often must be in the attoliter to zeptoliter range. Moreover, it may also be important to prevent the excitation light from reaching the detector.

Embodiments overcome the difficulties of loading a single-molecule sample to a detection system by use of a movable light coupler to carry a single-molecule sample to an adapter site for the movable light coupler formed in a waveguide. A confined space suitable for single-molecule detection may be formed after the movable light coupler docks at the adapter site. The design of the movable light coupler and adapter site may prevent a second coupler from docking to the same adapter site. In one embodiment, the single molecule sample, e.g., an enzyme, can be loaded to the coupler before the coupler is introduced to the waveguide, and in one embodiment, all or a sample of the loaded couplers can be pre-screened to ensure that each coupler carries one and only one sample molecule. Because the sample molecules may remain associated with the light couplers, the device may be reused by removing and discarding the couplers after detection. Because the sample molecule is carried by the coupler, it is unnecessary to modify the surface of the waveguide in order to directly link the sample molecule to the surface, thereby simplifying device manufacturing.

There is provided a system for detecting an object, such as a single-molecule object, wherein the detection system comprises a movable light coupler, a light detector, and a waveguide which comprises a core layer, a first cladding layer, and at least one adapter site for the movable light coupler formed in at least the first cladding layer. In some embodiments, the detection system comprises a light source.

In some embodiments, the movable light coupler is able to localize an object to the at least one adapter site formed in at least the first cladding layer of the waveguide, thereby localizing the object to be detected inside the space in which the confined excitation space and confined observable space overlap, i.e., a confined space suitable for single-molecule detection which is formed by docking of a movable light coupler to an adapter site. In some embodiments, the adapter site for the movable light coupler is a nanowell. In some embodiments, the movable light coupler is a nano-scale particle. In some embodiments, the movable light coupler is a nano-scale sphere.

As used herein, the terms "confined excitation space," "excitation space," and "excitation zone" all represent a space in which a fluorophore or other light-emitting object will be excited and emit light when entering.

As used herein, the terms "observable space" and "confined observable space" represent a space in which light emitted by a fluorophore or other light-emitting object located within that space can be detected by the detector.

As used herein, "confined space suitable for single-molecule detection" is used to signify a space in which excitation space and observable space overlap. When a single-molecule light emitting object is localized within the overlapping space, the object can be detected by the detector.

As used herein, "movable light coupler" refers to a movable object that can alter a behavior of excitation light, including, for example, the shape of the light's intensity field distribution, the light's direction of travel, and the light's wavelength.

"Adapter site," as used herein, refers to a space which is able to accommodate a movable light coupler.

The term "docking," as used in reference to a movable light coupler and an adapter site, refers to a movable light coupler fitting into an adapter site, thereby facilitating the formation of a confined space suitable for single-molecule detection.

In some embodiments, the movable light coupler is opaque to the excitation light, whereby the confined space suitable for single-molecule detection is formed by the movable light coupler blocking the excitation light from the waveguide from spreading to the bulk space. In some embodiments, the movable light coupler has a surface which is able to reflect excitation light, whereby the confined space suitable for single-molecule detection is formed in the region in which the movable light coupler reflects excitation light back toward the waveguide.

In some embodiments, the movable light coupler is transparent or partially transparent to excitation light, and placement of the movable light coupler at the adapter site formed in at least the first cladding layer of the waveguide allows an excitation zone to form around the surface of the movable light coupler from a light wave propagating along the core layer of the waveguide and coupling to the movable light coupler, wherein a confined space suitable for single-molecule detection is formed in the space between the movable light coupler and the adapter site. In some embodiments, the refraction index of the movable light coupler is selected to enhance the level of light coupling. In some embodiments, the movable light coupler is transparent or partially transparent to excitation light, and the placement of the movable light coupler at the adapter site formed in at least the first cladding layer of the waveguide allows an excitation zone to form around the surface of the movable light coupler from a light wave propagating along the core layer of the waveguide and coupling to the movable light coupler, thereby creating a confined space suitable for single-molecule detection around the surface of movable light coupler.

In some embodiments, the movable light coupler is able to absorb a first excitation light from the waveguide and then emit a second excitation light.

There is provided a method of detecting a single-molecule object, comprising the steps of a) introducing an incident light from a light source into a waveguide, thereby forming an excitation light in the waveguide, b) localizing a single-molecule object on the surface of a movable light coupler, c) localizing the movable light coupler of (b) at an adapter site for a movable light coupler formed in at least a first cladding layer of the waveguide, and d) exciting, by the excitation light, a single-molecule object localized on the movable light coupler, causing the single-molecule object to emit a light to be detected by a light detector. In some embodiments, localization of the movable light coupler at an adapter site for a movable light coupler formed in at least a first cladding layer of the waveguide forms a confined space suitable for single-molecule detection.

In some embodiments, methods of detecting a single-molecule object comprise localizing a movable light coupler at an adapter site in a specific orientation. In some embodiments, the methods comprise localizing a movable light coupler at an adapter site in a specific orientation by a magnetic field. In further embodiments, the light coupler is localized at an adapter site in a specific orientation by application of an electric potential across the adapter site. In some embodiments, the light coupler is localized at an adapter site in a specific orientation by introduction of one or more surface modifications at a light coupler adapter site which attract and/or repel surfaces of a light coupler.

There is provided a method of detecting a single-molecule object comprising the steps of a) providing a detection apparatus comprising (i) a movable light coupler, (ii) a waveguide comprising a core layer and a first cladding layer, wherein at least one adapter site for the movable light coupler is formed in at least the first cladding layer, and (iii) a light detector; b) providing at least one binding moiety capable of binding a single-molecule object; c) localizing the at least one binding moiety individually on the surface of the movable light coupler; d) providing a single-molecule object sample to one binding moiety localized on the movable coupler; e) localizing at the adapter site the movable light coupler on which the at least one binding moiety and single-molecule object are localized; f) introducing an incident light from a light source into the waveguide, thereby forming an excitation light in the waveguide; and g) exciting, by the excitation light, a single-molecule object bound to the at least one binding moiety localized on the movable light coupler, causing the single-molecule object to emit a light to be detected by a light detector. In some embodiments, localization at an adapter site of a movable light coupler on which the at least one binding moiety and single-molecule object are localized creates a confined space suitable for single-molecule detection, wherein the single-molecule object to be detected is localized within the confined space.

There is provided a method of sequencing a nucleic acid, comprising the steps of a) providing a detection apparatus comprising (i) a movable light coupler, (ii) a waveguide comprising a core layer and a first cladding layer, wherein at least one adapter site for the movable light coupler is formed in at least the first cladding layer, and (iii) a light detector; b) providing at least one nucleic acid molecule; c) localizing the at least one nucleic acid molecule individually on the movable light coupler; d) localizing at the adapter site the movable light coupler on which at least one nucleic acid is localized; e) performing single molecule sequencing-by-synthesis of the at least one nucleic acid molecule, wherein the single molecule nucleic acid sequencing-by-synthesis produces an emitted light correlated to the identity of at least one base in the nucleic acid; f) detecting the emitted light with the detector, resulting in an output signal; and g) processing the output signal to determine an identity of at least one base comprised by the nucleic acid.

A detection system may be used as part of a system for or in methods and processes of biomolecule detection, including nucleic acid hybridization or sequencing for, e.g., whole-genome sequencing, transcriptional profiling, comparative transcriptional profiling, or gene identification. Biomolecule detection can also include detection and/or measurement of binding interactions, e.g., protein/protein, antibody/antigen, receptor/ligand, and nucleic acid/protein. These applications are useful for analytical or diagnostic processes and methods Hereinafter, embodiments will be described in detail with reference to drawings. Wherever possible, the same reference numbers will be used throughout the drawings to refer to the same or like parts.

1. DETECTION SYSTEM

A detection system described herein can detect an object, such as a single-molecule object. The object may be a source of luminescence, such as a fluorescent dye molecule, a phosphorescent dye molecule, a quantum dot, or a light-emitting nanoparticle. The object may also be a light-scattering particle. In addition, the object may be a target molecule without light-emitting capability, but may be attached to a labeling object which is capable of emitting light (e.g., a fluorescent dye molecule, a phosphorescent dye molecule, or a quantum dot). A certain labeling object may be capable of being attached to a specific target molecule. Thus, the target molecule may be identified via the labeling object. More than one labeling object may be attached to one target molecule. The object may be a target molecule that does not have light-emitting capability and is attached to multiple labeling objects which are capable of emitting light in a sequential order. (e.g., FRET, wherein light of a first wavelength is emitted from at least a first excited fluorescent molecule and is at least partially absorbed by a second fluorescent molecule, which in turns emits a second light, i.e., emitted light of a second wavelength).

1.1 Overview of the Detection System

The detection system may comprise a movable light coupler, a detector, and a waveguide, wherein the waveguide comprises an adapter site for the movable light coupler.

The detection system may further comprise at least one light source, which can emit a light, which may then be at least partially coupled into the waveguide as an excitation light to excite the object. The light source may be, for example, laser such as He—Ne laser and laser diode (LD), light emitting diode (LED), organic light emitting diode (OLED), quantum dot light emitting diode (QLED), fiber light, or arc discharge fluorescent lamp. The detection system may comprise a light source coupler. The light source coupler may couple at least part of the light emitted from the at least one light source into the waveguide. The light source coupler may be, e.g., a prism coupler, a grating coupler, a side-injection coupler, a vertical-injection coupler, or a co-directional coupler.

The waveguide may be a channel waveguide or a planar waveguide. The waveguide may comprise a core layer and at least one cladding layer. For example, if the waveguide is a channel waveguide, it may comprise a core layer and a cladding layer surrounding the core layer. As another example, if the waveguide is a planar waveguide, it may comprise a core layer and one cladding layer arranged on the core layer or two cladding layers sandwiching the core layer. The core layer may have a higher refractive index than the at least one cladding layer. The excitation light may propagate in the core layer of the waveguide. Exemplary waveguides and specific features thereof suitable for use in the detection system are described in U.S. patent application Ser. No. 12/720,352, filed Mar. 9, 2010; U.S. patent application Ser. No. 12/801,503, filed Jun. 11, 2010; and U.S. patent application Ser. No. 12/805,411, filed Jul. 29, 2010, each of which is incorporated herein by reference in its entirety.

The detection system may comprise a waveguide comprising at least one adapter site for a movable light coupler. The adapter site may be formed in at least the at least one cladding layer of the waveguide. The adapter site may be a nanowell comprising an upper opening and a bottom surface, wherein the upper opening may be larger than the bottom surface. The nanowell may extend through partial thickness of the at least one cladding layer, full thickness of the at least one cladding layer, full thickness of the at least one cladding layer and partial thickness of the core layer, or the full thickness of the at least one cladding layer and full thickness of the core layer. The lower boundary of the effective excitation zone may be the bottom of the nanowell. The upper boundary of the effective excitation zone may be defined by the distance to which the excitation light can reach in the nanowell adapter site in the direction perpendicular to the longitudinal direction of the core layer (hereinafter, vertical direction).

Embodiments of the detection system encompass a movable light coupler which is able to localize a single-molecule object to the at least one adapter site of the waveguide. The movable light coupler may be a nano-scale particle. The movable light coupler may be a nano-scale sphere or a nonspheroidal nano-scale particle. When a movable light coupler docks at an adapter site in the waveguide, a confined excitation space suitable for single-molecule detection (an effective excitation space) may then form, and the object to be detected may be localized within the confined space. When a movable light coupler docks at an adapter site, it may prevent a second movable light coupler from docking at the same adapter site.

The movable light coupler may comprise at least one property by which the light coupler may be attracted to the adapter site, including, for example, a surface property or a magnetic property to facilitate docking. In some embodiments, the light coupler comprises at least one property by which the light coupler may be localized at the at least one adapter site in a specific orientation. Suitable properties by which the light coupler may be localized at the at least one adapter site in a specific orientation may include asymmetric surface properties. In some embodiments, the light coupler can localize a single-molecule object in a confined space near the surface of the core layer of the waveguide within the adapter site, wherein an object is localized in an effective excitation zone formed within the adapter site from a light field induced by a light wave propagating along the core layer of the waveguide.

The core layer of the waveguide may have a higher refractive index than the at least first cladding layer of the waveguide. In some embodiments, the movable light coupler is made from a material having a refractive index substantially similar to the refractive index of a surrounding solution or of the material of the at least first cladding layer of the waveguide. In further embodiments, the movable light coupler is made from a material having a refractive index that is greater than the refractive index of the at least first cladding layer of the waveguide. In some embodiments, the movable light coupler is made from a material having a refractive index that is substantially similar or equivalent to that of the core layer of the waveguide. In some embodiments, the light coupler is able to couple an evanescent light field induced by a light wave propagating along the core layer, whereby an effective excitation zone forms around the surface of the light coupler.

In some embodiments, the movable light coupler is opaque and can confine excitation light at its surface, whereby the confined space suitable for single-molecule detection is formed by the movable light coupler blocking the excitation light from the waveguide from spreading to the bulk space. In some embodiments, the movable light coupler is reflective to light. In some embodiments, the movable light coupler is reflective to excitation light. In some embodiments, the movable light coupler is able to absorb excitation light emitted by the waveguide and then itself emit a light which is able to excite molecules to be detected.

The waveguide component of the detection system may comprise a plurality of adapter sites. Therefore, the system may also be used to monitor a large number of objects.

The detection system may comprise a light detector detecting light emitted from the object. The light detector may comprise an optical sensor, which is capable of at least partially absorbing light incident thereon and generating output signals in response to the light. The optical sensor may be, e.g., a p-n photodiode, a p-i-n photodiode, a multi-junction photodiode, an avalanche photodiode (APD), a phototransistor, a quantum-well infrared photodetector (QWIP), a photoconductive type optical sensor, a photovoltaic type optical sensor, a thin-film on ASIC (TFA), a metal-semiconductor-metal (MSM) photodetector, a charge coupled device (CCD), a CMOS sensor, or a combination thereof.

In some embodiments, the light detector comprises a control circuit for controlling the operation of the light detector. The control circuit may comprise a circuit of signal amplifier, A/D convertor, integrator, comparator, logic circuit, readout circuit, memory, microprocessor, clock, and/or address.

The light detector may be arranged at a place that the light emitted from the object can reach. For example, the light detector may be arranged at the opposite side of the core layer with respect to the adapter site. That is, if the adapter site is arranged on one side of the core layer in the vertical direction, the light detector may then be arranged on the other side of the core layer in the vertical direction. The detection system may further comprise at least one filter between the core layer and the detector.

A schematic view of an exemplary detection system is illustrated in FIG. 1. The detection system may comprise a movable light coupler 100 and an integrated component comprising a planar waveguide 110, a detector 102, and an adapter site 104 for a movable light coupler, whereby the adapter site is accessible to a movable light coupler 100 and a surrounding sample solution 120. The waveguide 110 may comprise a core layer 112, an upper cladding layer 114, and a lower cladding layer 116. The planar waveguide 110 may be formed on a substrate (not shown). The light detector 102 may be formed on or in the substrate. A light source 130 may emit a light 135, which may be at least partially coupled into the planar waveguide 110 by a light source coupler 140. Light coupled into the planar waveguide 110 may propagate along the core layer of the planar waveguide 110 and serve as the excitation light 145.

Figure 2:
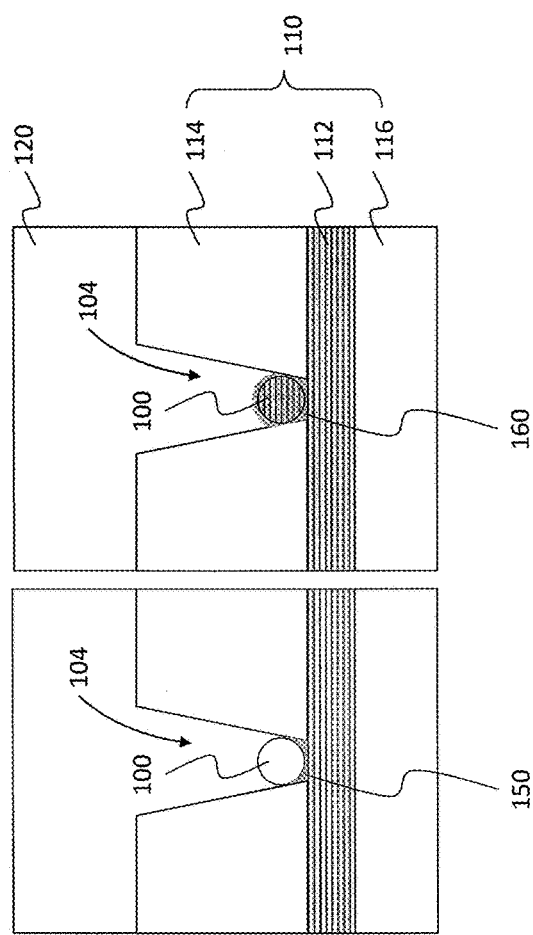
FIG. 2 shows two schematic views of detection systems according to some embodiments.

A schematic view of an exemplary detection system is illustrated in each panel of FIG. 2. In some embodiments, the movable light coupler 100 is made of a material having a refractive index that is closer to the refractive index of a surrounding sample solution 120 or of the at least first cladding layer 114 of the waveguide than to the refractive index of the material of the core layer 112. In such embodiments, a light wave propagating along the core layer of the waveguide from a light source (not shown) may induce an evanescent light field near the surface of the core layer within the adapter site, thereby forming an effective excitation zone 150 in the confined space at the bottom of the adapter site (left panel). In further embodiments, the movable light coupler is made from a material having a refractive index that is greater than the refractive index of the at least first cladding layer of the waveguide and/or that is substantially similar or equivalent to the refractive index of the core layer of the waveguide. In such embodiments, the light coupler may couple an evanescent light field induced near the surface of the core layer in the adapter site by a light wave propagating along the core layer of the waveguide from a light source (not shown), thereby forming an effective excitation zone 160 in the confined space between the movable light coupler and the core layer of the waveguide and around the surface of the light coupler (right panel).

1.2 Components of Detection System 1.2.1 Waveguide

As shown in FIG. 1, in some embodiments, the planar waveguide 110 may comprise a core layer 112, an upper cladding layer 114, and a lower cladding layer 116. The core layer 112 may comprise a material having a refractive index of $n_2$, such as silicon-titanium oxide ($Si_xTi_{1-x}O_2$, where 0<x<1), titanium oxide, tantalum oxide, niobium oxide, hafnium oxide, aluminum oxide, zirconium oxide, silicon nitride, aluminum nitride, titanium nitride, polycarbonate (PC), PMMA, or Su8. The upper and lower cladding layers 114 and 116 may comprise materials having a refractive index of $n_3$ and $n_4$, respectively. The materials for the upper and lower cladding layers 114 and 116 may be the same or may be different. Suitable material for the upper cladding layer 114 or the lower cladding layer 116 may comprise, for example, silicon oxide, magnesium fluoride, calcium fluoride, aluminum oxide, Su8, PMMA, or polycarbonate. The refractive index $n_2$ of the core layer 112 may be higher than the refractive indices $n_3$ and $n_4$ of the upper and lower cladding layers 114 and 116.

For single-molecule detection, one may need to prevent the excitation light from reaching the detector. In a planar waveguide, the surface of the core layer may not be as smooth as would be desired. The rough surface of the core layer may scatter part of the excitation light. It has been estimated that, for a core layer having a surface roughness of about 0.3 nm, about 0.01% excitation light may be scattered and produce the noise. In order to reduce the noise coming from surface scattering of excitation light propagating within the core, an excitation light filter may be added between the waveguide and detector to reduce the amount of scattered excitation light reaching the detector. In some embodiments, the filter is a multilayer interference filter. In some embodiments, the filter is a layer made of material that can absorb excitation light.

In some embodiments, protection layer(s) may be included in the detection system to absorb scattered excitation light and/or to block the ambient light from outside the detection system, so as to increase the signal-to-noise (S/N) ratio, as described in U.S. application Ser. No. 12/801,503, filed Jun. 11, 2010, and in U.S. patent application Ser. No. 12/805,411, filed Jul. 29, 2010. A protection layer may be formed over an upper cladding layer, and/or a lower protection layer may be formed under a lower cladding layer. In some embodiments, a protection layer is made of an opaque material, such as metal or alloy. In some embodiments, a pinhole may be formed in a lower protection layer at a position below the adapter site. Light emitted from an object in the effective excitation zone in the adapter site may pass through the pinhole and be detected by a light detector below the lower protective layer.

1.2.2 Adapter Site

As exemplified if FIG. 1 and FIG. 2, at least one movable light coupler adapter site 104 may be formed in at least the upper cladding layer 114 of the waveguide. The adapter site may be a nanowell. The upper opening of the nanowell may be larger than the bottom of the nanowell. The shape of the nanowell is not limited. For example, the horizontal cross section of the nanowell may have a circular shape, an oval shape, a rectangular shape, a square shape, or a diamond shape. The size of the bottom of the nanowell adapter site is also not limited. For example, the size of the bottom of the nanowell may be smaller than about the wavelength of the excitation light. In some embodiments, the size of the bottom of the nanowell may be smaller than about one-half, about one-quarter, or about one-eighth of the wavelength of the excitation light. As used herein, "size" may refer to diameter, length of the long axis, or length of the long side if the horizontal cross section of the nanowell has a circular shape, an oval shape, or a rectangular shape. If the horizontal cross section of the nanowell has a square or a diamond shape, "size" may refer to the length of the side. In one embodiment, the length (namely the diameter, length of the long axis, or length of the long side) of the upper opening of the nanowell may be about 1 to about 10 μm and the diameter of the bottom of the nanowell may be about 10 to about 500 nm, the angle of the sidewall of the nanowell relative to the direction perpendicular to the bottom of the nanowell may be less than about 60 degrees. Such a configuration may ensure that only one single movable light coupler can enter a region near the bottom of the nanowell.

Part of the excitation light may enter the adapter site 104 and may, together with the spatial confinement of the adapter site 104, form an effective excitation zone 150 in at least a portion of the adapter site, as exemplified in FIG. 1 and FIG. 2. It is to be understood that reference number 150 in FIG. 1 indicates an approximate upper boundary of the effective excitation zone. When an object enters the effective excitation zone 150, it may be excited by the excitation light and emit a light to be detected by the light detector 102. Outside the effective excitation zone 150, an object may not be excited by the excitation light, or its emitted light cannot reach the light detector. It is to be understood that, the dashed line in FIG. 1 does not limit the shape of the upper boundary of the effective excitation zone. For example, the upper boundary of an effective excitation zone may be in a curved shape.

Depending on different conditions, such as the position of the nanowell and/or the depth of the nanowell extending in the waveguide, a different effective excitation zone may be formed. In addition, the electromagnetic field in the effective excitation zone may be, for example, an evanescent field, a mixture of evanescent and travelling fields, or a travelling field, as described in more detail below.

Figure 3:
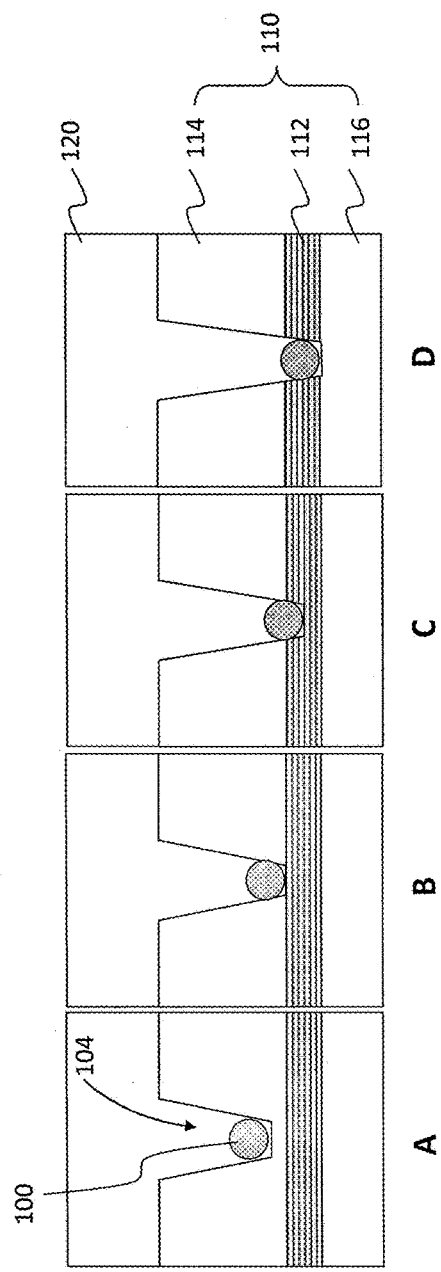
FIG. 3 is a schematic view showing different adapter site designs consistent with certain embodiments.

FIG. 3 schematically shows, as examples, embodiments with different nanowell adapter site designs. In some embodiments, a nanowell adapter site may extend through partial thickness of the upper cladding layer (panel A). In some embodiments, a nanowell adapter site may extend through full thickness of the upper cladding layer (panel B). For nanowells as shown in panels A or B, when the excitation light propagates in the core layer, although there may not be a travelling light field component in the nanowell, part of the light travelling in the core layer may penetrate slightly into the nanowell. The light penetrating into the nanowell may decay exponentially in the vertical direction, forming an evanescent field. This evanescent field, together with the spatial confinement of the nanowell, may form an effective excitation zone in at least a portion of the nanowell near the core layer.

In some embodiments, a nanowell may extend through the full thickness of the upper cladding layer and partial thickness of the core layer (FIG. 3; panel C). In such an embodiment, a travelling field component may appear in the nanowell, and together with an evanescent field, form an effective excitation zone in the nanowell.

In some embodiments, a nanowell may extend through full thickness of the upper cladding layer and full thickness of the core layer (FIG. 3, panel D). In such an embodiment, most of the electromagnetic field forming an excitation zone in the nanowell may be a travelling field.

For a planar waveguide comprising a nanowell as depicted in FIG. 3, panel B, because the bottom end of the nanowell is located on the upper surface of the core layer, the volume of the effective excitation zone may be equal to the effective region of the evanescent field, and may be calculated approximately using the following equation:

$$V = \pi \times (D/2)^2 \times h$$

where D is the diameter of the bottom of the nanowell and h is the penetration depth of the evanescent field in the nanowell. For example, if D and h are 100 nm and 100 nm, respectively, the calculated volume of the effective excitation zone is approximately $1 \times 10^{18}$ liter (1 attoliter).

In some embodiments, a plurality of adapter sites may be formed in the waveguide. In some embodiments, for each of the plurality of adapter sites, a light detector may be formed to detect the light emitted from an object in the effective excitation zone of the adapter site. In some embodiments, one light detector may be used to detect the light emitted from objects in the effective excitation zones of a plurality of adapter sites.

1.2.3 Movable Light Coupler

Embodiments encompass a movable light coupler that may be capable of localizing a single-molecule object at an adapter site formed in at least a first cladding layer of a waveguide. The movable light coupler may localize on its surface at least one binding moiety capable of binding a single-molecule object to be detected. A binding moiety may be a single molecule or molecular complex (e.g., a receptor, an antibody, an enzyme, or a multimeric complex such as a reaction complex comprising an enzyme) which is capable of binding the object. A single-molecule object to be detected may bind to the binding moiety localized on the surface of a movable light coupler which is positioned at an adapter site, thereby localizing the object, via the binding moiety and light coupler, in a confined space for effective signal excitation and observation. The movable light coupler may have only one binding moiety localized on its surface, such that if binding of the single-molecule object to the surface-localized binding moiety is detected, the number of objects detected at any given moment may be no greater than the number of objects that can simultaneously bind to the binding moiety. Thus, where a binding moiety binds only one object at a time, the detection system can detect a single object binding to the binding moiety localized on the surface of the movable light coupler.

An object that is "localized" on the surface of a movable light coupler, as used herein, includes an object that is nonspecifically adsorbed on the surface of a movable light coupler and an object that is tethered to the surface of a movable light coupler via one or more covalent linkages or via noncovalent interactions.

In some embodiments, the movable light coupler is a nano-scale particle. In some embodiments, the light coupler is a nano-scale sphere. The nano-scale sphere may have a diameter of from about 40 nm to 1000 nm or from about 1/10 to twice the wavelength of the excitation light. The size of the nano-scale sphere may be decided in accordance with the size of the light detector. For example, the size of the nano-scale sphere may be chosen such that a single light detector is only capable of detecting the light emanating from only one sphere. In some embodiments, the size of the nano-scale sphere and the shape of the adapter site are chosen such that the nanosphere may be positioned at the adapter site at a distance of between about 10 nm and 200 nm from the bottom surface of the adapter site. In further embodiments, the light coupler is a nonspheroidal nano-scale particle. In some embodiments, the nano-scale particle is a bar-like particle. The "length" of a movable light coupler particle refers to the distance from one end of the light coupler to the opposite end at the widest point of the light coupler. For example, the length of a spherical light coupler corresponds to its diameter, and the length of a bar-like particle is the distance between the far ends of the bar.

The movable light coupler may be a homogenous solid, a colloidal or porous solid, or a solid composed of a material with a polymer backbone. In some embodiments, the multifunctional movable light coupler comprises one or more metal materials, including, for example, gold (Au), silver (Ag), copper (Cu), platinum (Pt), nickel (Ni), chromium (Cr), or a metal alloy. In some embodiments, the light coupler comprises one or more oxide materials, including, for example $TiO_2$, $Ta_2O_5$, $Nb_2O_5$, $SiO_2$, $HfO_2$, $Al_2O_3$, $ZrO_2$, ZnO, $V_2O_5$, $CeO_2$, CdO, $Fe_2O_3$, $Fe_3O_4$, $Cu_2O$, CuO, $In_2O_3$, $La_2O_3$, $MoO_3$, or $WO_3$. In further embodiments, the light coupler comprises one or more sulfide materials, including, for example, CdS, ZnS, PbS, $Au_2S$, or $Ag_2S$. In some embodiments, the light coupler comprises one or more selenide materials, including, for example, CdSe, ZnSe, or PbSe. In some embodiments, the light coupler comprises one or more nitride materials, including, for example, $Si_3N_4$, TiN, BN, and GaN. In further embodiments, the light coupler comprises one or more polymer materials, including, for example, polystyrene, a polyethyleneimine, a polyphosphazene, polylactide, polylactide-co-glycolide, polycaprolactone, a polyanhydride, polymaleic acid and its derivatives, polyalkylcyanoacrylate, polyanhydride oxybutyrate, polycarbonate, polyorthoester, polyethylene glycol, poly-L-lysine, polyglycolide, polymethylmethacrylate, polyvinylpyrrolidone, or copolymers thereof.

In some embodiments, the movable light coupler has a core-shell nanostructure. The core material may comprise one or more metal materials, including, for example, gold (Au), silver (Ag), copper (Cu), platinum (Pt), nickel (Ni), chromium (Cr), or a metal alloy. In some embodiments, the core material comprises one or more oxide materials, including, for example $TiO_2$, $Ta_2O_5$, $Nb_2O_5$, $SiO_2$, $HfO_2$, $Al_2O_3$, $ZrO_2$, $ZnO$, $V_2O_5$, $CeO_2$, $CdO$, $Fe_2O_3$, $Fe_3O_4$, $Cu_2O$, $CuO$, $In_2O_3$, $La_2O_3$, $MoO_3$, or $WO_3$. In some embodiments, the core material comprises one or more sulfide materials, including, for example, CdS, ZnS, PbS, $Au_2S$, or $Ag_2S$. In further embodiments, the core material comprises one or more selenide materials, including, for example, CdSe, ZnSe, or PbSe. In some embodiments, the core material comprises one or more nitride materials, including, for example, SiN or GaN. In further embodiments, the core material comprises one or more polymer materials, including, for example, polystyrene, a polyethyleneimine, a polyphosphazene, polylactide, polylactide-co-glycolide, polycaprolactone, a polyanhydride, polymaleic acid and its derivatives, polyalkylcyanoacrylate, polyanhydride oxybutyrate, polycarbonate, polyorthoester, polyethylene glycol, poly-L-lysine, polyglycolide, polymethylmethacrylate, polyvinylpyrrolidone, or copolymers thereof.

The shell of a core-shell nanostructure light coupler may comprise one or more metal materials, including, for example, gold (Au), silver (Ag), copper (Cu), platinum (Pt), nickel (Ni), chromium (Cr), or a metal alloy. In some embodiments, the shell material comprises one or more oxide materials, including, for example $TiO_2$, $Ta_2O_5$, $Nb_2O_5$, $SiO_2$, $HfO_2$, $Al_2O_3$, $ZrO_2$, $ZnO$, $V_2O_5$, $CeO_2$, $CdO$, $Fe_2O_3$, $Fe_3O_4$, $Cu_2O$, $CuO$, $In_2O_3$, $La_2O_3$, $MoO_3$, or $WO_3$. In some embodiments, the shell material comprises one or more sulfide materials, including, for example, CdS, ZnS, PbS, $Au_2S$, or $Ag_2S$. In further embodiments, the shell material comprises one or more selenide materials, including, for example, CdSe, ZnSe, or PbSe. In some embodiments, the shell material comprises one or more nitride materials, including, for example, SiN or GaN. In further embodiments, the shell material comprises one or more polymer materials, including, for example, polystyrene, a polyethyleneimine, a polyphosphazene, polylactide, polylactide-co-glycolide, polycaprolactone, a polyanhydride, polymaleic acid and its derivatives, polyalkylcyanoacrylate, polyanhydride oxybutyrate, polycarbonate, polyorthoester, polyethylene glycol, poly-L-lysine, polyglycolide, polymethylmethacrylate, polyvinylpyrrolidone, or copolymers thereof.

In some embodiments, the movable light coupler is made from a material having a refractive index that is closer to the refractive index of the material of the first cladding layer of the waveguide than to the refractive index of the material of the core layer of the waveguide. In some embodiments, the movable light coupler is made from a material having a refractive index that is closer to the refractive index of a surrounding sample solution than to the refractive index of the material of the core layer of the waveguide. In some embodiments, the movable light coupler is made from a material having a refractive index that is intermediate between the refractive index of the first cladding layer of the waveguide and the refractive index of the core layer of the waveguide. In further embodiments, the light coupler is made from a material having a refractive index that is substantially similar to the refractive index of the core layer of the waveguide. In some embodiments, the light coupler is made from a material having a refractive index that is equivalent to the refractive index of the core layer.

In some embodiments, the movable light coupler is composed of $SiO_2$, having a refractive index of 1.487. In some embodiments, the movable light coupler is composed of polystyrene, having a refractive index of 1.59. In further embodiments, the light coupler is composed of $TiO_2$, having a refractive index of 2.0. In some embodiments, the light coupler is composed of $Fe_3O_4$, having a refractive index of 2.4. In still further embodiments, the light coupler is composed of $Ta_2O_5$, having a refractive index of 2.26.

In some embodiments, the light coupler has a core-shell structure, wherein the shell material is gold (Au), having a refractive index of 1.28. In some embodiments, the shell material is silver (Ag), having a refractive index of 0.135. In further embodiments, the shell material is platinum (Pt), having a refractive index of 1.9. In some embodiments, the shell material is aluminum (Al), having a refractive index of 0.714. In still further embodiments, the shell material is cobalt (Co), having a refractive index of 1.86. In some embodiments, the shell material is nickel (Ni), having a refractive index of 1.66.

In some embodiments, the movable light coupler has an appropriate size and a refractive index sufficiently similar to the refractive index of the material of the core layer of the waveguide such that the light coupler is able to couple light from a waveguide when placed at an adapter site in the waveguide. In such embodiments, an induced light field may form around the surface of the movable light coupler, thereby forming an effective excitation zone around the light coupler, wherein a molecule can be excited to emit fluorescent light within a certain distance of the surface of the light coupler.

The intensity of the excitation light field induced around the surface of the movable light coupler may be controlled by tuning the optical waveguide's electric field in the surrounding environment, by selecting appropriate characteristics (e.g., material composition, shape, and size) for the light coupler, and by configuring the shape of the adapter site. In embodiments in which the movable light coupler is a sphere, the intensity of the excitation light field at the surface of the light coupler can be calculated with the following formula:

$$P = 1 - \frac{\left(\frac{I_{max}}{I_i}\right)}{1 + \left(\frac{2\Im}{\pi}\right)^2 \sin^2\left(\frac{\theta}{2}\right)}, \quad \text{(equation 1)}$$

where P is the optical power of the excitation light field on the sphere surface, $\Im$ (Finesse) is determined by the equation $$\Im = \frac{\pi\sqrt{r}}{(1-r)},$$

r is determined by the equation $$r = \sqrt{(1-\kappa)\exp(-\pi R\alpha_{ring})},$$

$I_{max}/I_i$ is determined by the equation $$\frac{I_{max}}{I_i} = \frac{\kappa[1-\exp(-2\pi R\alpha_{ring})]}{\left[1-\sqrt{(1-\kappa)}\exp(-\pi R\alpha_{ring})\right]^2},$$

θ is determined by the equation $$\theta = N_{ring}k_0 2\pi R,$$

and where R is the radius of the curvature of the sphere, $\alpha_{ring}$ is the sphere's mode power decay coefficient, $N_{ring}$ is the sphere's equilibrium refractive index, κ is the power coupling coefficient, and $k_0=2\pi/\lambda_0$ (where $\lambda_0$ is the free-space wavelength. In a resonance situation, where the light energy will transfer completely into the spherical light coupler, $N_{ring}k_0 2\pi R=2m\pi$, where m is an integer, $\kappa=1-\exp(-2\pi R_1\alpha_{ring})$ (where $R_1$ is the outer bending radius), and P=1. The term "critical coupling" is used herein to describe this resonance situation.

In some embodiments, an optical property of the light coupler changes when the light coupler is surrounded by certain molecules within a specific range. In some embodiments, the optical property that changes when the light coupler is surrounded by certain molecules within a specific range is refractive index, light-absorbing capability, the wavelength of light absorbed by the coupler, or the direction of light propagating through the light coupler.

Figure 4:
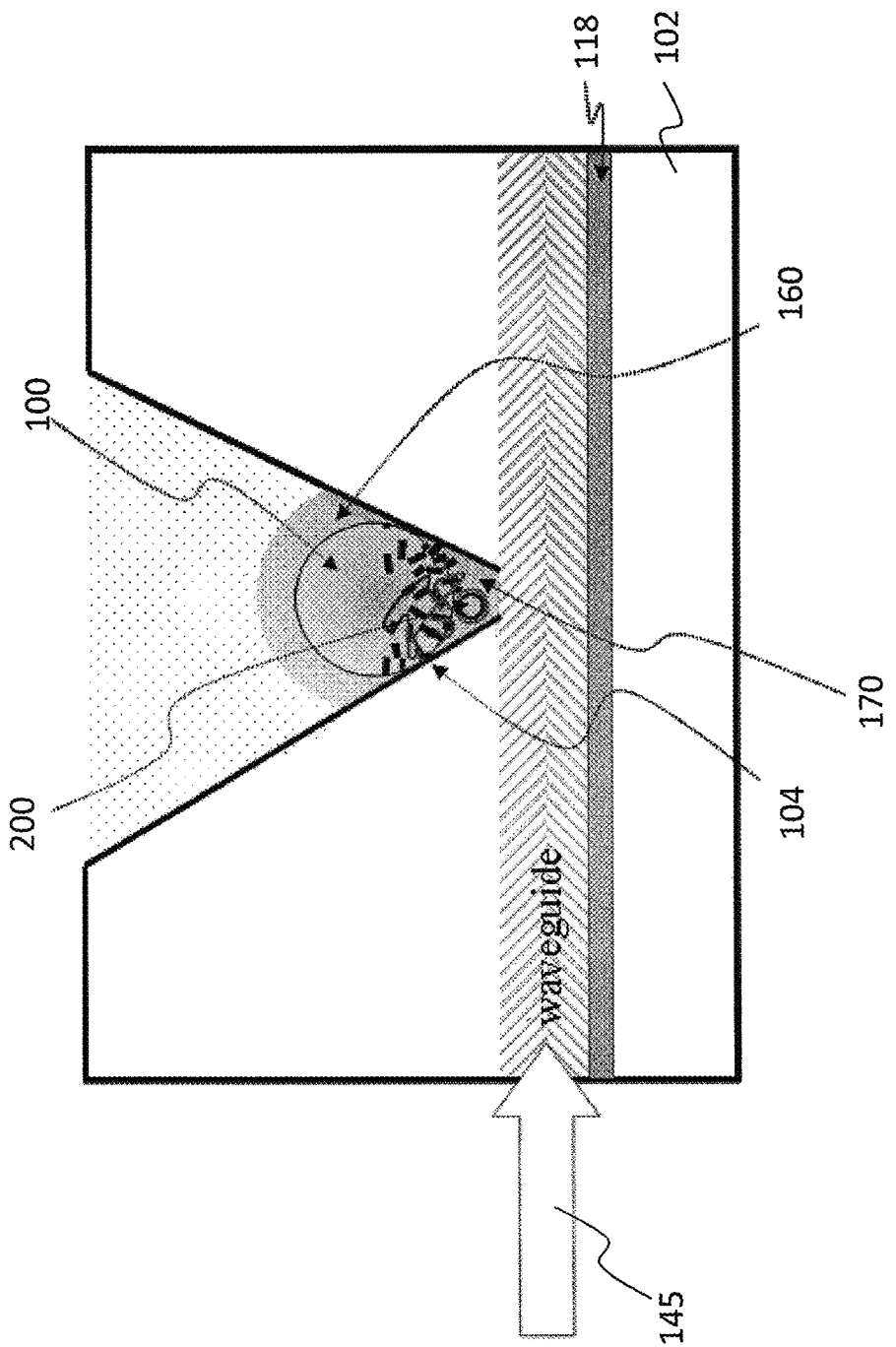
FIG. 4 is a schematic view showing a detection system according to certain embodiments.

In some embodiments, one or more regions of the surface of the movable light coupler are modified. For example, the entire surface of nano-scale sphere light coupler may be modified. Surface modification is distinct from the shell material of a light coupler with a core-shell structure, i.e., a core-shell light coupler comprising surface modification has modification of the outside surface of the shell material. In a further example, the surface of one hemisphere of a nano-scale sphere light coupler may be modified while the remaining hemisphere is unmodified. The surface of the light coupler may be coated over its entire surface or at least a portion of its surface with one or more heterogeneous materials by chemical modification techniques. A surface modification may serve to localize the movable light coupler at an adapter site. Asymmetric surface modification, e.g., modification on one surface only, or different modification on opposite surfaces, may serve to localize the movable light coupler at an adapter site in a specific orientation. A surface modification may also serve to localize a single-molecule object at a particular region of the surface of the light coupler, whereby such a region may be oriented to face the core layer of the waveguide, thereby localizing the object and any reaction involving the object in a confined space between the movable light coupler and the surface of the adapter site near the core layer of the waveguide. A schematic illustration of an exemplary detection system comprising a nano-scale sphere light coupler particle which is modified on one hemisphere with oligonucleotide primers is shown in FIG. 4. The nano-scale sphere light coupler 100 is modified on one half of its surface with oligonucleotide primers capable of hybridizing to sequences embedded in a replicating DNA strand of a DNA synthesizing reaction complex 200. Positioning of the light coupler 100 at the adapter site 104 with the oligonucleotide-modified surface of the light coupler facing the core layer of the waveguide localizes the reaction complex 200 in the confined space 170 in the bottom of the nanowell adapter site 104.

In some embodiments, the modification of one or more regions of the surface of the movable light coupler is chemical modification. In some embodiments, the chemical modification is covalent linkage of a functional group to the surface of the light coupler. A covalently-linked functional group may be a hydrophobic group or a hydrophilic group. Suitable hydrophobic groups include, for example, —$C_x(H_2)_xCH_3$, —$C_6H_6$, an epoxy group, —$Si(C_xH_{x+1})_2$ (derived from a compound having the formula $H_3$—$Si(C_xH_{x+1})_2$, such as N-octylsilane), —O—$Si(C_xH_{x+1})_2$ (derived from a compound having the formula $R_3$—O—$Si(C_xH_{x+1})_2$, such as trimethoxy(octyl)silane), and the like. In some embodiments, the light coupler is a homogenous solid particle composed of a metal material or is a core-shell particle comprising a metal shell material, and a hydrophobic group is covalently linked to the metal material via a sulfur, an amine, carboxyl, or phosphate linkage. In some embodiments, the light coupler is a homogenous solid particle composed of a metal oxide or $SiO_2$ material or is a core-shell particle comprising a metal oxide or $SiO_2$ shell material, and a hydrophobic group R is covalently linked as a —Si—R group to the oxygen atoms of the metal oxide or $SiO_2$ material. In some embodiments, the covalently-linked functional group is a hydrophilic group, including, for example, —$NH_2$, —OH, —$CO_2H$, —$OSO_3H$. For example, in some embodiments, the light coupler is a homogenous solid particle composed of a metal oxide or $SiO_2$ material or is a core-shell particle comprising a metal oxide or $SiO_2$ shell material, and an —OH group is covalently linked to the metal oxide or $SiO_2$ material. Suitable hydrophilic groups further include charged groups, including, for example, positively-charged groups such as —$NH_3^+$, or negatively-charged groups such as —$CO_2^-$ or —$OSO_3^-$. In some embodiments, a covalently-linked functional group is a magnetic functional group. Suitable magnetic groups include, for example, —$Fe_3O_4$, —$Fe_2O_3$, —FePt, —FeNi, —FeCo, —Mg, —Co, —Ni, and the like. In some embodiments, a covalently-linked functional group is a fluorescent functional group. Suitable fluorescent groups include, for example, molecular dyes such as -FITC, -Rhodamine 6G (-Rh6G), -Cy3, and -Cy5, and the like, and nanoparticles/quantum dots, such as —CdSe, —ZnS, —PbS, —PbSe, and the like. In some embodiments, a surface of the movable light coupler is covalently modified with biotin, streptavidin, avidin, or the like.

In further embodiments, the chemical modification is a noncovalent modification. The noncovalent modification may be a coating with a polymer material. In some embodiments, for example, the light coupler is a homogenous solid particle composed of a metal material or is a core-shell particle comprising a metal shell material, and a surface of the light coupler is coated with a hydrophilic polymer, such as polyethylene glycol (PEG).

In some embodiments, only one region of the surface of the movable light coupler is modified, while the remainder of the surface of the light coupler is unmodified. In some embodiments, the modified region of the surface of the movable light coupler is from about 10 to 90% of the surface of the movable light coupler. "About 10 to 90% of the surface of the movable light coupler" as used to describe such embodiments is meant to signify that the modified region of the surface of the movable light coupler may be anywhere from slightly less than 10% to slightly more than 90% of the surface of the light coupler. In further embodiments, the modified region of the surface of the light coupler is less than 10% of the surface of the light coupler. In yet further embodiments, the modified region of the surface of the light coupler is more than 90% of the surface of the light coupler.

In some embodiments, two regions of the surface of the movable light coupler are modified, as schematized in FIG. 5A, showing modified surface 1 and modified surface 2. In some embodiments, the light coupler comprises two regions of surface modification with functional groups or coatings having opposing properties. For example, one surface of the light coupler may be modified to have a hydrophobic surface character, while the opposite surface may be modified to have a hydrophilic surface character. In further embodiments, one surface of the light coupler is modified with a positively-charged group, while the opposite surface is modified with a negatively-charged group. In some embodiments, one surface of the light coupler is modified to attract and retain DNA, e.g., the surface is modified with a positively-charged functional group or is modified with an oligonucleotide capable of hybridizing to sequences in a target DNA molecule, while the other surface of the light coupler does not attract DNA.

In further embodiments, the movable light coupler comprises two regions of surface modification with functional groups or coatings have different types of properties. For example, in some embodiments, one region of the surface of a movable light coupler is modified with a magnetic functional group, while the opposite surface of the movable light coupler is modified with a fluorescent functional group.

In some embodiments, the surface of an adapter site formed in at least the first cladding layer of a waveguide comprises one or more surface modifications. The waveguide may comprise a first cladding layer and a second cladding layer, as schematized in FIG. 5B, wherein the first (lower) cladding layer and a surface of the core layer (not shown) at the bottom of the adapter site comprise a surface modification 3 that attracts surface modification 1 on the movable light coupler 100 and/or that repels surface modification 2 on the movable light coupler 100, and wherein the second (upper) cladding layer comprises a surface modification 4 that is compatible with surface modification 2 on the movable light coupler 100. The waveguide may comprise a first cladding layer that comprises both surface modifications 3 (together with a surface of the core layer at the bottom of the adapter site) and 4, as schematized in FIG. 6, wherein surface modification 3 attracts surface modification 1 on the movable light coupler 100 and/or repels surface modification 2 on the movable light coupler 100, and wherein surface modification 4 is compatible with surface modification 2 on the movable light coupler 100. For example, surface modifications 1 and 3 schematized in FIG. 5 and FIG. 6 may be hydrophilic in nature, while surface modifications 2 and 4 are hydrophobic in nature. In some embodiments, surface 3 of the adapter site 104 is hydrophilic, comprising a member chosen from silicon, silica, metal, or metal oxide, and surface 4 is hydrophobic. However, if a surface of the adapter site 104 is made of a material with hydrophilic property, it may be modified to be hydrophobic. For example, if a surface of the adapter site 104 is made of silicate or metal with a hydrophilic nature, it may be modified to be hydrophobic using, for example, $R1_x$-Si$(O-R2)_{4-x}$ (where R1 is a hydrophobic group, such as alkyl chain $-(CH_2)_n-CH_3$, and R2 is $C_nH_{2n+1}$, and where x and n are integers and $1 \leq x \leq 3$) or using, for example, polymers with a functional group chosen from $-COOH$, $-PO_3H_2$, $-SH$, or $-NH_2$. As another example, if a surface of the adapter site 104 is made of metal oxide with hydrophilic property, it may be modified to be hydrophobic using, for example, $R1_x$-Si$(O-R2)_{4-x}$ (where R1 is a hydrophobic group, such as alkyl chain $-(CH_2)_n-CH_3$, and R2 is $-C_nH_{2n+1}$, and where x and n are integers and $1 \leq x \leq 3$) or using, for example, polymers with a functional group chosen from $-COOH$, $-PO_3H_2$, $-SH$, or $-NH_2$. By making an upper surface of the adapter site 104 hydrophobic but keeping the bottom surface of the adapter site 104 hydrophilic, a movable light coupler comprising one hydrophobic surface and one hydrophilic surface (see descriptions of light coupler surface modification below) may be positioned at the adapter site in a specific orientation with the hydrophilic surface being positioned in the effective excitation zone near the bottom of the adapter site rather than facing upwards or toward a sidewall surface of the adapter site. Thus, a molecule localized on one region of the surface of the movable light coupler (e.g., in this example, the hydrophilic surface), or a molecule from a sample solution 120 which interacts with the molecule localized on the surface of the light coupler, may be effectively excited by the excitation light entering the effective excitation zone in the confined space near the bottom of the adapter site.

Figure 5:
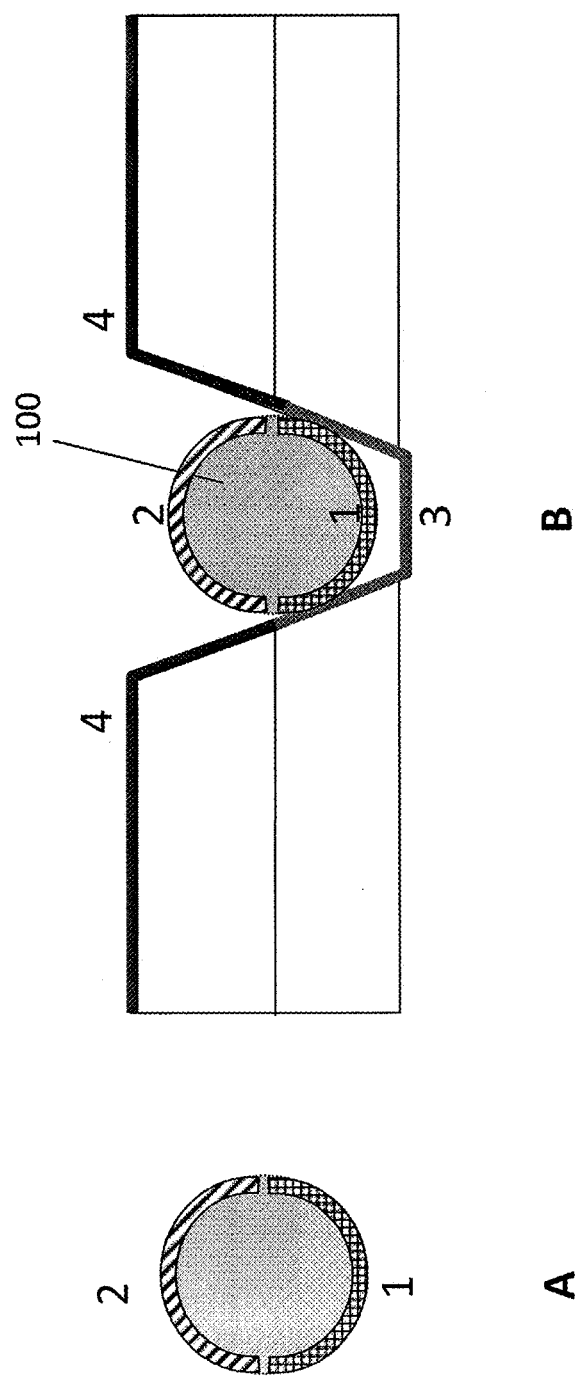
FIG. 5 shows schematic illustrations of a movable light coupler and waveguide adapter site with surface modifications according to some embodiments.
Figure 6:
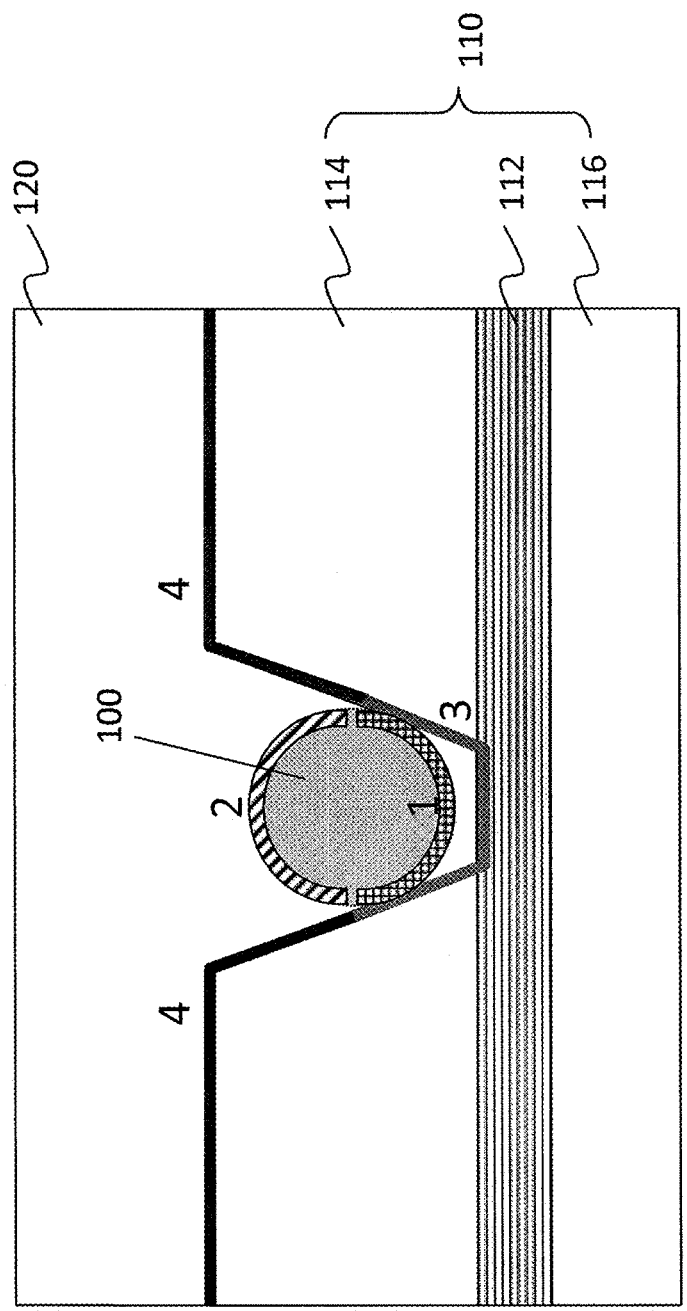
FIG. 6 shows a schematic illustration of a movable light coupler and waveguide adapter site with surface modifications according to some embodiments.

With further reference to embodiments schematized in FIG. 5 and FIG. 6, in some embodiments, surface modifications 1 and 3 are surface modifications with groups having opposite charges, i.e., surface 1 is positively charged and surface 3 is negatively charged, or vice versa.

In some embodiments, at least a region of the surface of the movable light coupler is modified with oligonucleotides. A schematic view of an exemplary detection system comprising a movable light coupler comprising a surface modification with oligonucleotides is illustrated in FIG. 4. In some embodiments, the oligonucleotides are complementary to the sequence of a sequencing primer utilized in the nucleic acid synthesizing reaction. In further embodiments, the oligonucleotides have random sequences. The oligonucleotides may be from 10 to 100 nucleotides in length. For example, the oligonucleotides may be from 10 to 20, 20 to 30, 30 to 40, 50 to 60, 60 to 80, or 80 to 100 nucleotides in length. It is to be understood that these nucleotide length ranges are approximate, and that a specified range for nucleotide length includes a number of nucleotides that is "about" in this range, e.g., oligonucleotides from 10 to 100 nucleotides in length includes oligonucleotides from about 10 to 100 nucleotides in length. The length of the oligonucleotides may be less than 10 nucleotides. The oligonucleotides may be, for example, 6, 7, 8, 9, 10, 11, 12, 13, 14, 15, 16, 17, 18, 19, 20, 21, 22, 23, 24, 25, 26, 27, 28, 29, 30, or more than 30 nucleotides in length. In some embodiments, the length of the oligonucleotides corresponds to the length of the sequencing primer. In some embodiments, the oligonucleotides are shorter in length than the sequencing primer. The oligonucleotides may be linked directly to the movable light coupler, or they may be linked to a moiety by which the oligonucleotides may be coupled to a movable light coupler, e.g., a biotin group, which may bind to a streptavidin or avidin linked to the surface of a movable light coupler.

A region of surface modification may be introduced on the movable light coupler using manufacturing processes known in the art. For example, a region of surface modification may be introduced by temporarily masking one portion of the light coupler while the remaining portion of the surface of the light coupler is modified. For example, one hemisphere of a nano-scale sphere light coupler may be masked while the other hemisphere receives a surface modification. In some embodiments, the light coupler is partially coated with a heterogenous material by a process of aligning one or more light couplers on a substrate (e.g., a glass or silicon substrate), depositing a heterogenous material on the surface of the coupler aligned on a substrate, and then utilizing a lift-off method to remove the modified light coupler from the substrate. Alignment of a light coupler on a substrate can be performed by spin-coating, dip-coating, embedding, nanoimprinting, nano ink-printing, use of nanoparticle self assembly technology (e.g., self-assembly of nanoparticles on a substrate pre-patterned by chemical lithography), or by similar methods. Deposition of a heterogeneous material on the light coupler may be performed by such methods as sputter deposition, magnetron sputter deposition, evaporation, atomic layer deposition, chemical vapor deposition, physical vapor deposition (PVD), electron beam (e.g., e-gun) deposition, plasma deposition, laser flash evaporation (e.g., evaporated metal deposition), or the like. The lift-off method may be ultrasonic agitation, chemical treatment (e.g., treatment with acetone), magnetic lift-off, or physically peeling away the deposited layer with the aid of a razor blade. Exemplary manufacturing processes suitable for the production of movable light coupler particles having asymmetric surface modification are described in Park, H., et al., "Multifunctional nanoparticles for photothermally controlled drug delivery and magnetic resonance imaging enhancement," SMALL 4(2):192-196 (2008); International Patent Publication Number WO 2008/002101, entitled "Multi-functional nanoparticles partially-deposited with gold film"; Anker, J. N., et al., "Magnetically-Modulated Optical Nanoprobes (MagMOONs) and Systems," JOURNAL OF MAGNETISM AND MAGNETIC MATERIALS 293:655-662 (2005); Perro, A., et al., "Design and synthesis of Janus micro- and nanoparticles," JOURNAL OF MATERIALS CHEMISTRY 15: 3745-3760 (2005); McNaughton, B. H., et al., "Fabrication of uniform half-shell magnetic nanoparticles and microspheres with applications as magnetically modulated optical nanoprobes," arXiv:cond-mat/0506418v1, Jun. 16, 2005, 1-6; and Wu, L. Y., et al., "Bioinspired nanocorals with decoupled cellular targeting and sensing functionality, SMALL 6(4):503-507 (2010), each of which is incorporated herein by reference in its entirety.

1.2.4 Directed Localization of the Movable Light Coupler at an Adapter Site

In some embodiments, a movable light coupler particle with a surface-localized binding moiety for a single-molecule object (i.e., a molecule or molecular complex capable of binding a single-molecule object) is localized at an adapter site formed in a waveguide using an electric field, a magnetic field, or using hydrophilic surface character or other chemical character according to the design of the light coupler.

Figure 7:
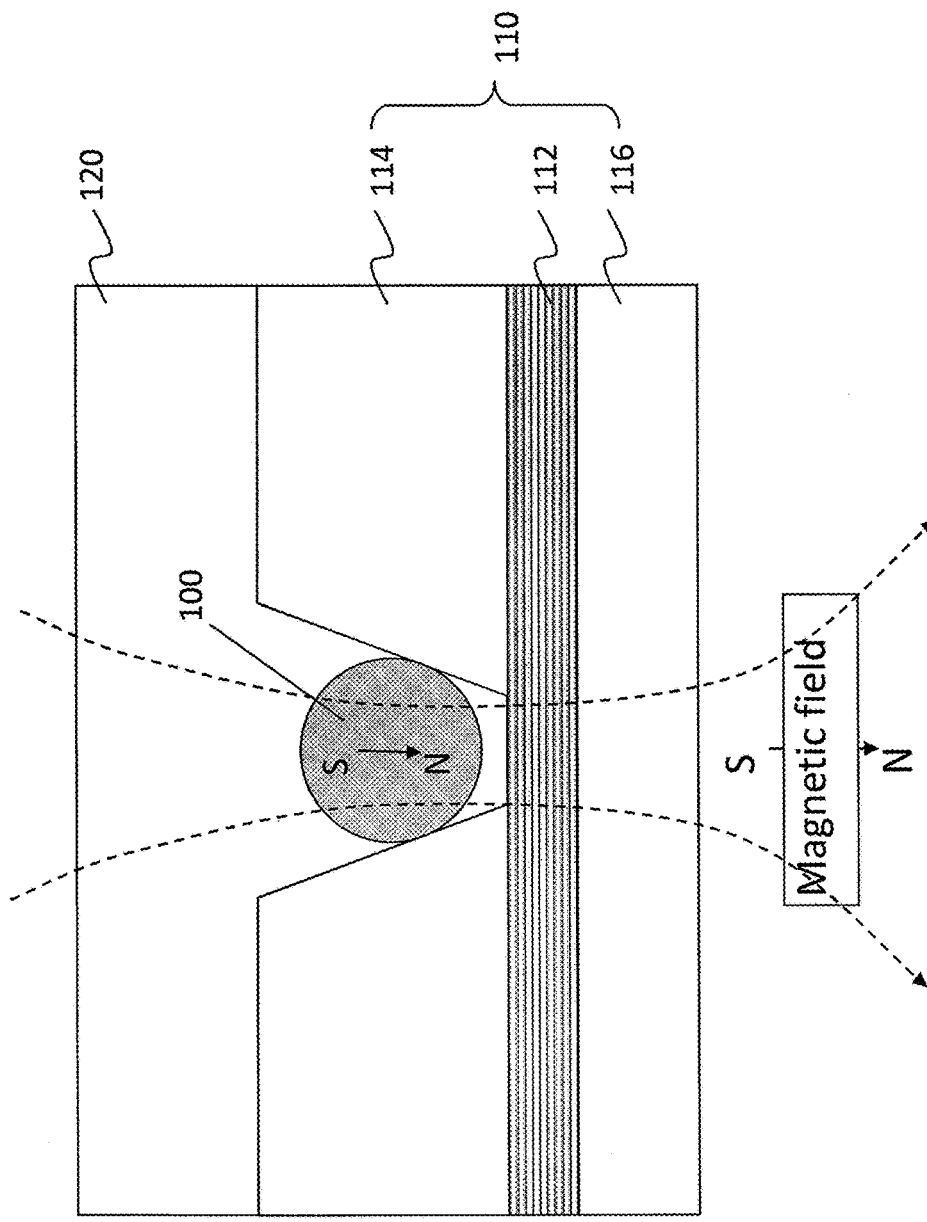
FIG. 7 is a schematic view of an exemplary detection system with a movable light coupler oriented at an adapter site in a specific orientation with the aid of a magnetic field.

A light coupler which comprises magnetic materials and/or is modified with magnetic functional groups on its surface may be localized at an adapter site by application of a magnetic field to the adapter site, as schematized in FIG. 7. For example, micro-fabricated coils may be placed under the adapter site. When an electric current is passed through the micro-fabricated coils, the coils may generate a magnetic field which directs a light coupler present in the sample solution into an adapter site and traps the light coupler against the bottom of the adapter site. A suitable method for trapping magnetic nano-particles is described in Ramadan, Q., et al., "Customized trapping of magnetic particles," MICROFLUID NANOFLUID 6:53-62 (2009), which is incorporated herein by reference in its entirety.

A light coupler that is modified with charged functional groups may be localized at an adapter site by application of an electric potential across the adapter site. For example, micro-fabricated electrodes may be positioned at the bottom of an adapter site in the form of a glass slide coated with a layer of conducting material to act as an electrode. Application of an electric current, e.g., direct current, to the electrodes generates an electric field through the adapter site which acts as an electrophoretic particle entrapment system that directs the modified light coupler into the adapter site. Suitable electrophoretic techniques for directing nano-particles to specific detection sites are described in Han, J., et al., "High performance electrophoresis system for site-specific entrapment of nanoparticles in a nanoarray", PROC. SPIE 7574:75740L (2010) and in Velev, O. D., et al., "Particle-localized AC and DC manipulation and electrokinetics", ANNU. REP. PROG. CHEM., SECT. C, 105:213-246 (2009), each of which is incorporated herein by reference in its entirety.

1.2.5 Other Optional Components of the System

In some embodiments, as shown in FIG. 4, an optical filter 118 may be arranged between the core layer 112 and the detector 102. In some embodiments, the filter may be arranged between a lower cladding layer (not shown in FIG. 4) and the light detector 102. In some embodiments, the optical filter may be arranged between a lower protection layer (not shown) and the light detector 102. In some embodiments, a lower protection layer itself may serve as an optical filter. An optical filter may allow a light with a wavelength within a certain range to pass through but at least partially block a light with a wavelength outside the certain range. Therefore, by properly choosing the optical filter 118, the light emitted from the object may be allowed to pass through but the noise caused by the excitation light is reduced, so as to improve the S/N ratio.

The movable light coupler and object to be detected may be contained in a sample solution 120, which may fill the adapter site 104. In some embodiments, a microfluidic channel (not shown) may be used to conduct the sample solution into the adapter site. The microfluidic channel may be designed in a way that the target objects pass through the adapter site one at a time, so as to realize a flow-cytometry-like detection. In some embodiments, a cover (not shown) may be formed over the detection system to contain the sample solution and/or to block the ambient light.

In some of the above-described figures schematically showing the structures of detection systems, for simplicity, some components are not shown. For example, each panel of FIG. 2 only shows the movable light coupler 100, the waveguide 110 and the adapter site 104 components of the detection system. Other components of the detection system are not shown. It is to be understood that the detection systems shown in these figures may also comprise other components as disclosed herein. For example, the detection system shown in each panel of FIG. 2 may also comprise a light detector, a cover, a protection layer(s), a light source, and/or an optical filter.

2. METHODS OF DETECTION AND APPLICATIONS

In another aspect, the disclosure relates to a method of detecting an object, such as a single-molecule object, using the detection system as disclosed herein. As used herein, the term "single-molecule object" includes an object composed of a single molecule and a single object composed of multiple noncovalently linked molecules, such as a single multimeric polypeptide complex or a single segment of double-stranded DNA. A sample solution comprising the object may be filled in the adapter site formed in the waveguide of the detection system. An incident light emitted by a light source may be at least partially coupled by a light coupler into the waveguide and propagate in the core layer of the waveguide. The light coupled into the waveguide may serve as an excitation light, and may at least partially couple to a movable light coupler localized at an adapter site formed in the waveguide. The object, when entering the effective excitation zone at the bottom of the adapter site and/or surrounding the surface of the light coupler localized at the adapter site, may be excited by the excitation light and emit a light to be detected by a light detector.

Furthermore, there is provided a method of detecting a single-molecule object, comprising the steps of a) introducing an incident light from a light source into a waveguide, thereby forming an excitation light in the waveguide, b) localizing a single-molecule object on a movable light coupler, c) localizing the movable light coupler of (b) at an adapter site for a movable light coupler formed in at least a first cladding layer of the waveguide, and d) exciting, by the excitation light, a single-molecule object localized on the movable light coupler, causing the single-molecule object to emit a light to be detected by a light detector. In some embodiments, localization of the movable light coupler at an adapter site for a movable light coupler formed in at least a first cladding layer of the waveguide forms a confined space suitable for single-molecule detection.

Furthermore, there is provided a method of detecting a single-molecule object comprising the steps of a) providing a detection apparatus comprising (i) a movable light coupler, (ii) a waveguide comprising a core layer and a first cladding layer, wherein at least one adapter site for the movable light coupler is formed in at least the first cladding layer, and (iii) a light detector; b) providing at least one binding moiety capable of binding a single-molecule object; c) localizing the at least one binding moiety individually on the surface of the movable light coupler; d) providing a single-molecule object sample to one binding moiety localized on the movable coupler; e) localizing at the adapter site the movable light coupler on which the at least one binding moiety and single-molecule object are localized; f) introducing an incident light from a light source into the waveguide, thereby forming an excitation light in the waveguide; and g) exciting, by the excitation light, a single-molecule object bound to the at least one binding moiety localized on the movable light coupler, causing the single-molecule object to emit a light to be detected by a light detector. In some embodiments, localization at an adapter site of a movable light coupler on which the at least one binding moiety and single-molecule object are localized creates a confined space suitable for single-molecule detection, wherein the single-molecule object to be detected is localized within the confined space.

In some embodiments, methods of detecting a single-molecule object relate to methods of detecting the interaction of target molecules and/or molecular complexes, e.g., receptor ligands and receptor complexes, antigens and antibodies, or free nucleotide triphosphates and nucleic acid-synthesizing reaction complexes. In some embodiments, methods include detection of a labeled molecule. In some embodiments, the label is a fluorescent label. In some embodiments, the label is a fluorescent molecule. In further embodiments, the label is a fluorescent protein. In certain embodiments, the label is a quantum dot. In some embodiments, the label is a member of a FRET donor/acceptor pair. The detection system, and method of using the same, may be applied to, e.g., nucleic acid detection, DNA sequencing, biomarker identification, or flow cytometry. The detection systems can detect and process low intensity light signal, which makes single-molecule detection possible.

Furthermore, there is provided a method of sequencing a nucleic acid, comprising the steps of a) providing a detection apparatus comprising (i) a movable light coupler, (ii) a waveguide comprising a core layer and a first cladding layer, wherein at least one adapter site for the movable light coupler is formed in at least the first cladding layer, and (iii) a light detector; b) providing at least one nucleic acid molecule; c) localizing the at least one nucleic acid molecule individually on the movable light coupler; d) localizing at the adapter site the movable light coupler on which at least one nucleic acid is localized; e) performing single molecule sequencing-by-synthesis of the at least one nucleic acid molecule, wherein the single molecule nucleic acid sequencing-by-synthesis produces an emitted light correlated to the identity of at least one base in the nucleic acid; f) detecting the emitted light with the detector, resulting in an output signal; and g) processing the output signal to determine an identity of at least one base comprised by the nucleic acid.

In some embodiments, the methods comprise forming covalent attachments, such as between reagents or target objects and labels and between functional groups and surfaces, e.g., surfaces of a movable light coupler or of the adapter site. For example, to prepare movable light coupler particles modified with oligonucleotides, streptavidin may be linked to the surface of a light coupler in order to bind biotinylated oligonucleotides. In some embodiments, a single-molecule object binding moiety such as a polypeptide or polypeptide complex may be linked to the surface of a light coupler. Many methods for forming covalent attachments, such as of reagents to surfaces or labels, are known in the art. Non-covalent attachment methods can also be used. A number of different chemical modifiers can be used to facilitate attachment formation. Examples of chemical modifiers include N-hydroxy succinimide (NHS) groups, amines, aldehydes, epoxides, carboxyl groups, hydroxyl groups, hydrazides, hydrophobic groups, membranes, maleimides, biotin, streptavidin, thiol groups, nickel chelates, photoreactive groups, boron groups, thioesters, cysteines, disulfide groups, alkyl and acyl halide groups, glutathiones, maltoses, azides, phosphates, and phosphines. These can easily be prepared, for example, using standard methods (MICROARRAY BIOCHIP TECHNOLOGIES, Mark Schena, Editor, March 2000, Biotechniques Books). In some embodiments, attachments are formed between two entities by using an appropriate combination of modifiers (e.g., an electrophilic modifier and a nucleophilic modifier), wherein each entity comprises at least one modifier.

In some embodiments, attachments are formed between two entities by using a chemical modifier present on one of the entities and a naturally-occurring moiety, for example, an amine or sulfhydryl, of the other entity. In some embodiments, modifiers that are reactive to amines are used. An advantage of this reaction is that it can be fast and can avoid production of toxic by-products. Examples of such modifiers include NHS-esters, aldehydes, epoxides, acyl halides, and thio-esters. Most proteins, peptides, glycopeptides, etc., have free amine groups, which can react with such modifiers to link them covalently to these modifiers. Nucleic acid probes with internal or terminal amine groups can also be synthesized, and are commercially available (e.g., from IDT or Operon). Thus, biomolecules can be bound (e.g., covalently or noncovalently) to labels, surfaces, or other reagents using similar chemistries.

A number of other multi-functional cross-linking agents can be used to convert the chemical reactivity of one kind of modifier to another. These groups can be bifunctional, tri-functional, tetra-functional, and so on. They can also be homo-functional or hetero-functional. An example of a bi-functional cross-linker is X—Y—Z, where X and Z are two reactive groups, and Y is a connecting linker. Further, if X and Z are the same group, such as NHS-esters, the resulting cross-linker, NHS—Y—NHS, is a homo-bi-functional cross-linker and could connect two entities that each comprise an amine. If X is NHS-ester and Z is a maleimide group, the resulting cross-linker, NHS—Y-maleimide, is a hetero-bi-functional cross-linker and could link an entity comprising an amine with an entity comprising a thio-group. Cross-linkers with a number of different functional groups are widely available. Examples of such functional groups include NHS-esters, thio-esters, alkyl halides, acyl halides (e.g., iodoacetamide), thiols, amines, cysteines, histidines, di-sulfides, maleimide, cis-diols, boronic acid, hydroxamic acid, azides, hydrazines, phosphines, photoreactive groups (e.g., anthraquinone, benzophenone), acrylamide (e.g., acrydite), affinity groups (e.g., biotin, streptavidin, maltose, maltose binding protein, glutathione, glutathione-S-transferase), aldehydes, ketones, carboxylic acids, phosphates, hydrophobic groups (e.g., phenyl, cholesterol), etc.

Other modifier alternatives (such as photo-crosslinking and thermal crosslinking) are known to those skilled in the art. Commercially available technologies include, for example, those from Mosiac Technologies (Waltham, Mass.), EXIQON™ (Vedbaek, Denmark), Schleicher and Schuell (Keene, N.H.), Surmodics™ (St. Paul, Minn.), XENOPORE™ (Hawthorne, N.J.), Pamgene (Netherlands), Eppendorf (Germany), Prolinx (Bothell, Wash.), Spectral Genomics (Houston, Tex.), and COMBIMATRIX™ (Bothell, Wash.).

2.1 Labels for Use with the Detection System

In some embodiments of the methods described herein, one or more labels are attached to the target single-molecule object(s) (i.e., the substance[s] to be detected, such as nucleotides, including nucleotide analogs), or to the probe(s), such as primers, antibodies, or other reagents that interact with the object(s) or other reagent(s). Any label can be used on the single-molecule object or probe which can be useful in the correlation of signal with the amount or presence of the object.

For example, a wide variety of fluorescent molecules can be utilized, including small molecules, fluorescent proteins, and quantum dots. Useful fluorescent molecules (fluorophores) include, but are not limited to: 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; AFPs-AutoFluorescent Protein-(Quantum Biotechnologies); Texas Red; Texas Red-X conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; Tri-Color (PE-Cy5); TRITC (TetramethylRodamineIsoThioCyanate); True Blue; TruRed; Ultralite; Uranine B; Uvitex SFC; WW 781; X-Rhodamine; XRITC; Xylene Orange; Y66F; Y66H; Y66W; YO-PRO-1; YO-PRO-3; YOYO-1; interchelating dyes such as YOYO-3, Sybr Green, Thiazole orange; members of the Alexa Fluor dye series (from Molecular Probes/Invitrogen) which cover a broad spectrum and match the principal output wavelengths of common excitation sources such as Alexa Fluor 350, Alexa Fluor 405, 430, 488, 500, 514, 532, 546, 555, 568, 594, 610, 633, 635, 647, 660, 680, 700, and 750; members of the Cy Dye fluorophore series (GE Healthcare), also covering a wide spectrum such as Cy3, Cy3B, Cy3.5, Cy5, Cy5.5, Cy7; members of the Oyster dye fluorophores (Denovo Biolabels) such as Oyster-500, -550, -556, 645, 650, 656; members of the DY-Labels series (Dyomics), for example, with maxima of absorption that range from 418 nm (DY-415) to 844 nm (DY-831) such as DY-415, -495, -505, -547, -548, -549, -550, -554, -555, -556, -560, -590, -610, -615, -630, -631, -632, -633, -634, -635, -636, -647, -648, -649, -650, -651, -652, -675, -676, -677, -680, 681, -682, -700, -701, -730, -731, -732, -734, -750, -751, -752, -776, -780, -781, -782, -831, -480XL, -481XL, -485XL, -510XL, -520XL, -521XL; members of the ATTO series of fluorescent labels (ATTO-TEC GmbH) such as ATTO 390, 425, 465, 488, 495, 520, 532, 550, 565, 590, 594, 610, 611 X, 620, 633, 635, 637, 647, 647N, 655, 680, 700, 725, 740; members of the CAL Fluor series or Quasar series of dyes (Biosearch Technologies) such as CAL Fluor Gold 540, CAL Fluor Orange 560, Quasar 570, CAL Fluor Red 590, CAL Fluor Red 610, CAL Fluor Red 635, Quasar 670; quantum dots, such as quantum dots of the EviTags series (Evident Technologies) or quantum dots of the Qdot series (Invitrogen) such as the Qdot 525, Qdot565, Qdot585, Qdot605, Qdot655, Qdot705, Qdot 800; fluorescein; rhodamine; and/or phycoerythrin; or combinations thereof. See, e.g., U.S. Application Publication No. 2008/0081769.

In embodiments encompassing single-molecule nucleic acid sequencing of a target nucleic acid localized on a movable light coupler which is localized at an adapter site, nucleotides incorporated into a nascent DNA strand may be detected by excitation and detection of a fluorophore linked directly to the incoming nucleotide, e.g., a fluorophore that is linked to the beta or gamma phosphate of the dNTP and that is cleaved upon incorporation of the dNTP into the growing strand. In some embodiments, nucleotides incorporated into a nascent strand are detected using fluorescence resonance energy transfer (FRET)-based detection. For example, in some embodiments, a FRET-based method as described in U.S. Patent Application No. 2010/0035268 can be used. In such embodiments, a Quantum dot capable of acting as a fluorescence donor may be linked to a sequencing primer, and the dNTPs used to synthesize the growing strand carry a fluorescence acceptor group on their terminal (gamma) phosphate group. Incorporation of the fluorophore-labeled nucleotide polyphosphates into the growing nucleotide strand at an active site complementary to the target nucleic acid is detected in real-time by detecting emission of the dNTP-linked fluorescence acceptors following fluorescence resonance energy transfer from the excited Quantum dot fluorescence donor. The identity of each incorporated nucleotide is determined by its fluorescent label, wherein the fluorescence label is then cleaved from the nucleotide upon incorporation into the growing strand.

2.2 Nucleic Acid Detection

The detection system may be used in methods or processes of molecule detection, e.g., nucleic acid sequencing.

This system, and methods or processes utilizing it, are useful for, e.g., analytical and diagnostic applications.

The detection system may be used with a wide variety of sequencing modalities and may be suitable for sequencing single molecules. Additionally, the detection system has simplified design, assembly, and production relative to existing biochip devices.

2.2.1 Molecules to be Detected

Nucleic acids suitable for detection may include any nucleic acid, including, for example, DNA, RNA, or PNA (peptide nucleic acid), and may contain any sequence—both known and unknown, including naturally occurring or artificial sequences. The nucleic acid may be naturally derived, recombinantly produced, or chemically synthesized. The nucleic acid may comprise naturally-occurring nucleotides, nucleotide analogs not existing in nature, or modified nucleotides. The length of the nucleic acid to be detected may vary based on the actual application. In some embodiments, the nucleic acid may include at least 10, 20, 50, 100, 200, 500, 1000, 2000, 5000, 10000, 20000 bases, or more. In some embodiments, the nucleic acid may be from 10 to 20, from 10 to 50, from 10 to 100, from 50 to 100, from 50 to 500, from 50 to 1000, from 50 to 5000, from 500 to 2000, from 500 to 5000, or from 1000 to 5000 bases.

A nucleic acid may be single-stranded for detection. Single stranded nucleic acid templates may be derived from a double stranded molecule by means known in the art including, for example, heating or alkali or other chemical treatment. Single stranded nucleic acid templates may also be produced by, e.g., chemical or in vitro synthesis.

In some embodiments, the nucleic acid to be detected is circular. In some embodiments, the methods comprise providing a circular nucleic acid molecule comprising an insert with a known sequence, which can be used as a binding site for a primer. The circular nucleic acid molecule can be provided in a single- or double-stranded state, and will generally comprise at least one covalently closed strand. Double-stranded circular molecules may comprise a nicked strand or a second covalently closed strand.

In some embodiments, the circular nucleic acid molecule is provided by isolating it in circular form from its source, if part of its sequence is known and thus can serve as the nucleic acid insert (e.g., a conserved motif within the sequence of a gene contained in the circular molecule may be known, or the molecule may be known to contain a sequence based on its ability to hybridize under high stringency conditions to another nucleic acid of known sequence). In some embodiments, the sequence of the nucleic acid insert is known only inexactly, as would be the case when knowledge of the sequence is derived from stringent hybridization properties. In some embodiments, the sequence of the nucleic acid insert is known exactly, such as would be the case when the circular nucleic acid molecule has a known backbone sequence or has been engineered to contain a known sequence.

In some embodiments, the circular nucleic acid molecule is provided by performing an in vitro reaction or reactions to incorporate a linear nucleic acid sample into a circular molecule along with a nucleic acid insert. The in vitro reaction or reactions can in some embodiments comprise ligation by a ligase and/or other strand joining reactions such as can be catalyzed by various enzymes, including recombinases and topoisomerases. DNA ligase or RNA ligase may be used to enzymatically join the two ends of a linear template, with or without an adapter molecule or linkers, to form a circle, as exemplified in FIG. 8. For example, T4 RNA ligase couples single-stranded DNA or RNA, as described in Tessier et al., ANAL BIOCHEM, 158: 171-78 (1986). CIRCLIGASE™ (Epicentre, Madison, Wis.) may also be used to catalyze the ligation of a single stranded nucleic acid. Alternatively, a double stranded ligase, such as *E. coli* or T4 DNA ligase, may be used to perform the circularization reaction.

In some embodiments, providing the circular nucleic acid molecule comprises replicating a nucleic acid template by extending from at least one primer (which can include random primers with 5' flaps of known sequence that can serve as the nucleic acid insert) comprising complementary regions and circularizing the amplified nucleic acid, such as may be catalyzed by a ligase or a recombinase; the amplified nucleic acid may in some embodiments be processed at its ends, e.g., by restriction or phosphorylation, prior to circularization.

In some embodiments, the circular nucleic acid molecule is provided by performing chemical circularization. Chemical methods employ known coupling agents such as BrCN plus imidazole and a divalent metal, N-cyanoimidazole with $ZnCl_2$, 1-(3-dimethylaminopropyl)-3 ethylcarbodiimide HCl, and other carbodiimides and carbonyl diimidazoles. The ends of a linear template may also be joined by condensing a 5'-phosphate and a 3'-hydroxyl, or a 5'-hydroxyl and a 3'-phosphate.

In some embodiments, the circular nucleic acid molecule contains an insert sequence that could be considered an end link primer (discussed below) except that it is not at an end, since the molecule is circular.

2.2.1.1 End Link Primer

In some embodiments, a linear nucleic acid may further comprise one or more end link primers coupled to the 5' end, the 3' end, or both the 5' end and the 3' end of the nucleic acid. In particular embodiments, an end link primer may be affixed to the 3' end of the nucleic acid. End link primers may be used to provide a complementary sequence for one or more detecting primers, e.g., a sequencing primer.

End link primers are short nucleic acid molecules usually composed of less than 100 nucleotides. In some embodiments, the end link primer may be at least 5, 10, 15, 20, 25, 30, 50, 75, 90 nucleotides, or more, in length. In certain embodiments, end link primers may be from 8 to 25, from 10 to 20, from 10 to 30, or from 10 to 50 nucleotides in length. In some embodiments, the end link primers may be unbranched, however, in other embodiments, they may be branched.

The end link primer may serve as a complement to one or more primers used to detect the nucleic acid, e.g., a sequencing primer. In some embodiments, the primer may be used to detect the nucleic acid by hybridization, e.g., the primer may contain a detectable label, e.g., a fluorescent label. In some embodiments, the 5' end of the end link primer may comprise a sequence complementary to a sequencing primer. In some embodiments, the end link primer sequence that is complementary to the sequencing primer may be oriented so that the 3' end of the sequencing primer may be immediately adjacent to the first nucleotide in the nucleic acid to be sequenced.

In some embodiments, end link primers may be added to ends of the nucleic acid to be detected by a ligase, for example, a DNA ligase. In some embodiments, the end link primer and nucleic acid to be detected may be both single stranded before the ligation. In other embodiments, both may be double stranded. In still other embodiments, one may be single stranded and the other may be double stranded. Ligation is well known in the art. For example, in the polony sequencing method, Shendure et al. (SCIENCE, 309:1728-1732 [2005]) ligated a T30 end link primer (32 bp) to a sample DNA segment with the New England Biolabs' (NEB) Quick Ligation™ kit. There, the ligation reaction solution included 0.26 pmole of DNA, 0.8 pmole of T30 end link primer, 4.0 µl T4 DNA Ligase, in 1× Quick Ligation Buffer. After mixing, the reaction solution was incubated for about 10 minutes at room temperature, and then placed on ice. The ligation reaction was stopped by heating the samples to 65° C. for 10 minutes.

In other embodiments, the end link primer may be synthesized on the nucleic acid to be sequenced. For example, the end link primer may be a homopolymer added by, e.g., terminal transferase. For example, Harris et al., (SCIENCE 320:106-109 [2008]) added a poly-A tail to DNA templates, which served as the complement to a poly-T sequencing primer in the single molecule sequencing of a viral genome.

2.2.1.2 Sequencing Primer

A sequencing primer is a single-stranded oligonucleotide complementary to a segment of the nucleic acid to be detected or its associated end link primer. In some embodiments, the sequencing primer may be at least 8, 10, 15, 20, 25, 30, 35, 40, 45, 50 nucleotides, or more in length. In particular embodiments, the sequencing primer may be from 8 to 25, from 10 to 20, from 10 to 30, or from 10 to 50 nucleotides in length. The sequencing primer may be made up of any type of nucleotide, including naturally-occurring nucleotides, nucleotide analogs not existing in nature, or modified nucleotides.

In some embodiments, a sequencing primer may contain modified nucleotides, e.g., locked nucleic acids (LNAs; modified ribonucleotides, which provide enhanced base stacking interactions in a polynucleic acid). As an illustration of the utility of LNAs, Levin et al. (NUCLEIC ACID RESEARCH 34(20):142 [2006]) showed that a LNA-containing primer had improved specificity and exhibited stronger binding relative to the corresponding unlocked primer. Three variants of the MCP1 primer (5'-cttaaattttcttgaat-3') containing 3 LNA nucleotides (in caps) at different positions in the primer were made: MCP1-LNA-3' (5'-cttaaattttCtTgaAt-3'); MCP1-LNA-5' (5'-CtTaAattttcttgaat-3'); and MCP1-LNA-even (5'-ctTaaatTttctTgaat-3'). All LNA-substituted primers had enhanced $T_m$, while the MCP1-LNA-5' primer exhibited particularly enhanced sequencing accuracy (Phred Q30 counts). Accordingly, in particular embodiments, the sequencing primer may contain at least one locked nucleotide in its 5' region, i.e., the 5' half, third, or quarter of the sequencing primer.

Sequencing primers and single-stranded target nucleic acids (i.e., a nucleic acid to be sequenced including at least one end link primer) may be hybridized before or after being combined with a nucleic acid polymerizing enzyme, dNTPs, and appropriate buffer components for nucleic acid polymerization, and may then be adsorbed to a movable light coupler. The sequencing primer and sample nucleic acid may be hybridized by mixing the sample nucleic acid with a molar excess of sequencing primer in a salt-containing solution, such as 5×SSC (or 5×SSPE), 0.1% Tween 20 (or 0.1% SDS), and 0.1% BSA buffer. The mixture may be heated to 65° C. for at least 5 minutes and slowly cooled to room temperature, to allow primer/template annealing. Residual primers may be eliminated by appropriate means including, e.g., a molecular sieve.

Figure 9:
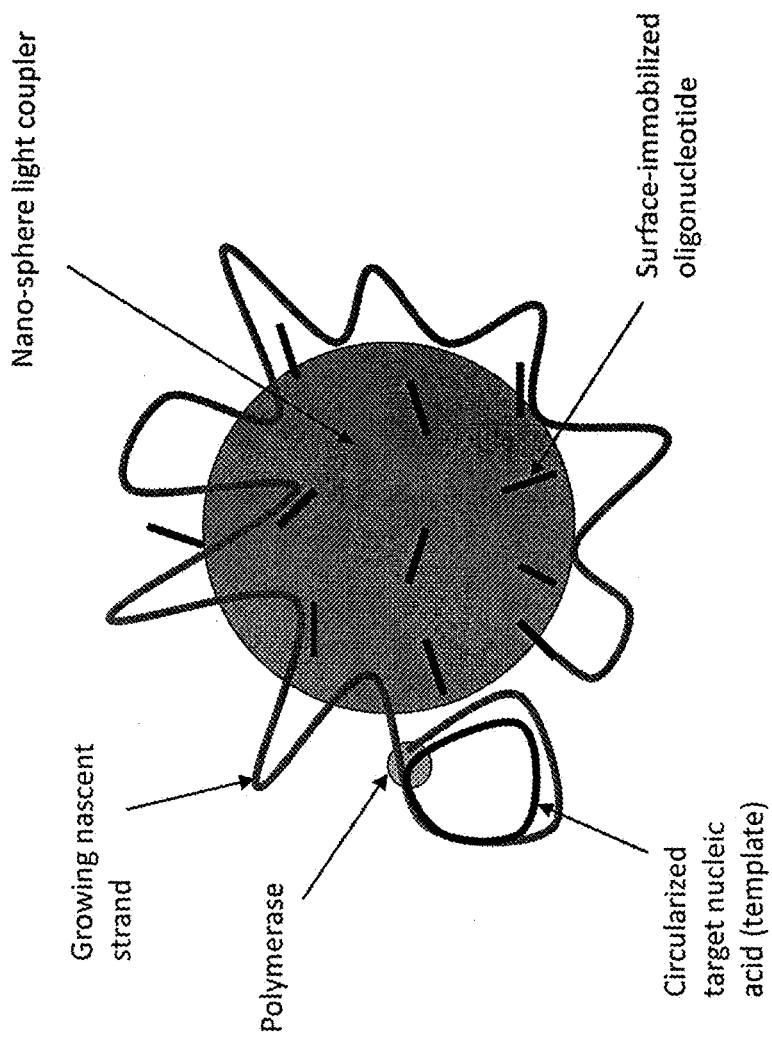
FIG. 9 is a schematic illustration of an exemplary movable light coupler with a nucleic acid-synthesizing reaction complex localized on its surface.
Figure 10:
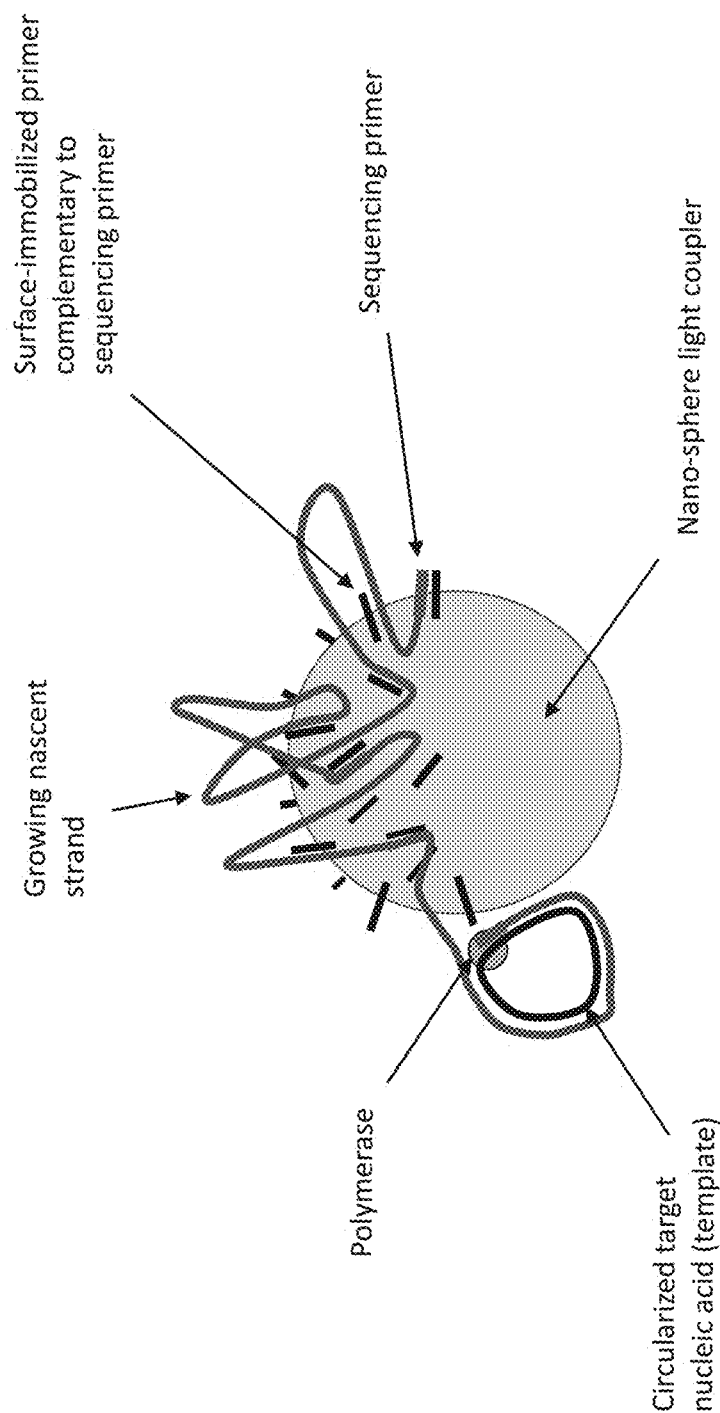
FIG. 10 is a schematic illustration of an exemplary movable light coupler with a nucleic acid-synthesizing reaction complex localized on its surface.
Figure 11:
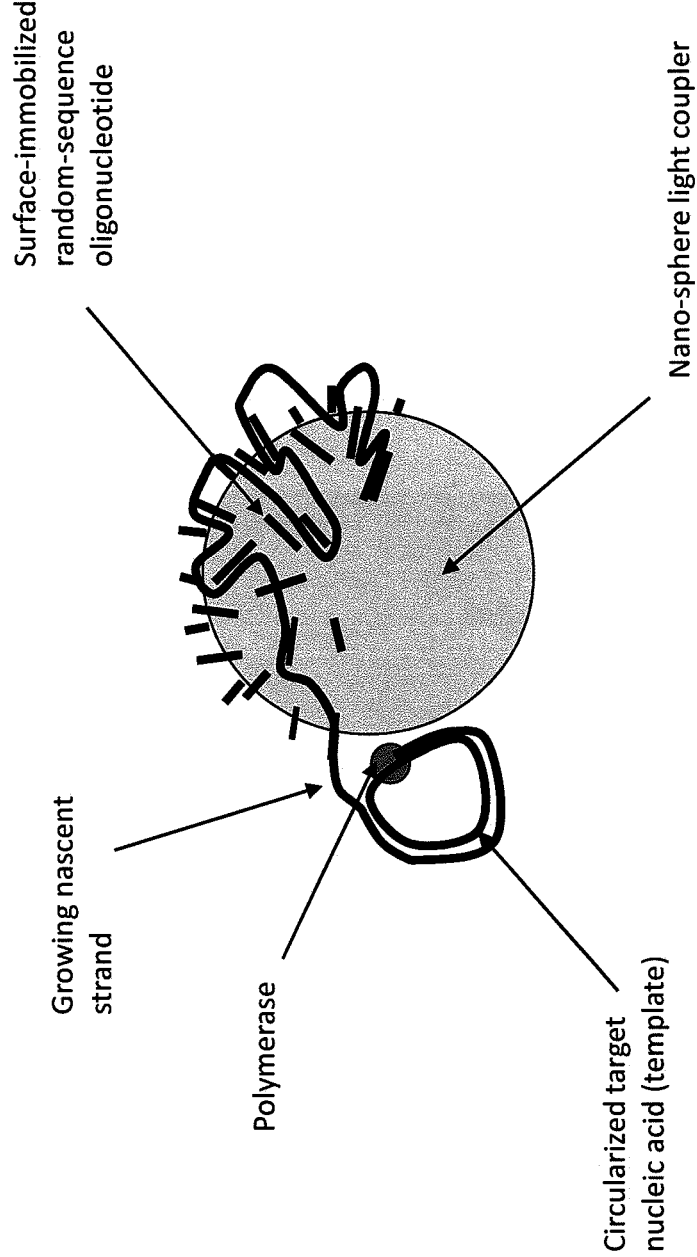
FIG. 11 is a schematic illustration of an exemplary movable light coupler with a nucleic acid-synthesizing reaction complex localized on its surface.

In some embodiments, a target nucleic acid is localized on a movable light coupler as a component of a nucleic acid-synthesizing reaction complex, wherein neither the synthesis reaction may be localized in a confined space at a waveguide adapter site without requiring immobilization of the polymerase or target nucleic acid to a surface. To prepare a nucleic-acid synthesizing reaction complex localized on the surface of movable light coupler, a circularized target nucleic acid prepared as described may be combined with a sequencing primer, a nucleic acid polymerizing enzyme, dNTPs, and appropriate buffer components for nucleic acid synthesis. The polymerase may proceed around the circularized template in multiple cycles, generating a growing nascent strand comprising multiple copies of the template strand. The polymerizing complex may then be combined with a movable light coupler modified with oligonucleotides on its surface, as shown schematically in FIG. 9. Thus, in such embodiments, neither the target strand template nor the polymerase is itself immobilized on a surface. The oligonucleotides may comprise a sequence that hybridizes to the sequencing primer sequence, multiple copies of which may be embedded in the growing nascent strand. These embedded sequences may bind to the oligonucleotides bound to the surface of the light coupler, as shown schematically in FIG. 10. In some embodiments, the oligonucleotides comprise random sequences, which may hybridize to the growing nascent strand in various locations, as shown schematically in FIG. 11. In some embodiments, the movable light coupler may be modified with oligonucleotides over its entire surface, as shown in FIG. 9. In further embodiments, the movable light coupler is modified with oligonucleotides on only a portion of its surface, as shown in FIG. 10 and FIG. 11.

Figure 12:
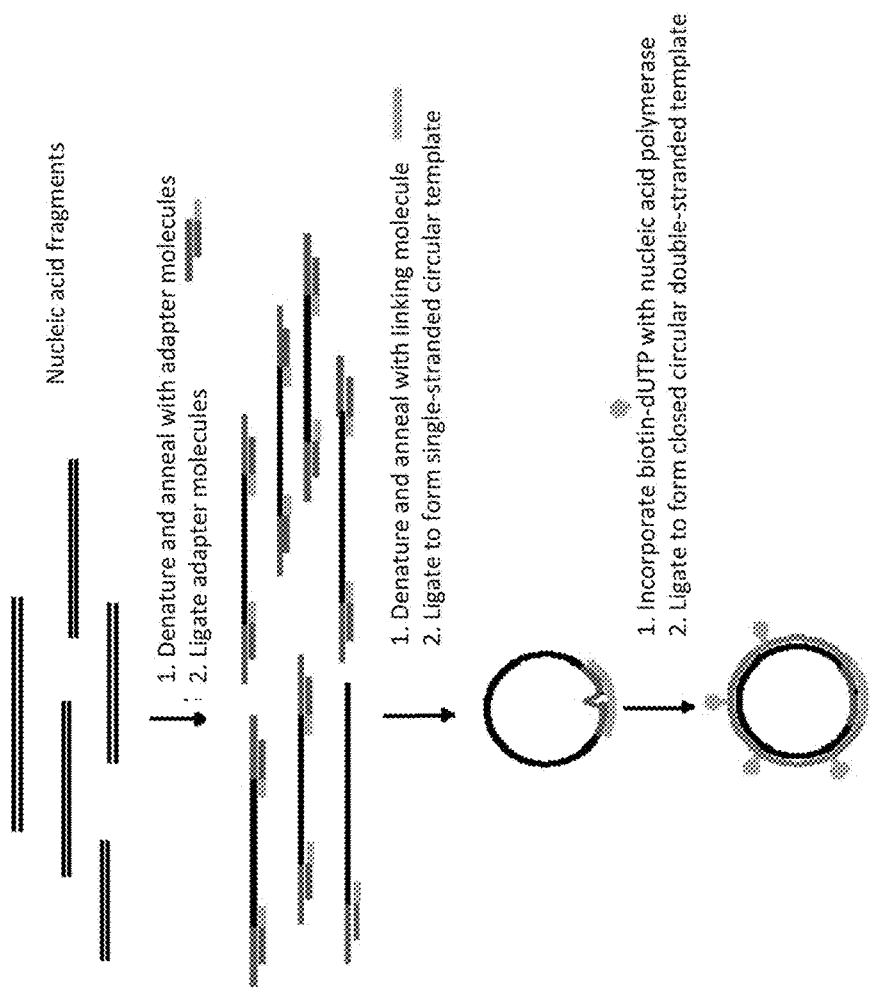
FIG. 12 depicts an exemplary method of producing a double-stranded circular target nucleic acid.
Figure 13:
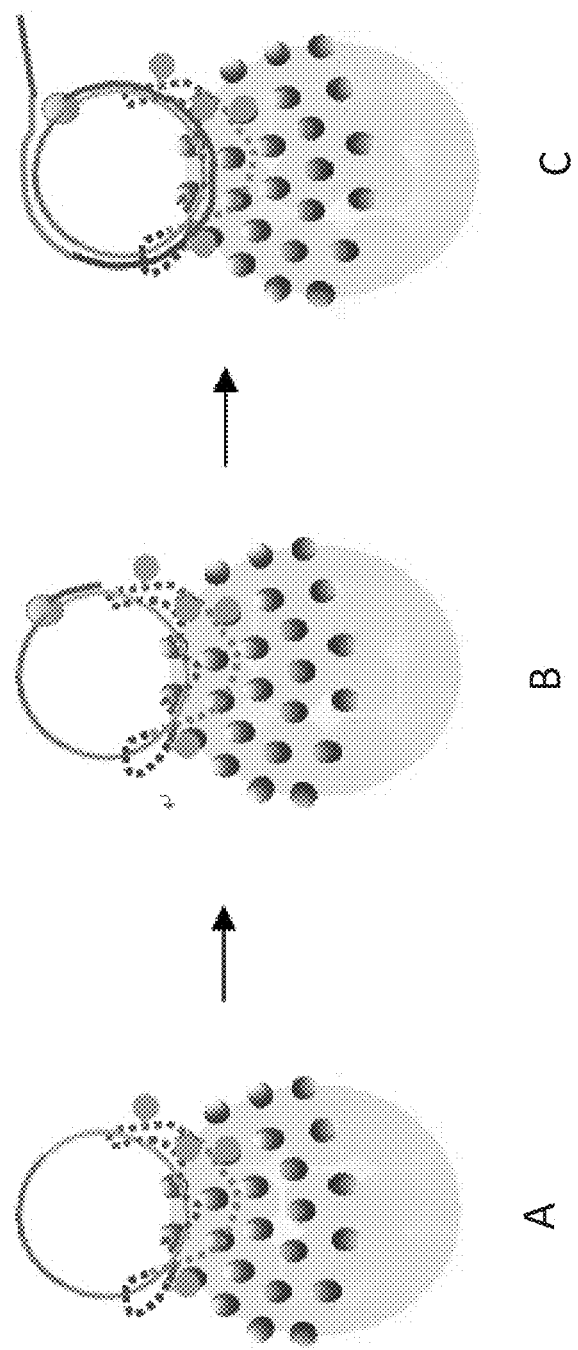
FIG. 13 provides schematic illustrations of a denatured, double-stranded circular target nucleic acid localized on the surface of a movable light coupler.

In some embodiments, a double-stranded target sequence comprising a strand with incorporated biotinylated uracil bases is generated by preparing a circular, single-stranded target strand using a linking primer which is able to hybridize to both ends of the single-stranded target nucleic acid, and polymerizing a second strand with a nucleic acid polymerase and a dNTP mixture supplemented with biotinylated dUTP, as shown in FIG. 12. The double-stranded target may be denatured and combined with streptavidin-modified light coupler particles, thereby adsorbing the denatured target strand to the light coupler by virtue of the biotinylated strand with which it is intertwined, as shown in FIG. 13A. Upon addition of a polymerase, dNTPs, a sequencing primer, and appropriate buffer components for nucleic acid synthesis, a nucleic acid-synthesizing reaction complex may form, wherein the complex is adsorbed to the surface of a movable light coupler without immobilization of the polymerase or the target nucleic acid, as shown in FIGS. 13B and 13C. A polymerase, dNTPs, and buffer components can be added before or after localization of the light coupler with adsorbed template at adapter site.

Primers, including both end link and sequencing primers, may be designed by appropriate means, including visual inspection of the sequence or computer-assisted primer design. Numerous software packages are available to assist in the primer design, including DNAStar™ (DNAStar, Inc., Madison, Wis.), OLIGO 4.0 (National Biosciences, Inc.), Vector NTI® (Invitrogen), Primer Premier 5 (Premierbiosoft), and Primer3 (Whitehead Institute for Biomedical Research, Cambridge, Mass.). Primers may be designed taking into account, for example, the molecule to be sequenced, specificity, length, desired melting temperature, secondary structure, primer dimers, GC content, pH and ionic strength of the buffer solution, and the enzyme used (i.e., polymerase or ligase). See, e.g., Joseph Sambrook and David Russell, MOLECULAR CLONING: A LABORATORY MANUAL Cold Spring Harbor Laboratory Press; 3rd edition (2001).

2.2.2 Sequencing Modalities

Some embodiments are methods of sequencing a nucleic acid, comprising the steps of a) providing a detection apparatus comprising (i) a movable light coupler, (ii) a waveguide comprising a core layer and a first cladding layer, wherein at least one adapter site for the movable light coupler is formed in at least the first cladding layer, and (iii) a light detector; b) providing at least one nucleic acid molecule; c) localizing the at least one nucleic acid molecule individually on the surface of the movable light coupler d) localizing at the adapter site the movable light coupler having the at least one nucleic acid localized on its surface; e) performing single molecule sequencing-by-synthesis of the at least one nucleic acid molecule, wherein the single molecule nucleic acid sequencing-by-synthesis leads to emission of light correlated to the identity of at least one base in the nucleic acid; f) detecting the light with the detector, resulting in an output signal; and g) processing the output signal to determine an identity of at least one base comprised by the nucleic acid.

In these methods, "localizing the at least one nucleic acid molecule individually on the surface of the movable light coupler and localizing at the adapter site the movable light coupler having the at least one nucleic acid localized on its surface" is understood to mean that a single nucleic acid molecule may be located on a movable light coupler which is localized at an adapter site, i.e., there is at least one adapter site in which one (and not more than one) nucleic acid molecule is localized. In some embodiments, there are a plurality of adapter sites which each individually contain one (and not more than one) movable light coupler comprising a nucleic acid molecule localized on its surface. In some embodiments, during operation, some of the plurality of adapter sites contain light couplers each having one target nucleic acid molecule localized on its surface, and other adapter sites either do not contain light couplers or contain light couplers that do not have a surface-localized target nucleic acid molecule. That is, the concentration of light couplers with surface-localized nucleic acids in the sample solution is lower than a certain value so that not all adapter sites have light couplers with surface-localized nucleic acid contained in them. This may prevent the scenario that two or more nucleic acid molecules localize at an adapter site before a sequencing is completed, so as to prevent the results of one sequencing from comprising information from more than one molecule. For example, in some embodiments, less than or equal to 50%, 40%, 30%, 25%, 20%, 15%, 10%, 9%, 8%, 7%, 6%, 5%, 4%, 3%, 2%, or 1% of the adapter sites will generate a signal due to the low concentration of the biological molecules localized at adapter sites to be detected or identified. In instances in which a first target nucleic acid dissociates from the surface of a light coupler localized at an adapter site, and a second nucleic acid subsequently associates with the same light coupler localized at the adapter site, the results of sequencing the first nucleic acid may be distinguished from the results of sequencing of the second nucleic acid by any gap in the detection of incorporated nucleotides and/or by differences in the determined nucleotide sequences.

In some embodiments, the single molecule nucleic acid sequencing-by-synthesis leads to emission of light via chemiluminescence. Notably, in these embodiments, it is not necessary for the apparatus to comprise a light source, as chemiluminescence generates light from chemical energy.

In some embodiments, the apparatus further comprises a light source, which may be used to provide excitatory light, e.g., for causing the single molecule nucleic acid sequencing-by-synthesis to emit light via fluorescence.

The detection apparatuses and methods may be used to detect and sequence nucleic acids by means known in the art, as reviewed in, e.g., U.S. Pat. No. 6,946,249 and Shendure et al., NAT. REV. GENET. 5:335-44 (2004). The sequence modalities can be chosen from single-molecule sequencing methods known in the art. In some embodiments, the sequencing methods may rely on the specificity of either a DNA polymerase or DNA ligase and may include, e.g., base extension sequencing (single base stepwise extensions) and multi-base sequencing-by-synthesis (including, e.g., sequencing with terminally-labeled nucleotides).

For single-molecule sequencing modalities, the detection system can offer the advantage of being able to resequence single molecules. For example, a template nucleic acid molecule to be sequenced can be provided in circular form together with a sequencing primer. Resequencing can be achieved by performing a plurality of sequencing cycles such that a sequence read is obtained that is greater than the number of nucleotides in the template nucleic acid molecule. The sequencing read therefore comprises information that redundantly identifies the base in at least one position in the template nucleic acid molecule. In some embodiments, the sequencing read comprises information that redundantly identifies at least 25%, 50%, 75%, 90%, 91%, 92%, 93%, 94%, 95%, 96%, 97%, 98%, 99%, or 100% of the bases in the template nucleic acid molecule. In some embodiments, the sequencing read comprises information that identifies at least 25%, 50%, 75%, 90%, 91%, 92%, 93%, 94%, 95%, 96%, 97%, 98%, 99%, or 100% of the bases in the template nucleic acid molecule with three-fold, four-fold, five-fold, seven-fold, or ten-fold or greater redundancy. By resequencing the same molecule, sequencing errors are expected to fall as the power of the number of sequencing reads. For example, if per base error rates for a single read are $10^{-3}$, then after two reads, this falls to $(10^{-3})^2$, i.e., $10^{-6}$. This is particularly advantageous for single-molecule sequencing since the modified nucleotides used for sequencing can lose their labels or blocking groups resulting in, e.g., spurious deletions.

The viability of enzymes and fluorophore labels on nucleotides can be gradually lost as a nucleic acid synthesis reaction proceeds. When the rate of sequence reading slows down, a reaction mixture can be washed out of the detection system and replaced with fresh solutions for continuous sequence reading. In some embodiments, the reaction mixture is supplemented with fresh reagents rather than washed out and replaced.

In general, in single-molecule sequencing, at least one nucleic acid molecule to be sequenced is contacted with a primer. The primer is modified, e.g., by performing at least one enzyme-catalyzed polymerization or ligation reaction. The at least one reaction leads to emission of light correlated to the identity of at least one base in the nucleic acid. "Leading to" emission of light is understood to mean that the at least one reaction causes at least one condition under which light emission correlated to the identity of at least one base in the nucleic acid occurs; this occurrence may be via interaction with excitatory light, a chemi- or bio-luminescent system, etc. The at least one condition can be, for example, incorporation of a fluorophore into the product of the at least one reaction, or the release of pyrophosphate. Thus, light may be generated with or without external excitation. For example, single-molecule sequencing can be performed with reversible terminator base analogs comprising a covalently-linked detectable label, e.g., a fluorescent label, and a blocking group to prevent any secondary extension, wherein the analog is excited and detected after it has been added to the primer, and the label and blocking group are removed after addition to allow another round of extension. Alternatively, a product of an extension step, such as a pyrophosphate, can be detected without external excitation by providing a chemi- or bio-luminescent detection system which emits light in a pyrophosphate-dependent manner. These and other modalities are discussed in more detail below.

The light emitted is correlated to the identity of at least one base in the nucleic acid. In some embodiments, the correlation can be temporal; e.g., the time of emission of the light indicates the identity of the at least one base, such as is the case when different base analogs are provided for use in a polymerization reaction at different times. In some embodiments, the correlation can be spectral; e.g., the spectrum of the emitted light indicates the identity of the at least one base, such as is the case when different base analogs that comprise different fluorophores are provided for use in a polymerization reaction.

In some embodiments, single-molecule nucleic acid sequencing comprises multiple sequencing cycles. A sequencing cycle is understood to mean the events that lead to an emission of light correlated to the identity of at least one base that would be repeated in order to identify at least a second base in the nucleic acid after a first base has been identified. Thus, in methods that comprise single-molecule nucleic acid sequencing, the single-molecule nucleic acid sequencing can comprise at least a given number of sequencing cycles that lead to at least the given number of emissions of light correlated collectively to the identity of at least the given number of bases in the nucleic acid, and the method comprises identifying at least the given number of bases in the nucleic acid. In some embodiments, the given number may be, for example, 2, 3, 4, 5, 10, 20, 50, 100, 200, or 500.

Sequencing methods can comprise determining the identity of one or more bases in a nucleic acid. In some embodiments in which performing single-molecule nucleic acid sequencing leads to emission of light that is detected with at least one light detector comprising at least a first optical sensor and a second optical sensor, and output signal from the at least two optical sensors is processed, the identity of at least one base in a nucleic acid can be determined by comparing at least one result of the processing with at least one known result corresponding to at least one known type.

For example, a result of the processing can indicate a time at which a reaction occurred; when light emitted is temporally correlated to the identity of at least one base in the nucleic acid, said time can be used to identify at least one base in the nucleic acid.

In another example, a result of the processing can be a determination of which fluorophore was incorporated into the product of a reaction; when light emitted is spectrally correlated to the identity of at least one base in the nucleic acid, said determination can be used to identify at least one base in the nucleic acid.

2.2.2.1 Base Extension Sequencing: Stepwise Extension

In some embodiments, a detection system may be used to detect light generated during base extension sequencing. In some embodiments, base extension sequencing begins by providing a partial duplex sample nucleic acid comprising a single-stranded nucleic acid to be sequenced, an end link primer associated with the 3' end of nucleic acid to be sequenced, and a sequencing primer annealed thereto. In some embodiments, polymerase and modified nucleotides may be then applied to the light detection system in a suitable buffer. In some embodiments, the nucleotides may include a covalently-linked detectable label, e.g., a fluorescent label, and a blocking group to prevent any secondary extension. Accordingly, the sequencing pauses after the addition of a single nucleotide to the 3' end of sequencing primer.

In a first step of one embodiment of a base extension sequencing reaction, a nucleotide with a fluorescent blocking group may be added by a DNA polymerase to the 3' end of sequencing primer. In some embodiments, the fluorescent label may act as the blocking group. In other embodiments, they may be separate moieties. A single nucleotide may be incorporated at the 3' end of sequencing primer and is identified by its label by the corresponding light detector. The fluorescent label and blocking group are then removed, e.g., by chemical or enzymatic lysis, to permit additional cycles of base extension. In certain embodiments, the label and blocking groups may be removed simultaneously or sequentially and in any order. By compiling the order of the bases added, the sequence of the sample nucleic acid may be deduced in the 3' to 5' direction, one base at a time.

Generally, there are two ways to recognize the nucleotide added during stepwise extension. In the first case, the four nucleotides may all have the same detectable label, but are added one at a time, in a predetermined order. The identity of the extended nucleotide may be determined by the order that the nucleotide is added in the extension reaction. In the second mode for recognizing the base integrated during extension, four different nucleotides may be added at the same time and each is coupled with a distinct detectable label. In different embodiments, the excitation or emission spectra and/or intensity of the labels may differ. The identity of the nucleotide added in the extension may be determined by the intensity and/or wavelength (i.e., excitation or emission spectra) of the detected label.

2.2.2.2 Sequencing by Synthesis: Multi-Step Extension

In some embodiments, sequencing by synthesis may proceed with multiple uninterrupted extensions, e.g., without the use of blocking groups. In these embodiments, the polymerization reaction may be monitored by detecting the release of the pyrophosphate after nucleoside triphosphate hydrolysis, i.e., the release of the beta and gamma phosphate complex. This complex may be detected directly, for example, by a fluorescent moiety on the complex, or indirectly, for example, by coupling the pyrophosphate to a chemi- or bio-luminescent detection system, as discussed above.

In some embodiments, the sample nucleic acid may be sequenced essentially continuously by using terminal-phosphate-labeled nucleotides. Exemplary embodiments of terminal-phosphate-labeled nucleotides and methods of their use are described in, e.g., U.S. Pat. No. 7,361,466 and U.S.

Patent Publication No. 2007/0141598, published Jun. 21, 2007. Briefly, the nucleotides may be applied to the detection system and, when hydrolyzed during the polymerization, the labeled pyrophosphate may be detected by a corresponding light detector. In some embodiments, all four nucleotides may comprise distinct labels and be added simultaneously. In some embodiments, the nucleotides may comprise indistinguishable, e.g., identical, labels and be added sequentially in a predetermined order. Sequential, cyclical addition of nucleotides with indistinguishable labels still permits multiple, uninterrupted polymerization steps, e.g., in homopolymer sequences.

2.2.3 Additional Applications

The detection apparatus may simultaneously detect millions of nucleic acid segments. If each segment is, for example, 1000 bases long, a single device could obtain upwards of billions of base sequences at once. Discussed below are additional applications of the systems and methods provided herein.

2.2.3.1 Whole-Genome Sequencing

The detection system may be used to perform whole or partial genome sequencing of, e.g., a virus, bacterium, fungi, eukaryote, or vertebrate, e.g., a mammal, e.g., a human.

Genomic DNA may be sheared into fragments of at least 20, 50, 100, 200, 300, 500, 800, 1200, 1500 nucleotides, or longer, for sequencing. In some embodiments, the sheared genomic DNA may be from 20 to 50, from 20 to 100, from 20 to 500, from 20 to 1000, from 500 to 1200, or from 500 to 1500 nucleotides long. In some embodiments, the nucleic acids to be sequenced, along with associated end link primers, may be made single stranded, annealed to a sequencing primer, and applied to the detection system for sequencing as described above.

2.2.3.2 Gene Expression Profiling

In other embodiments, the detection system may be used to sequence cDNA for gene expression profiling. For example, mRNA levels may be quantified by measuring the relative frequency that a particular sequence is detected on a device. Several million cDNA molecules may be sequenced in parallel on a device as described herein. If a cell contains, on average, 350,000 mRNA molecules, a transcript present at even one copy per cell is expected to be sequenced approximately three times in one million sequencing reactions. Accordingly, the detection system is suitable for single-molecule sequencing with single-copy-number sensitivity. In other embodiments, the detection system may be used to sequence RNA directly for gene expression profiling (i.e., direct RNA sequencing, see e.g., Ozsolak et al., NATURE 461: 814-818 (2009)).

cDNA synthesis is well known in the art and typically includes total RNA extraction with optional enrichment of mRNA. cDNA is produced from mRNA by steps including, for example: reverse transcription, for first strand synthesis; RNAse treatment, to remove residual RNA; random hexamer priming of the first strand, and second strand synthesis by DNA polymerase. The resultant cDNA is suitable for sequencing on the systems described herein. Methods of isolating and preparing both DNA and RNA are well known in the art. See, for example, Joseph Sambrook and David Russell, MOLECULAR CLONING: A LABORATORY MANUAL Cold Spring Harbor Laboratory Press; 3rd edition (2001).

2.2.3.3 Additional Detection Methods (a) FRET

In some embodiments, a molecule may be detected on the detection system by fluorescence resonance energy transfer (FRET; also known as Förster resonance energy transfer). As is known in the art, FRET occurs when an excited donor molecule non-radiatively transfers energy to an acceptor molecule, which emits the energy, typically as light. FRET can help reduce background light by, e.g., providing greater spectral separation between effective excitation and emission wavelengths for a molecule being detected. FRET is often used to detect close molecular interactions since its efficiency decays as the sixth power of the distance between donor and acceptor molecules. For example, Zhang et al. (NATURE MATERIALS 4:826-31 [2005]) detected nucleic acid hybridization by FRET. There, a biotinylated nucleic acid target was conjugated to an avidin-coated quantum dot donor, which then excited a Cy5-conjugated DNA probe. In some embodiments, a labeled molecule free in a sample solution and a labeled molecule or molecular complex which binds to the free molecule and is localized on the surface of a movable light coupler may form a donor/acceptor (or vice versa) pair for detection by FRET.

In some embodiments of nucleic acid sequencing using the detection system, fluorescently labeled nucleotides may act as acceptor chromophores for a donor chromophore attached to a polymerase or ligase. Accordingly, in these embodiments, the donor chromophore located on the polymerase or ligase may excite an acceptor chromophore on a nucleotide being polymerized on, or ligated to, the target nucleic acid. Nucleotides not proximate to the polymerase may be not excited due to the rapid falloff in FRET efficiency. In some embodiments, the donor molecule may be, e.g., another fluorophore, e.g., a quantum dot. Quantum dots, e.g., semiconductor quantum dots are known in the art and are described in, e.g., International Patent Publication No. WO 03/003015. Means of coupling quantum dots to, e.g., biomolecules are known in the art, as reviewed in, e.g., Mednitz et al., NATURE MATERIALS 4:235-46 (2005) and U.S. Patent Publication Nos. 2006/0068506 and 2008/0087843, published Mar. 30, 2006, and Apr. 17, 2008, respectively. In some embodiments, quantum dots may be conjugated to a DNA polymerase molecule. As already discussed above for conjugating enzymes to linker sites, the skilled artisan will undoubtedly appreciate that when conjugating fluorophores to, e.g., a DNA polymerase or ligase, care must be taken to retain enzyme function by mitigating any effect of conjugating the fluorophore on the primary, secondary, and tertiary structures of the enzyme.

(b) Multi-Photon Excitation

In some embodiments, a chromophore may be excited by two or more photons. For example, in some embodiments, excitation of either a donor or acceptor chromophore in FRET may be via two or more photons. Two-photon and multi-photon excitation are described further in, e.g., U.S. Pat. Nos. 6,344,653 and 5,034,613.

(c) Time-Resolved Detection

In some embodiments, the excitation light source and light detectors of a detection system may be modulated to have a characteristic phase shift. Using methods known in the art, for example, as disclosed in U.S. Patent Publication No. 2008/0037008, published Feb. 14, 2008, light emitted from a molecule being detected on the detection system may be measured by a corresponding light detector without interference from an excitation light source.

(d) Other Fluorescent Detection Systems and Methods

In some embodiments, methods relate to detection of light emitted by at least one object in a biological cell, which can be a living or fixed cell. In some embodiments, the at least one object is chosen from at least one object comprising at least one quantum dot, at least one object comprising at least one fluorescent protein, and at least one object comprising at least one fluorescent small chemical moiety. In some embodiments, the at least one object is fluorescently labeled and comprises at least one oligonucleotide, polynucleotide, oligopeptide, polypeptide, oligosaccharide, polysaccharide, or lipid.

In some embodiments, the at least one object comprises a fixed and limited number of fluorophores, such as at most 20, 10, 5, or 2 fluorophores, which can be chosen from quantum dots, fluorescent proteins, and fluorescent small chemical moieties. In some embodiments, the at least one object comprises only a single fluorophore chosen from a quantum dot, a fluorescent protein, and a fluorescent small chemical moiety. Many examples of fluorescent small chemical moieties are discussed above. In some embodiments, fluorescent small chemical moieties have an emission peak between 300 and 800 nm and/or a quantum yield (fraction of photons emitted per photon of peak absorption wavelength absorbed) of at least 0.1, 0.2, 0.3, 0.4, 0.5, 0.6, 0.7, 0.8, or 0.9.

3. EXAMPLES

Figure 8:
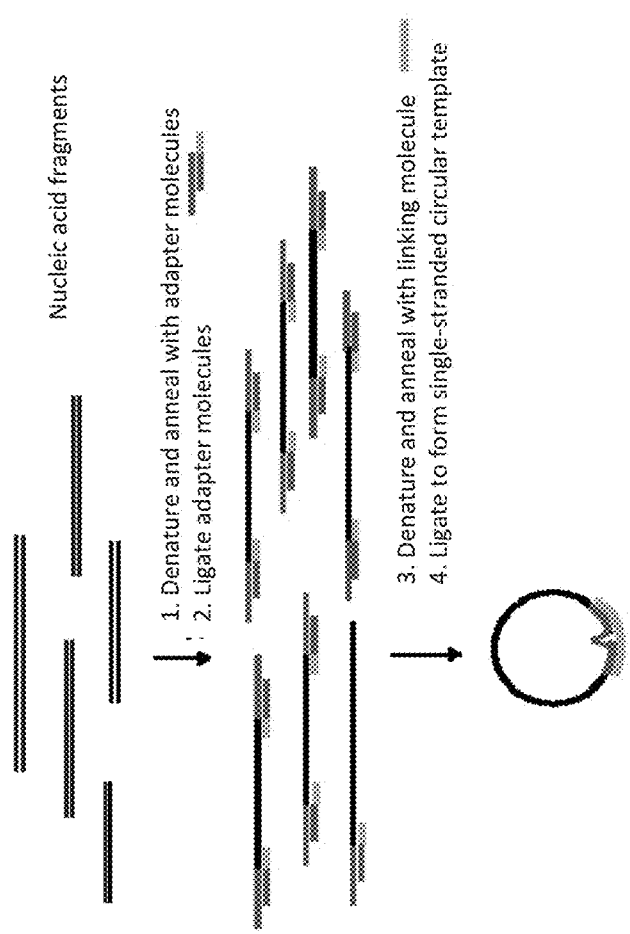
FIG. 8 depicts an exemplary method of producing a single-stranded circular target nucleic acid.

3.1 Example 1—Preparation of a Nano-Sphere Light Coupler with a Nucleic Acid-Synthesizing Reaction Complex Localized on its Surface A single-stranded circular DNA template is constructed using the process schematized in FIG. 8. A pool of target double-stranded nucleic acid fragments is denatured and combined with self-complementary adapter nucleic acid molecules. The adapter nucleic acid molecules comprise overhanging sequences that are complementary to the ends of one strand of each of the target nucleic acid fragments. The adapter molecules are allowed to anneal to the single-stranded target strands, and a ligating enzyme is added to ligate the adapter molecules to each of the target nucleic acid fragments. The products of this ligation are then denatured and combined with a linking nucleic acid molecule that is complementary to both adapter molecule sequences ligated to the ends of each target strand. Each target strand is then circularized using a ligating enzyme.

The circularized target strand and hybridized linking nucleic acid molecule are combined with a DNA polymerase, dNTPs, and appropriate buffer components to form a nucleic acid-synthesizing reaction complex, where the linking nucleic acid molecule functions as a sequencing primer. The target strand is then replicated in a continuous manner, wherein the polymerase proceeds around the circular template repeatedly, displacing the nascent strand from the template in successive replications of the template. This produces a nascent strand of DNA containing multiple copies of the complement of the target sequence, where each of these copies is separated by a segment having the sequence of the sequencing primer.

The surface of a nano-sphere particle is chemically modified with streptavidin. Biotinylated oligonucleotide primers comprising a sequence complementary to the sequence of the sequencing primer (the linking nucleic acid molecule) are combined with the streptavidin-modified nano-sphere, thereby linking the biotinylated primers to the nano-sphere. The oligonucleotide-coated nano-sphere is combined with the reaction complex comprising the DNA polymerase, circular template strand, and replicated strand described in the preceeding paragraph. The sequencing primer sequences embedded in the replicated strand hybridize to the oligonucleotides immobilized on the surface of the nano-sphere, thereby anchoring the reaction complex to the surface of the nano-sphere as illustrated in FIG. 9.

3.2 Example 2—Preparation of a Nano-Sphere Light Coupler with a Nucleic Acid-Synthesizing Reaction Complex Localized on One Hemisphere Using Specific Primers A nano-sphere particle is modified on one hemisphere with streptavidin. Biotinylated oligonucleotide primers each comprising a sequence complementary to the sequence of a sequencing primer (e.g., a linking nucleic acid molecule as shown in FIG. 8) are combined with the streptavidin-modified nano-sphere, thereby linking the biotinylated primers to the streptavidin-coated hemisphere of the nano-sphere. The oligonucleotide-coated nano-sphere is combined with a reaction complex comprising a DNA polymerase, circular template strand, and replicated strand as described in Example 1. The sequencing primer sequences embedded in the replicated strand hybridize to the complementary oligonucleotides immobilized on one hemisphere of the nano-sphere, thereby anchoring the reaction complex to the surface of the nano-sphere as illustrated in FIG. 10.

3.3 Example 3—Preparation of a Nano-Sphere Light Coupler with a Nucleic Acid-Synthesizing Reaction Complex Localized on One Hemisphere Using Random-Sequence Primers A nano-sphere is modified on one hemisphere with streptavidin. Biotinylated oligonucleotide primers each comprising a random nucleotide sequence are combined with the streptavidin-modified nano-sphere, thereby linking the biotinylated primers to the streptavidin-coated hemisphere of the nano-sphere. The oligonucleotide-coated nano-sphere is combined with a reaction complex comprising a DNA polymerase, circular template strand, and replicated strand as described in Example 1. The nascent replicated strand hybridizes to the oligonucleotides immobilized on one hemisphere of the nano-sphere, thereby anchoring the reaction complex to the surface of the nano-sphere as illustrated in FIG. 11.

3.4 Example 4—Preparation of a Nano-Sphere Light Coupler with a Nucleic Acid-Synthesizing Reaction Complex Localized on One Hemisphere by a Biotinylated, Double-Stranded Template A double-stranded circular DNA template is constructed using the process schematized in FIG. 12. A pool of target double-stranded nucleic acid fragments is denatured and combined with self-complementary adapter nucleic acid molecules. The adapter nucleic acid molecules comprise overhanging sequences that are complementary to the ends of one strand of each of the target nucleic acid fragments. The adapter molecules are allowed to anneal to each single-stranded target strand, and a ligating enzyme is added to ligate the adapter molecules to each target nucleic acid fragment. The products of this ligation are then denatured and combined with a linking nucleic acid molecule that is complementary to both adapter molecule sequences ligated to the ends of each target strand. Each target strand is then circularized using a ligating enzyme.

A nucleic acid polymerase and a dNTP mixture supplemented with biotin-dUTP are added to the annealed DNA molecules. The hybridized linking nucleic acid molecule functions as a sequencing primer, and a second strand comprising biotinylated uracil bases is synthesized using a polymerase without strand-displacing activity. A ligating enzyme included in the synthesis mixture forms a closed, circular, double-stranded DNA when the polymerase completes synthesis of the second strand.

The closed, circular, double-stranded DNA is denatured and mixed with a nano-scale particle with one hemisphere modified with streptavidin. The DNA and streptavidin-modified particle are combined at an appropriate molar ratio for a single template to be attached per nano-sphere particle, as illustrated in FIG. 13A. The nonbiotinylated strand is localized on the surface of the nano-sphere by virtue of being intertwined with the biotinylated strand localized on the surface of the nano-sphere.

DNA polymerase, a sequencing primer complementary to the target strand, fluorescently labeled dNTPs, and appropriate buffer components are combined with the nano-sphere and bound template, allowing a DNA-synthesizing reaction complex to form on the surface of the nano-sphere (FIG. 13B). The polymerase proceeds around the template, forming a nascent synthesized strand (FIG. 13C).

3.5 Example 5—Localization at a Waveguide Adapter Site of a Magnetic Nano-Sphere with a Surface-Localized Nucleic Acid-Synthesizing Complex A nano-sphere particle is uniformly surface-modified with magnetic functional groups. A nucleic acid-synthesizing reaction complex is localized onto the magnetically-modified surface of the nano-sphere as described in Example 1. The nano-sphere with surface-localized reaction complex is localized at an adapter site formed in a waveguide by use of micro-fabricated coils located underneath the adapter site. Passing an electric current through the micro-fabricated coils generates a magnetic field which traps the nano-sphere with surface-localized reaction complex at the adapter site. Thus, the reaction complex is localized on the surface of a light coupler at an adapter site in the waveguide, and may be localized in the confined space near the surface of the core layer of the waveguide.

3.6 Example 6—Localization at a Waveguide Adapter Site of an Asymmetrically Magnetic Nano-Sphere with a Surface-Localized Nucleic Acid-Synthesizing Complex A nano-sphere particle is modified with magnetic functional groups on a portion of its surface. A nucleic acid-synthesizing reaction complex is localized onto the magnetically-modified surface of the nano-sphere as described in any one of Examples 2-4, wherein the same surface of the nano-sphere that is modified with magnetic functional groups is also modified with streptavidin. The nano-sphere with surface-localized reaction complex is localized at an adapter site formed in a waveguide by use of micro-fabricated coils located underneath the adapter site. Passing an electric current through the micro-fabricated coils generates a magnetic field which traps the nano-sphere with adsorbed reaction complex at the adapter site, with the magnetically-modified surface with adsorbed reaction complex facing the core layer of the waveguide. Thus, the reaction complex is localized at the adapter site in the confined space near the surface of the core layer of the waveguide.

3.7 Example 7—Localization at a Waveguide Adapter Site of a Conducting Material-Modified Nano-Sphere with a Surface-Localized Nucleic Acid-Synthesizing Complex A nano-sphere particle is uniformly surface-modified with conducting material, i.e. material comprising charged groups. A nucleic acid-synthesizing reaction complex is localized on the conducting material-modified surface of the nano-sphere as described in Example 1. The nano-sphere with surface-localized reaction complex is localized at an adapter site formed in a waveguide by use of a micro-fabricated electrode at the adapter site. The micro-fabricated electrode comprises a glass slide located underneath the adapter site, where the glass slide is coated with a layer of conducting material, e.g., indium tin oxide, which acts as the electrode conducting surface. A glass slide that is similarly coated with a conducting material and that is located above the sample solution containing the reaction-complex-loaded nano-spheres acts as the counteracting electrode. Electric current is applied to the micro-fabricated electrodes to generate an electric potential difference between the electrodes which traps the nano-sphere with surface-localized reaction complex at the adapter site. Thus, the reaction complex is localized on the surface of a light coupler at an adapter site in the waveguide, and may be localized in the confined space near the surface of the core layer of the waveguide.

3.8 Example 8—Localization at a Waveguide Adapter Site of a Nano-Sphere Asymmetrically Modified with Conducting Material and with a Surface-Localized Nucleic Acid-Synthesizing Complex A nano-sphere particle is modified with conducting material on a portion of its surface. A nucleic acid-synthesizing reaction complex is localized on the conducting material-modified surface of the nano-sphere as described in any one of Examples 2-4, wherein the same surface of the nano-sphere that is modified with conducting material is also modified with streptavidin. The nano-sphere with surface-localized reaction complex is localized at an adapter site formed in a waveguide by use of a micro-fabricated electrode at the adapter site. The micro-fabricated electrode comprises a glass slide located underneath the adapter site, where the glass slide is coated with a layer of conducting material, e.g., indium tin oxide, which acts as the electrode conducting surface. A glass slide that is similarly coated with a conducting material and that is located above the sample solution containing the reaction-complex-loaded nano-spheres acts as the counteracting electrode. Electric current is applied to the micro-fabricated electrodes to generate an electric potential difference between the electrodes which traps the nano-sphere with surface-localized reaction complex at the adapter site, with the surface of the nano-sphere modified with conducting material and the reaction complex facing the core layer of the waveguide. Thus, the reaction complex is localized at the adapter site in the confined space near the surface of the core layer of the waveguide.

3.9 Example 9—Localization at a Waveguide Adapter Site of a Hydrophilic Group-Modified Nano-Sphere with a Surface-Localized Nucleic Acid-Synthesizing Complex A nano-sphere particle is modified with hydrophilic functional groups on one hemisphere and hydrophobic groups on its other hemisphere. A nucleic acid-synthesizing reaction complex is localized on the hydrophilic surface of the nano-sphere as described in any one of Examples 2-4, wherein the same surface of the nano-sphere that is modified with hydrophilic groups is also modified with streptavidin. The nano-sphere with surface-localized reaction complex is localized at an adapter site which has hydrophilic surface modification at the reaction site and has hydrophobic surface modification outside the reaction site, as shown in FIG. 6 (where surfaces 1 and 3 are hydrophilic, and surfaces 2 and 4 are hydrophobic). The nano-sphere orients at the adapter site with the hydrophilic surface of the nano-sphere having the localized reaction complex positioned at the reaction site, facing the core layer of the waveguide. Thus, the reaction complex is localized at the adapter site in the confined space near the surface of the core layer of the waveguide.

3.10 Example 10—Sequencing of a Nucleic Acid-Synthesizing Reaction Complex Localized on a Movable Light Coupler A nucleic acid-synthesizing reaction complex localized on a nano-sphere particle is localized at an adapter site formed in a waveguide as described in any one of Examples 5-9. The sample solution comprises dNTPs labeled at their beta or gamma phosphates with a unique fluorophore for each of dATP, dCTP, dGTP, and dTTP. The sample solution may be supplemented with additional sequencing reagents, such as DNA polymerase and appropriate buffer components. The distance between the DNA replication fork and the surface of the nano-sphere is in the range of tens to hundreds of nanometers. At each step of the synthesis reaction, one of the four types of labeled dNTPs associates with the active site of the reaction complex, where it base pairs with the corresponding base of the target nucleic acid. The fluorescent label is excited by the evanescent light field formed at the bottom of adapter site and/or by the evanescent light field radiating from the surface of the nano-sphere. Incorporation of a fluorophore-labeled nucleotide polyphosphate into the growing nucleotide strand at the active site is detected in real-time by detecting emission of the dNTP-linked fluorophore. The identity of each incorporated nucleotide is determined by its fluorescent label, wherein the fluorescence label is then cleaved from the nucleotide upon incorporation into the growing strand. The sequence of the target nucleic acid is derived by converting the sequence of the fluorescence emission signals detected during the polymerization reaction into a nucleic acid sequence.

Figure 14:
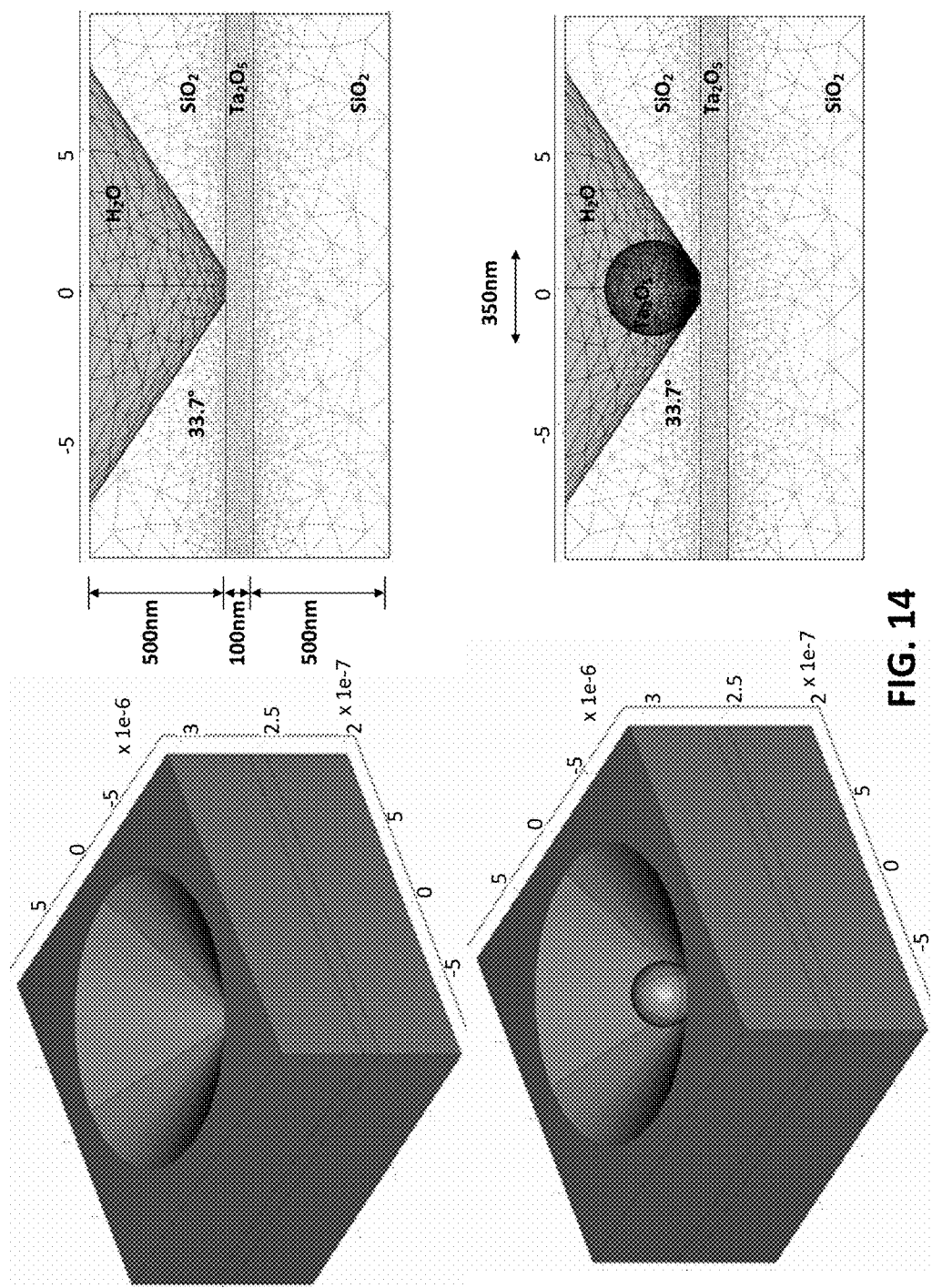
FIG. 14 shows schematic illustrations of an exemplary detection system configuration used for simulation of stationary electromagnetic fields produced by an incident excitation light wave.

3.11 Example 11—Simulation of the Excitation Light Field Generated Around the Surface of a 350 nm-Diameter Nano-Sphere Light Coupler by Optical Coupling of Light to the Nano-Sphere A simulation of excitation light propagation through a single mode waveguide comprising an adapter site and a nano-sphere light coupler demonstrates that a nano-sphere may couple light from the single mode waveguide. Schematic illustrations of a simulated detection system comprising a single mode waveguide, comprising a movable light coupler adapter site, and a nano-sphere light coupler are provided in FIG. 14. In the simulated system, both the light coupler nano-sphere ($Ta_2O_5$) and waveguide core layer ($Ta_2O_5$) have a refractive index of 2.26. The thickness of a core layer of the single mode waveguide is 100 nm, and the thickness of a lower cladding layer is 500 nm. The cladding layers of the waveguide are composed of $SiO_2$, having a refractive index of 1.487. The movable light coupler nano-sphere has a diameter of 350 nm and is positioned at the adapter site. The adapter site is an inverted, cone-shaped nanowell, and the nanowell has an opening angle (i.e., the angle from one side of the cone to the side directly opposite) of 112.6°. The diameter of the circular bottom of the nanowell is 100 nm, and the nanowell is filled with water, which has a refractive index of 1.33. In such a configuration, both the light coupler and the core layer allow the propagation of light waves with single transverse electric (TE) and transverse magnetic (TM) modes.

The wavelength of incident light is 473 nm. The stationary electric field and magnetic field distribution in the system are calculated using source-free Maxwell's equations. (See, for reference, Katrin Schmitt and Christian Hoffmann, "High-Refractive-Index Waveguide Platforms for Chemical and Biosensing", in OPTICAL GUIDED-WAVE CHEMICAL AND BIOSENSORS I, SPRINGER SERIES ON CHEMICAL SENSORS AND BIOSENSORS 7, 21 (M. Zourob and A. Lakhtakia eds., 2009.))

Figure 15:
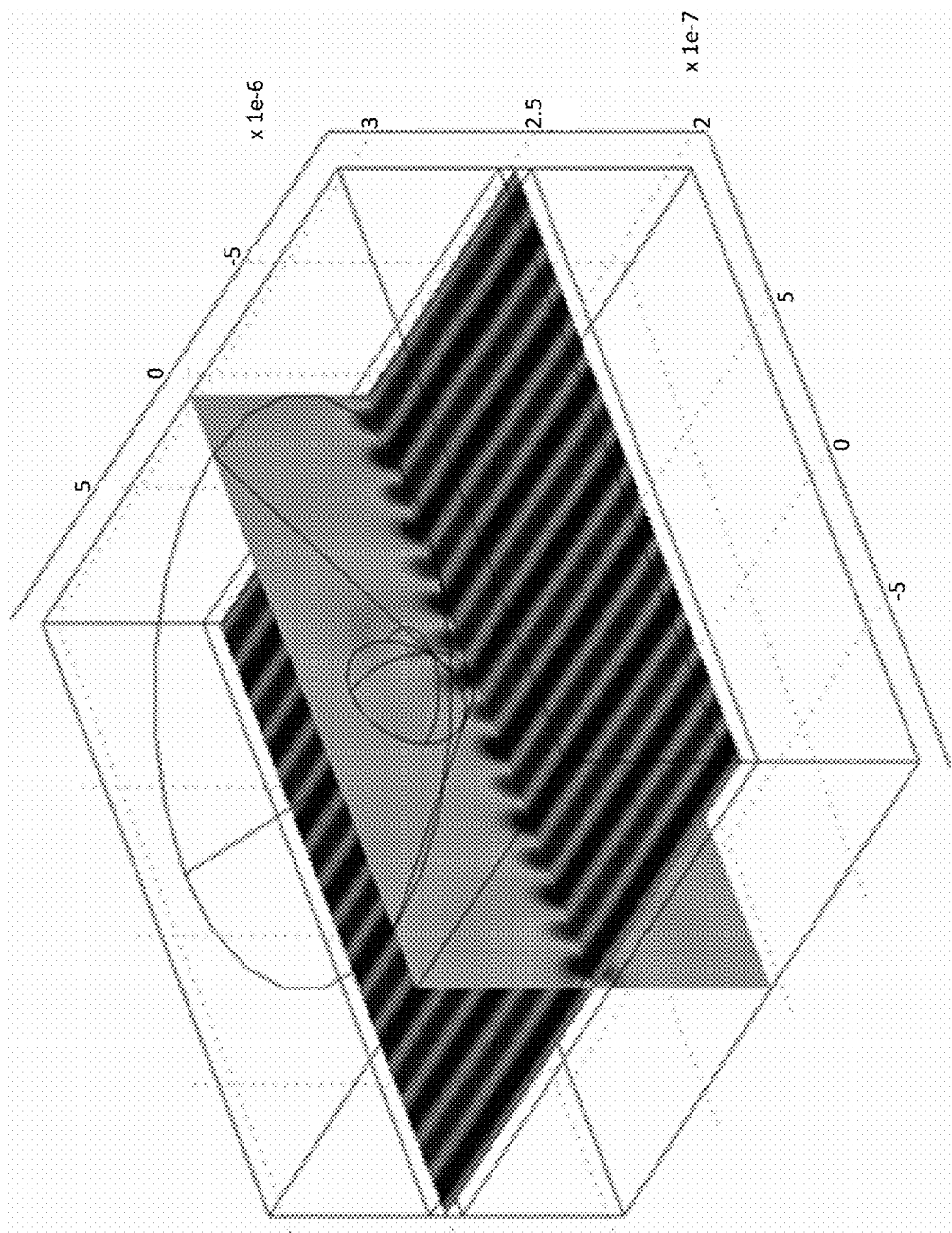
FIG. 15 shows a contour map of the calculated stationary TE-mode electric field for a simulated detection system.
Figure 16:
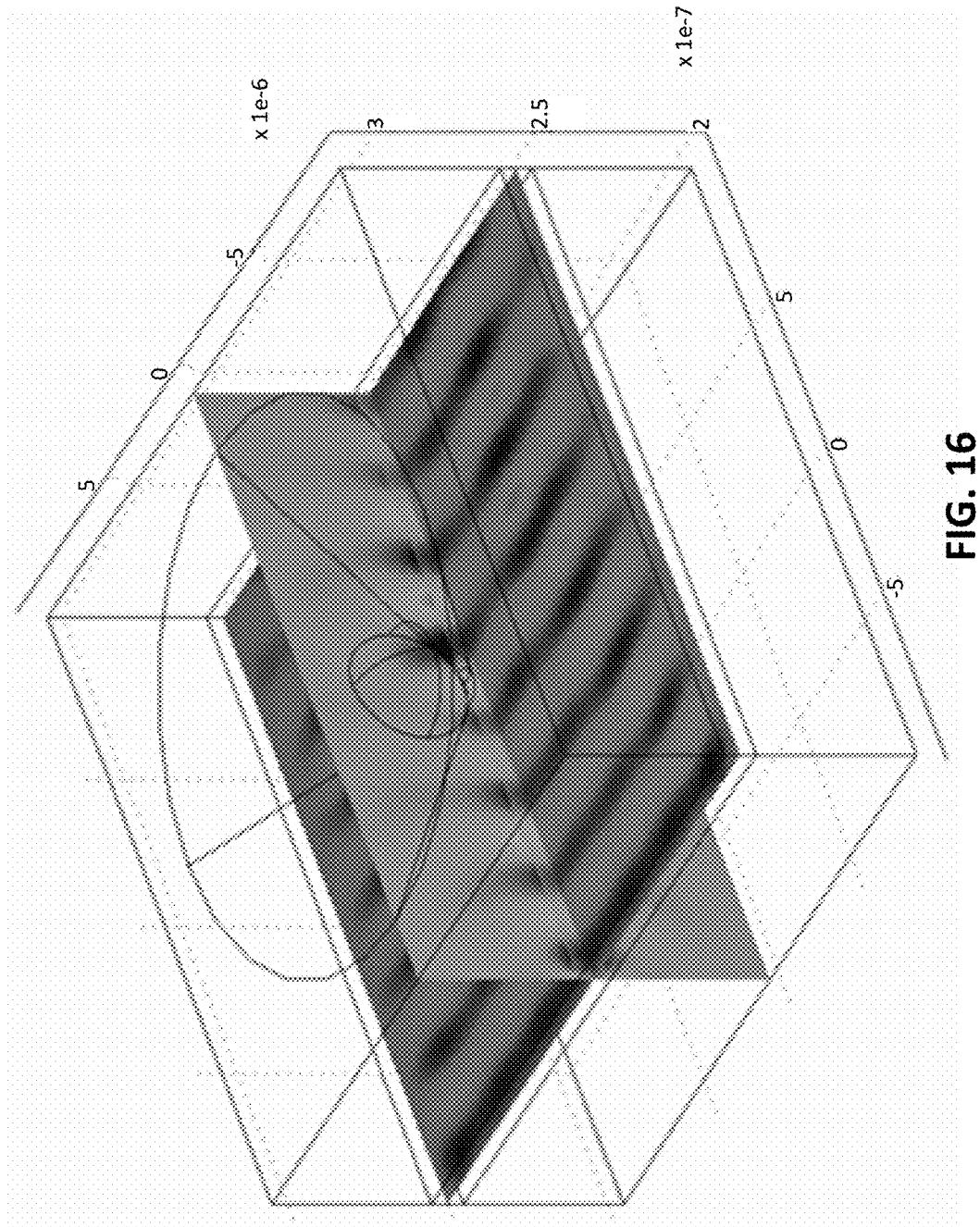
FIG. 16 shows a contour map of the calculated stationary TM-mode electric field for a simulated detection system.
Figure 17:
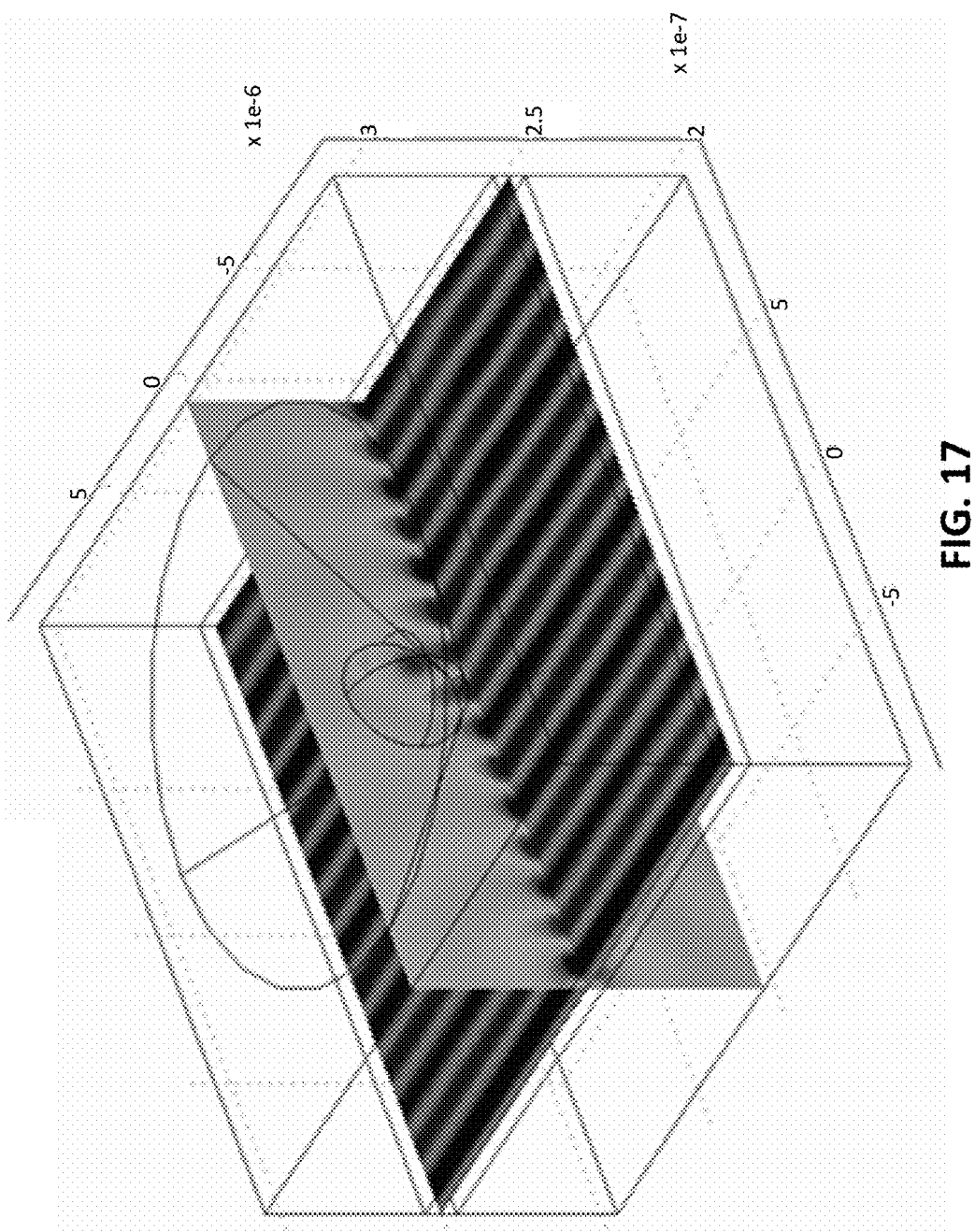
FIG. 17 shows a contour map of the calculated stationary magnetic field for a simulated detection system.
Figure 18A:
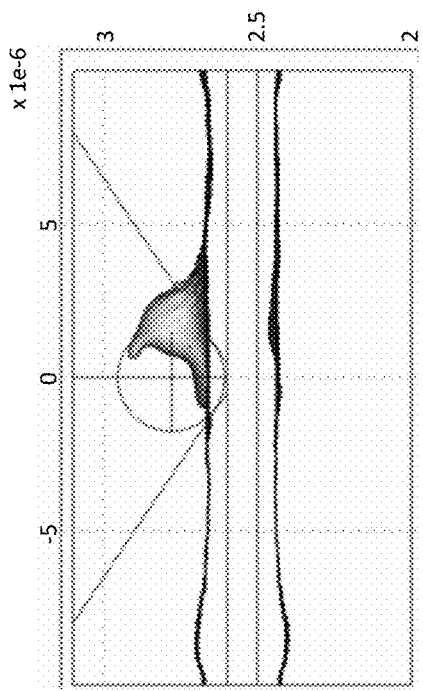
FIGS. 18 A, B, and C show contour maps of stationary electromagnetic fields produced by an incident excitation light wave in detection system configurations in which the nanowell does not extend into the core layer, extends partially into the core layer, and extends fully through the core layer, respectively.
Figure 18A:
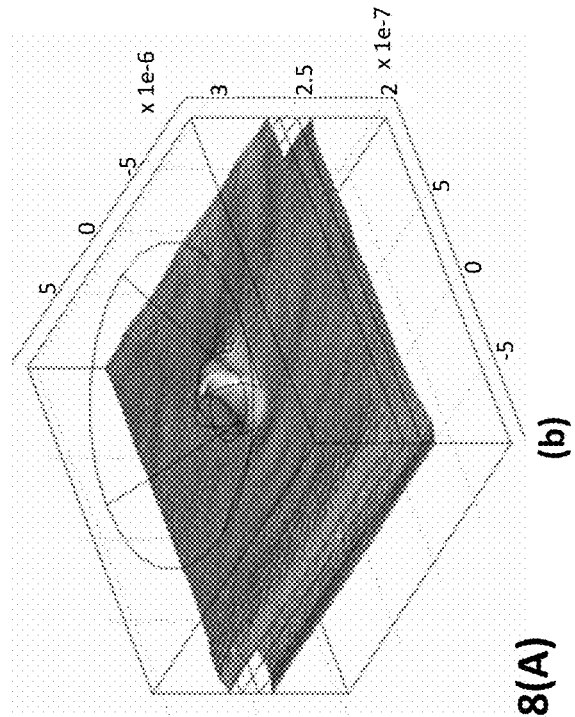
Figure 18A:
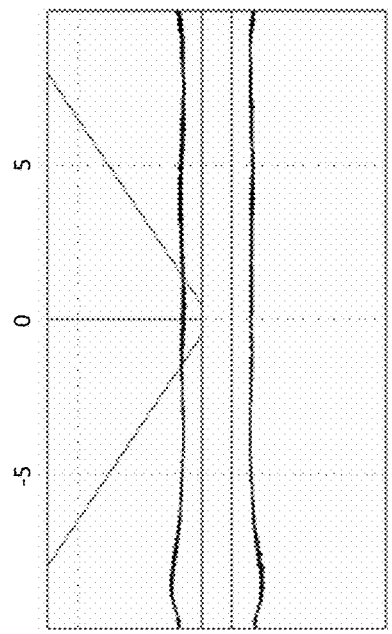
Figure 18A:
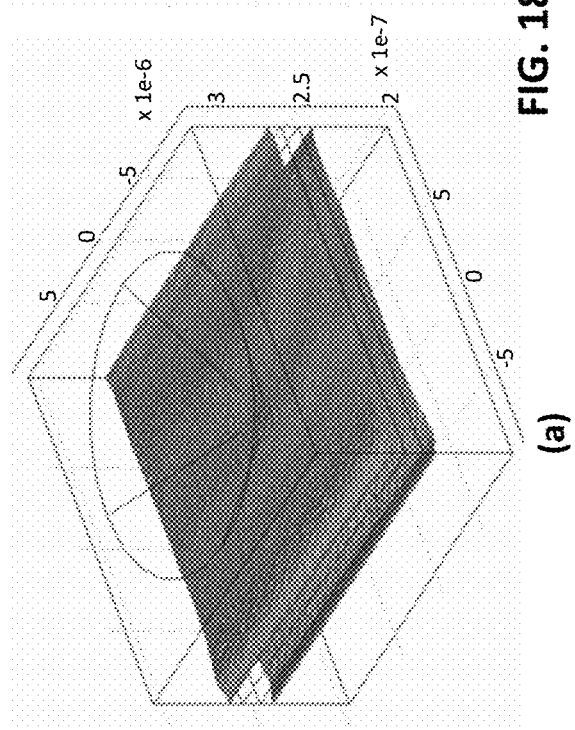
Figure 18B:
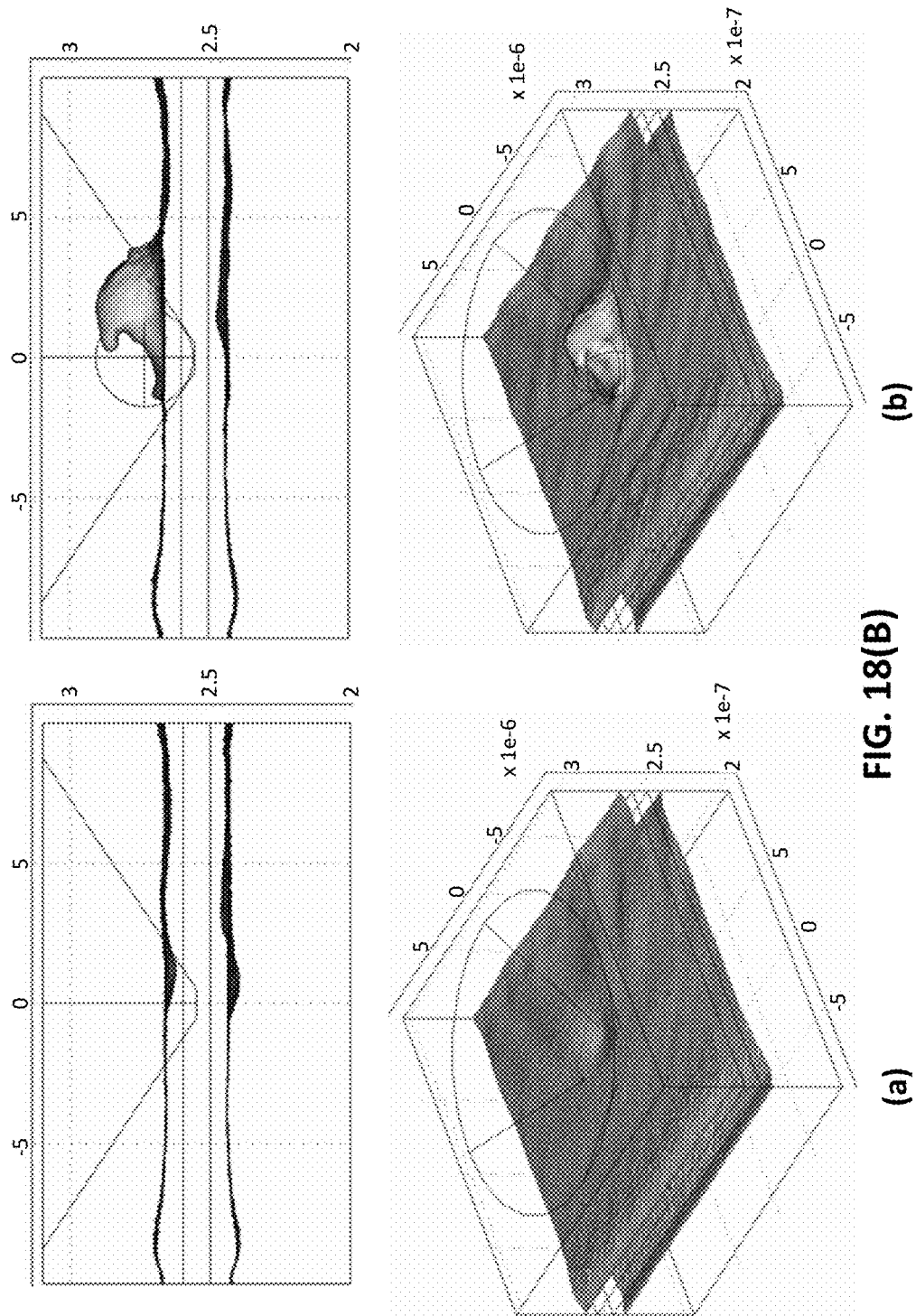
Figure 18C:
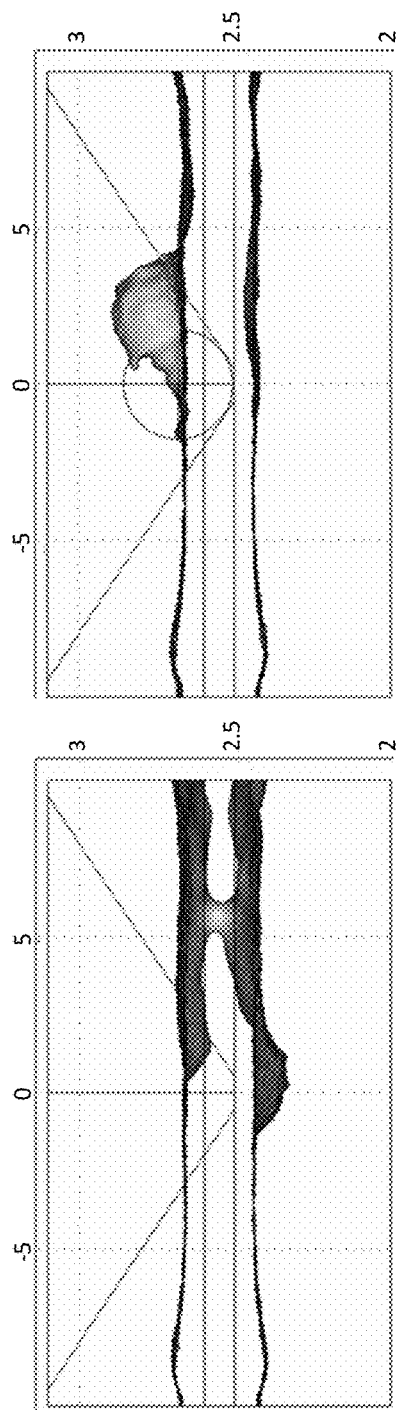
Figure 18C:
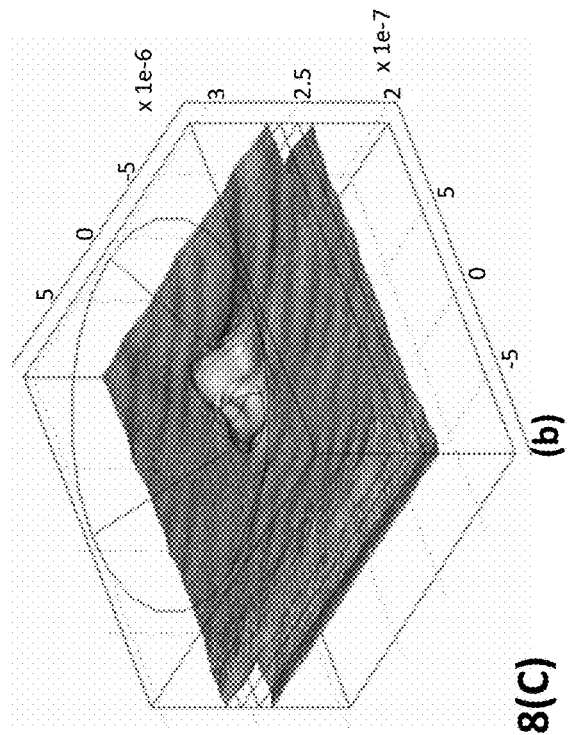
Figure 18C:
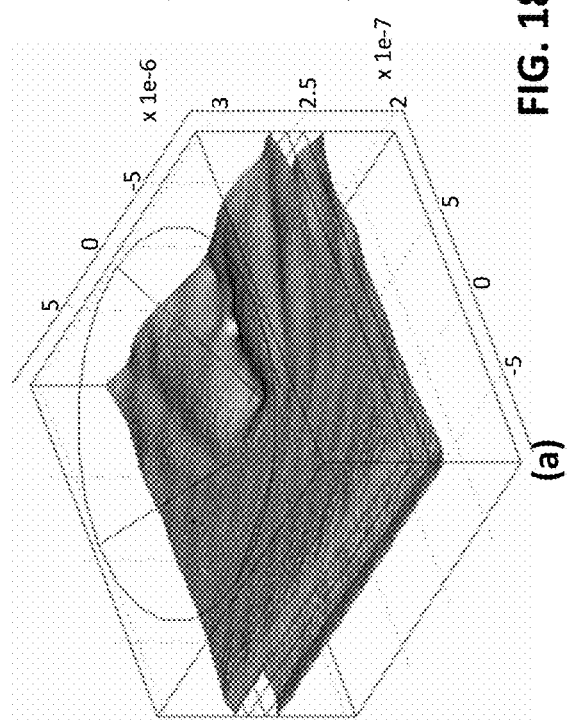

In this configuration, both the TE-mode and TM-mode fields propagate along the core layer of the waveguide and the region of the surface of the nano-sphere, as shown in FIG. 15 (TE-mode field) and FIG. 16 (TM-mode field). Like the stationary electric field, a portion of the stationary magnetic field transfers from the core layer to the region of the surface of the nano-sphere, as shown in FIG. 17.

In further simulations, the adapter site is extended into the core layer of the waveguide. The light field of the system wherein the nanowell does not extend into the core layer, extends partially into the core layer, and extends completely into the core layer is shown topologically in FIGS. 18 A, B, and C, respectively. The images on the left of FIGS. 18 A, B, and C (labeled (a)) depict the intensity contours of the light field in the waveguide. The images on the right of FIGS. 18 A, B, and C (labeled (b)) depict the intensity contours of the light field in the detection system when the nano-sphere is positioned at the adapter site. The energy is transmitted around the waveguide in three kinds of thickness in the absence of the nano-sphere. However, when the nano-sphere is positioned at the adapter site, a light field will be induced on the surface of the nano-sphere. The intensity of this induced light field increases as the distance which the adapter site extends into the core layer of the waveguide increases.

3.12 Example 12—Simulation of the Excitation Light Field Generated Around the Surface of a 100 nm-Diameter Nano-Sphere Light Coupler by Optically Coupling Light to the Nano-Sphere In a simulation similar to that described in Example 11, the diameter of a $Ta_2O_5$ light coupler nano-sphere is 100 nm. The thickness of a $Ta_2O_5$ core layer of the single mode waveguide is 100 nm. The cladding layers of the waveguide are composed of $SiO_2$. The thickness of a lower cladding layer is 500 nanometers. The adapter site is a cone-shaped nanowell, and the opening angle of the conical nanowell (i.e., the angle from one side of the cone to the side directly opposite) is 112.6°. The diameter of the circular bottom of the nanowell is 100 nm, and the nanowell is filled with water (having a refractive index of 1.33). A schematic illustration of a simulated detection system according to this configuration is provided in FIG. 19. The incident wave is a 473 nm-wavelength TE-polarized optical field. The majority of the electric field remains in the immediate proximity to the core layer of the waveguide, as shown in FIG. 20(a; right image), which provides a contour map of the simulated stationary electric field distribution. The light energy of the detection system is shown in FIG. 20(b), which illustrates the light field induced on the lower surface of the nano-sphere (shown at high magnification at right).

Figure 19:
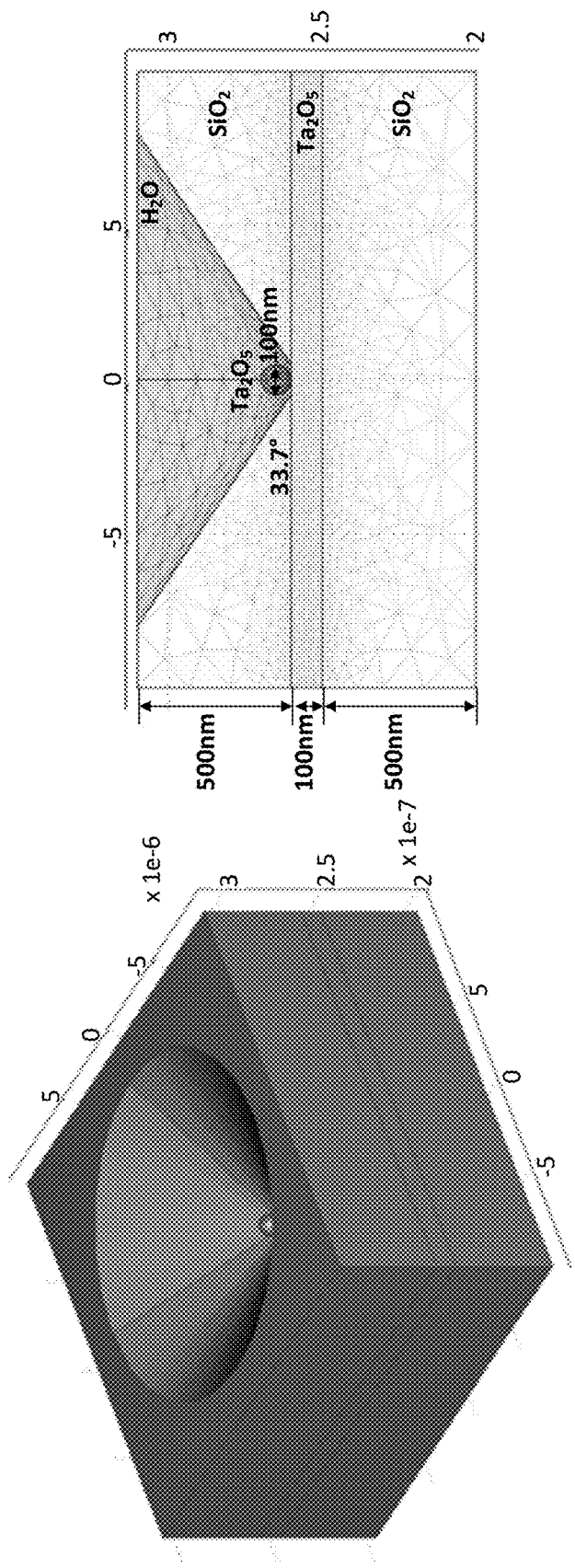
FIG. 19 shows schematic illustrations of an exemplary detection system configuration used for simulation of stationary electromagnetic fields produced by an incident excitation light wave.
Figure 20:
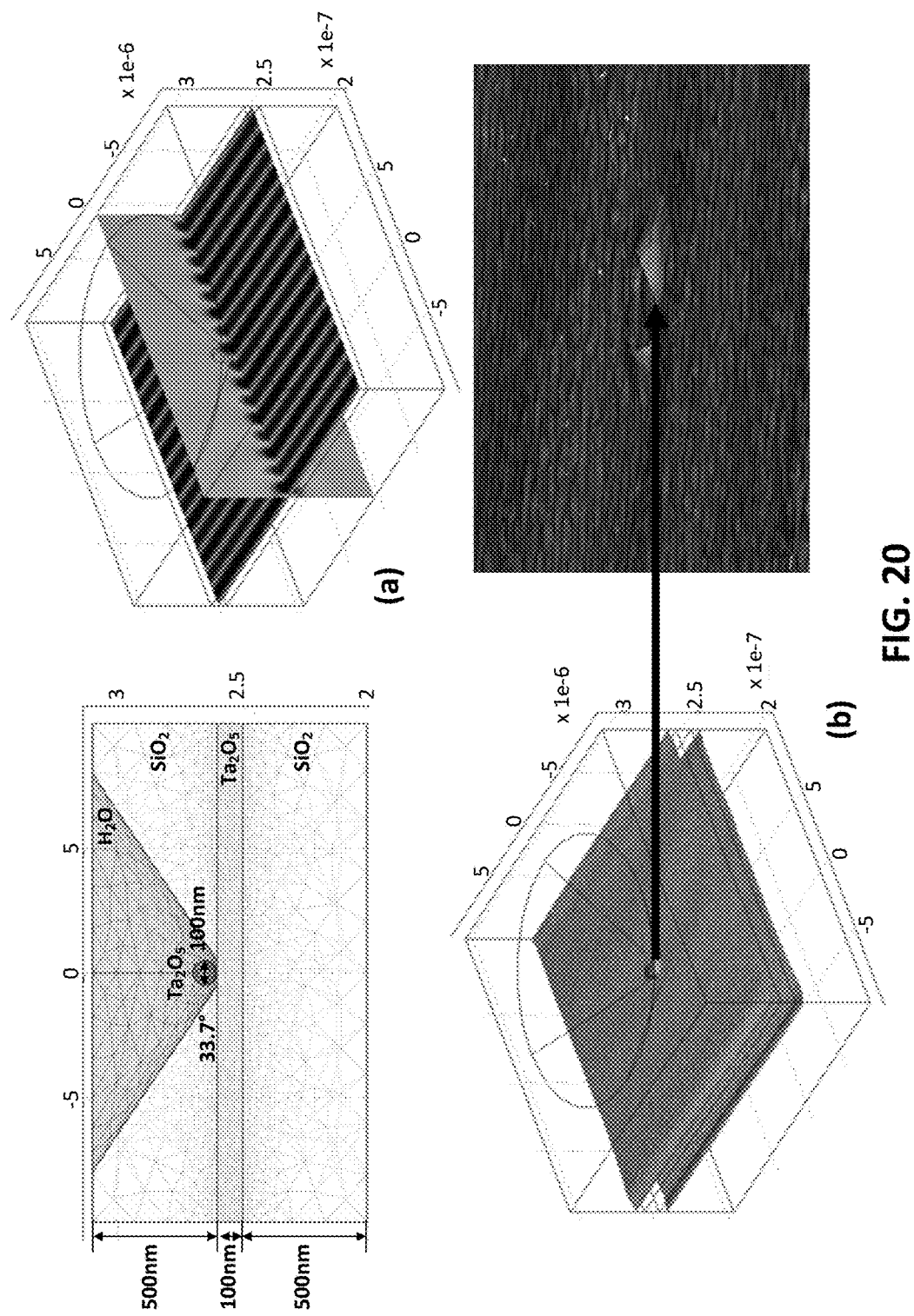
FIG. 20 shows contour maps of the calculated stationary electric field for a simulated detection system.
Figure 21:
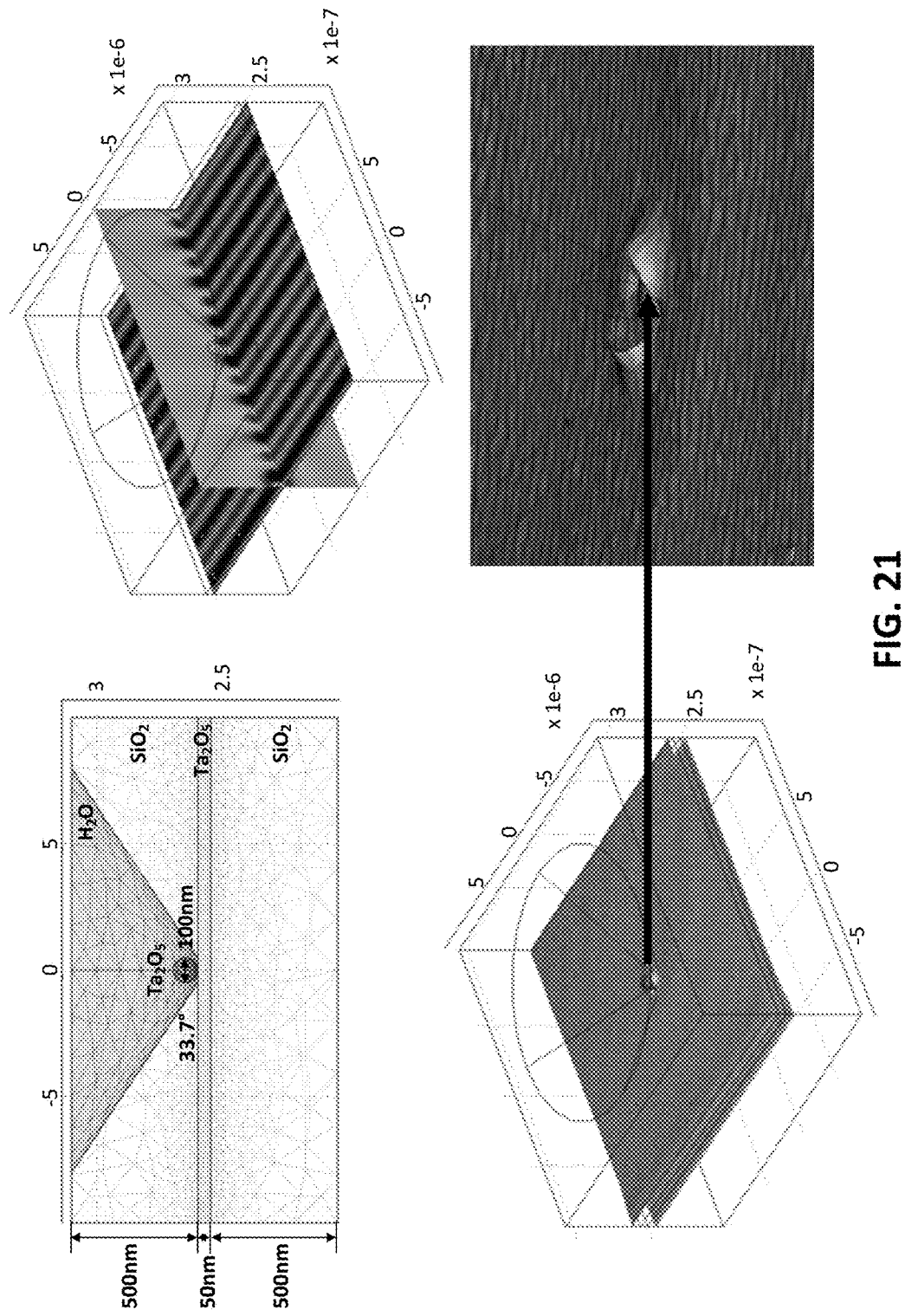
FIG. 21 shows contour maps of the calculated stationary electric field for a simulated detection system.

In a further simulation, the system diagrammed in FIG. 19 is utilized, but the thickness of the core layer of the waveguide is 50 nm instead of 100 nm. The incident wave is a 473 nm-wavelength TE-polarized optical field. The simulated stationary electric field distribution is shown in FIG. 21. The light field induced on the lower surface of the nano-sphere is shown in the lower images of FIG. 21.

Figure 22:
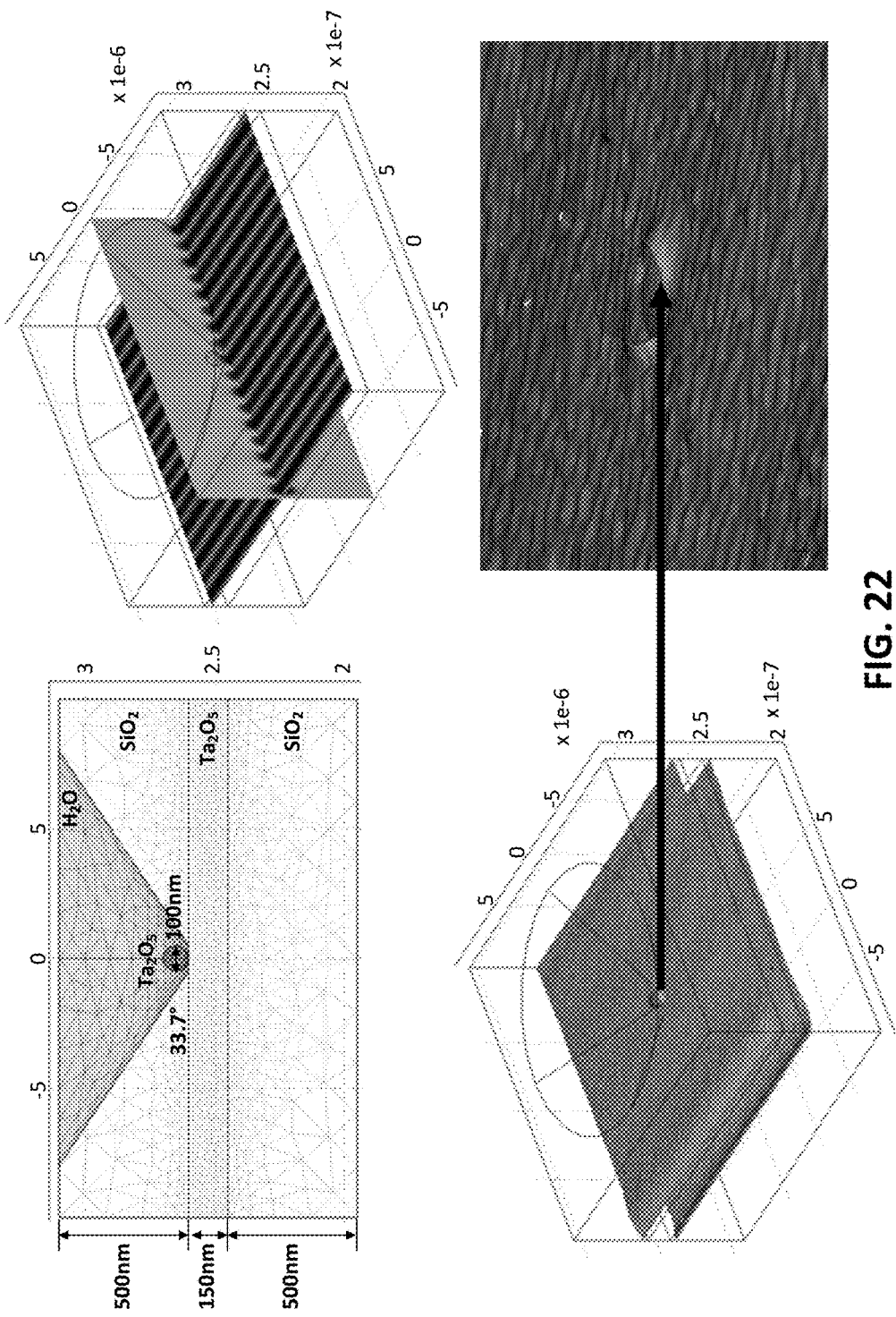
FIG. 22 shows contour maps of the calculated stationary electric field for a simulated detection system.

In a further simulation, the system diagrammed in FIG. 19 is utilized, but the thickness of the core layer of the waveguide is 150 nm instead of 100 nm. The incident wave is a 473 nm-wavelength TE-polarized optical field. The simulated stationary electric field distribution is shown in FIG. 22. The light field induced on the lower surface of the nano-sphere is shown in the lower images of FIG. 22.

In these configurations, a portion of the stationary electric field and the light energy transfers from the core layer of the waveguide to the lower region of the surface of the nano-sphere, as shown in FIGS. 20, 21 and 22.

What is claimed is:

1. A method of sequencing a nucleic acid, comprising:
providing a detection apparatus comprising
a movable light coupler;
a waveguide comprising:
    a core layer, and
    a first cladding layer,
        wherein at least one adapter site for the movable light coupler is formed in at least the first cladding layer; and
a light detector;
providing at least one nucleic acid molecule;
localizing the at least one nucleic acid molecule individually on the movable light coupler;
localizing at the adapter site the movable light coupler on which the at least one nucleic acid is localized;
generating an evanescent field introduced by a light wave propagating along the core layer;
coupling the evanescent field to the movable light coupler, and thereby forming an induced light field around the surface of the movable light coupler;
performing single molecule sequencing-by-synthesis of the at least one nucleic acid molecule, wherein the single molecule nucleic acid sequencing-by-synthesis leads to production of an emitted light correlated to the identity of at least one base in the nucleic acid;
detecting the emitted light with the detector, resulting in an output signal; and
processing the output signal to determine an identity of at least one base comprised by the nucleic acid.

2. The method of claim 1, wherein the refractive index of the movable light coupler is higher than the refractive index of the first cladding layer, and the refractive index of the core layer is higher than the refractive index of the first cladding lay.

* * * * *

UNITED STATES PATENT AND TRADEMARK OFFICE
CERTIFICATE OF CORRECTION

| | |
|---|---|
| PATENT NO. | : 9,777,321 B2 |
| APPLICATION NO. | : 15/260773 |
| DATED | : October 3, 2017 |
| INVENTOR(S) | : Chung-Fan Chiou et al. |

It is certified that error appears in the above-identified patent and that said Letters Patent is hereby corrected as shown below:

In the Claims

In Claim 2, Column 44, Line 33-34, change "the first cladding lay." to --the first cladding layer.--.

Signed and Sealed this
Twenty-sixth Day of December, 2017

Joseph Matal
*Performing the Functions and Duties of the
Under Secretary of Commerce for Intellectual Property and
Director of the United States Patent and Trademark Office*